(12) United States Patent
Patton et al.

(10) Patent No.: US 11,185,080 B2
(45) Date of Patent: *Nov. 30, 2021

(54) ANTIMICROBIAL COMPOSITIONS

(71) Applicant: MATOKE HOLDINGS LIMITED, Abingdon (GB)

(72) Inventors: Thomas Patton, Rathrippon Collooney (IE); James Brennan, Hazelwood (IE); John Reginald Barrett, Templemore (IE); Ian Staples, Abindgon (IE)

(73) Assignee: MATOKE HOLDINGS LIMITED, Abingdon (GB)

( * ) Notice: Subject to any disclaimer, the term of this patent is extended or adjusted under 35 U.S.C. 154(b) by 363 days.

This patent is subject to a terminal disclaimer.

(21) Appl. No.: 15/685,509

(22) Filed: Aug. 24, 2017

(65) Prior Publication Data

US 2018/0042240 A1    Feb. 15, 2018

Related U.S. Application Data

(63) Continuation of application No. 15/307,564, filed as application No. PCT/GB2014/051337 on Apr. 30, 2014.

(51) Int. Cl.
| | | |
|---|---|---|
| *A01N 63/00* | (2020.01) | |
| *A01N 63/50* | (2020.01) | |
| *A01N 59/00* | (2006.01) | |
| *A23L 29/00* | (2016.01) | |
| *A23L 21/25* | (2016.01) | |
| *A23L 33/10* | (2016.01) | |
| *A61K 38/44* | (2006.01) | |
| *A61K 35/644* | (2015.01) | |
| *A61L 15/46* | (2006.01) | |
| *A61L 15/38* | (2006.01) | |
| *A61L 15/40* | (2006.01) | |
| *A01N 65/00* | (2009.01) | |

(52) U.S. Cl.
CPC ............. *A01N 63/50* (2020.01); *A01N 59/00* (2013.01); *A01N 65/00* (2013.01); *A23L 21/25* (2016.08); *A23L 29/06* (2016.08); *A23L 33/10* (2016.08); *A61K 35/644* (2013.01); *A61K 38/443* (2013.01); *A61L 15/38* (2013.01); *A61L 15/40* (2013.01); *A61L 15/46* (2013.01); *C12Y 101/03004* (2013.01); *A61L 2300/254* (2013.01); *A61L 2300/404* (2013.01)

(58) Field of Classification Search
CPC ....... A23L 21/25; A23L 29/06; A61K 35/644; A61K 38/443; A61L 15/38; A61L 15/40; A61L 2300/254; A61L 2300/404; A01N 63/50; C12Y 101/03004

See application file for complete search history.

(56) References Cited

U.S. PATENT DOCUMENTS

| | | |
|---|---|---|
| 1,987,893 A | 1/1935 | Dyce |
| 3,770,588 A | 11/1973 | Forgione |
| 4,537,763 A | 8/1985 | Miyake et al. |
| 4,537,764 A | 8/1985 | Pellico et al. |
| 4,576,817 A | 3/1986 | Montgomery et al. |
| 4,578,265 A | 3/1986 | Pellico et al. |
| 4,961,939 A | 10/1990 | Antrim et al. |
| 4,996,062 A | 2/1991 | Lehtonen et al. |
| 5,167,950 A | 12/1992 | Lins |
| 5,389,369 A | 2/1995 | Allen |
| 5,451,402 A | 9/1995 | Allen |
| 5,510,104 A | 4/1996 | Allen |
| 5,565,197 A | 10/1996 | Allen |
| 5,607,681 A | 3/1997 | Galley et al. |
| 5,718,896 A | 2/1998 | Allen |
| 5,730,933 A | 3/1998 | Peterson |
| 5,756,090 A | 5/1998 | Allen |
| 5,888,505 A | 3/1999 | Allen |
| 5,980,875 A | 11/1999 | Mousa |
| 6,033,662 A | 3/2000 | Allen |
| 6,103,245 A | 8/2000 | Clark et al. |
| 6,214,339 B1 | 4/2001 | Pellico |

(Continued)

FOREIGN PATENT DOCUMENTS

| | | |
|---|---|---|
| AU | 2003234758 A1 | 3/2004 |
| DE | 42 38 779 A1 | 5/1994 |

(Continued)

OTHER PUBLICATIONS

English-language translation of Japanese Notice of Reasons for Rejection dated Jul. 24, 2018 received in Japanese Patent Application No. 2016-565373.

(Continued)

*Primary Examiner* — Taeyoon Kim
*Assistant Examiner* — Tiffany M Gough
(74) *Attorney, Agent, or Firm* — Scully, Scott, Murphy & Presser, P.C.

(57) ABSTRACT

Storage-stable compositions for generating antimicrobial activity are described. The compositions comprise an enzyme that is able to convert a substrate to release hydrogen peroxide, and an unrefined natural substance, such as a honey, that includes a substrate for the enzyme. In certain embodiments, the enzyme is a purified enzyme. In other embodiments, the substrate lacks catalase activity, and the enzyme is additional to any enzyme activity able to convert the substrate to release hydrogen peroxide that may be present in the unrefined natural substance. The storage-stable compositions do not include sufficient free water to allow the enzyme to convert the substrate. Use of the compositions to treat microbial infections and wounds is described, as well as methods for their production.

8 Claims, 42 Drawing Sheets

(56) References Cited

U.S. PATENT DOCUMENTS

| | | |
|---|---|---|
| 6,294,168 B1 | 9/2001 | Allen |
| 6,503,507 B1 | 1/2003 | Allen |
| 6,656,702 B1 | 12/2003 | Yugawa et al. |
| 6,716,611 B2 | 4/2004 | Dana et al. |
| 6,774,111 B1 | 8/2004 | Wolf et al. |
| 6,932,979 B2 | 8/2005 | Gergely et al. |
| 6,956,144 B2 | 10/2005 | Molan |
| 7,060,311 B1 | 6/2006 | Milani et al. |
| 7,399,400 B2 | 7/2008 | Soundarrajan et al. |
| 7,563,224 B2 | 7/2009 | Puchek |
| 7,714,183 B2 | 5/2010 | Caskey |
| 7,731,954 B2 | 6/2010 | Davis et al. |
| 7,927,588 B2 | 4/2011 | Davis et al. |
| 8,026,407 B2 | 9/2011 | Downs et al. |
| 8,343,552 B2 | 1/2013 | Huang et al. |
| 8,679,526 B2 | 3/2014 | Van Den Plas et al. |
| 8,679,796 B2 | 3/2014 | Carvalho Fernandes De Miranda Reis et al. |
| 8,871,248 B2 | 10/2014 | Rodeheaver et al. |
| 8,879,575 B2 | 11/2014 | Zheng et al. |
| 8,895,282 B2 | 11/2014 | Tano |
| 8,945,540 B2 | 2/2015 | Becquerelle et al. |
| 8,986,716 B2 | 3/2015 | Gonry et al. |
| 8,999,720 B2 | 4/2015 | Kristensen et al. |
| 9,283,278 B2 | 3/2016 | Rodeheaver et al. |
| 9,333,260 B2 | 5/2016 | Pellico et al. |
| 9,393,249 B2 | 7/2016 | Barrett et al. |
| 9,421,287 B2 | 8/2016 | Kristensen et al. |
| 9,452,237 B2 | 9/2016 | Leech et al. |
| 9,522,165 B2 | 12/2016 | Barrett et al. |
| 9,661,876 B2 | 5/2017 | Mua et al. |
| 9,861,560 B2 | 1/2018 | Bernard et al. |
| 9,994,725 B2 | 6/2018 | Svoboda et al. |
| 2002/0028197 A1 | 3/2002 | Fitchett |
| 2002/0087106 A1 | 7/2002 | Unger et al. |
| 2002/0119136 A1 | 8/2002 | Johansen |
| 2002/0150621 A1 | 10/2002 | Kohane et al. |
| 2002/0150626 A1 | 10/2002 | Kohane et al. |
| 2002/0182600 A1 | 12/2002 | Smith |
| 2003/0228264 A1 | 12/2003 | Perna |
| 2004/0054313 A1 | 3/2004 | Molan |
| 2004/0127826 A1 | 7/2004 | Caskey |
| 2004/0131693 A1 | 7/2004 | Postmes et al. |
| 2005/0033213 A1 | 2/2005 | Bray et al. |
| 2005/0181026 A1 | 8/2005 | Davis et al. |
| 2005/0221029 A1 | 10/2005 | Cater et al. |
| 2005/0238635 A1 | 10/2005 | Tano |
| 2006/0034816 A1 | 2/2006 | Davis et al. |
| 2006/0099166 A1 | 5/2006 | Vandeputte |
| 2006/0165802 A1 | 7/2006 | Lotzbeyer et al. |
| 2006/0275350 A1 | 12/2006 | Davis et al. |
| 2006/0281165 A1 | 12/2006 | Davis et al. |
| 2007/0003632 A1 | 1/2007 | Lapointe |
| 2007/0190122 A1 | 8/2007 | Davis et al. |
| 2007/0207215 A1 | 9/2007 | Abashidze et al. |
| 2008/0033329 A1 | 2/2008 | Downs et al. |
| 2008/0125617 A1 | 5/2008 | Puchek |
| 2008/0169217 A1 | 6/2008 | Bonneau et al. |
| 2008/0305096 A1 | 12/2008 | Verdegem et al. |
| 2008/0312572 A1 | 12/2008 | Riesinger |
| 2009/0148537 A1 | 6/2009 | Molan |
| 2009/0202615 A1 | 8/2009 | Rodeheaver et al. |
| 2009/0263467 A1 | 10/2009 | Joshi |
| 2009/0291122 A1 | 11/2009 | Vandeputte |
| 2009/0317474 A1 | 12/2009 | Van Den Plas et al. |
| 2010/0028408 A1 | 2/2010 | Vandeputte |
| 2010/0049262 A1 | 2/2010 | Puchek et al. |
| 2010/0095645 A1 | 4/2010 | Tippery et al. |
| 2010/0098645 A1 | 4/2010 | Barrett et al. |
| 2010/0135926 A1 | 6/2010 | Barret et al. |
| 2010/0143534 A1 | 6/2010 | Brinker et al. |
| 2010/0150897 A1 | 6/2010 | Pellico et al. |
| 2010/0158885 A1 | 6/2010 | Huang et al. |
| 2010/0189707 A1 | 7/2010 | Barnett |
| 2010/0233283 A1 | 9/2010 | Moloney |
| 2011/0039004 A1 | 2/2011 | Garter |
| 2011/0044966 A1 | 2/2011 | Tano |
| 2011/0052557 A1 | 3/2011 | Huang et al. |
| 2011/0052664 A1 | 3/2011 | Tennican et al. |
| 2011/0059062 A1 | 3/2011 | Pellico |
| 2011/0070198 A1 | 3/2011 | Huang et al. |
| 2011/0117071 A1 | 5/2011 | Barrett et al. |
| 2011/0135621 A1 | 6/2011 | Miller et al. |
| 2011/0159104 A1 | 6/2011 | Teslenko |
| 2011/0250256 A1 | 10/2011 | Hyun-Oh et al. |
| 2011/0263528 A1 | 10/2011 | Keiji et al. |
| 2012/0021061 A1 | 1/2012 | Schlothauer et al. |
| 2012/0058074 A1 | 3/2012 | Braig et al. |
| 2012/0244091 A1 | 9/2012 | Chopra et al. |
| 2012/0258087 A1 | 10/2012 | Jedlinski et al. |
| 2012/0269879 A1 | 10/2012 | Watson |
| 2013/0029030 A1 | 1/2013 | Larsen |
| 2013/0098775 A1 | 4/2013 | Pei et al. |
| 2013/0101661 A1 | 4/2013 | Rodeheaver et al. |
| 2013/0273020 A1 | 10/2013 | Gannabathula et al. |
| 2014/0023597 A1 | 1/2014 | Barrett et al. |
| 2014/0120076 A1 | 5/2014 | Stephens, Jr. et al. |
| 2014/0134213 A1 | 5/2014 | O'Flaherty et al. |
| 2014/0154193 A1 | 6/2014 | Barrett et al. |
| 2014/0199266 A1 | 7/2014 | Park et al. |
| 2014/0308399 A1 | 10/2014 | Domingues |
| 2014/0316353 A1 | 10/2014 | Riesinger |
| 2015/0030688 A1 | 1/2015 | Sell et al. |
| 2015/0079196 A1 | 3/2015 | Chakravarthy et al. |
| 2015/0080815 A1 | 3/2015 | Chakravarthy et al. |
| 2015/0099009 A1 | 4/2015 | Rodeheaver et al. |
| 2015/0125511 A1 | 5/2015 | Kageyama et al. |
| 2015/0182563 A1 | 7/2015 | Park et al. |
| 2015/0189907 A1 | 7/2015 | Donaldson et al. |
| 2015/0282513 A1 | 10/2015 | Cook et al. |
| 2015/0297644 A1 | 10/2015 | Park et al. |
| 2015/0366245 A1 | 12/2015 | Van Egeren |
| 2016/0101210 A1 | 4/2016 | Watson |
| 2016/0220722 A1 | 4/2016 | Wardell et al. |
| 2016/0144004 A1 | 5/2016 | Pellico |
| 2016/0151533 A1 | 6/2016 | Rodeheaver et al. |
| 2016/0186230 A1 | 6/2016 | Kaneda |
| 2016/0199421 A1 | 7/2016 | Kuhne et al. |
| 2016/0279205 A1 | 9/2016 | Pellico et al. |
| 2017/0049111 A1 | 2/2017 | Patton et al. |
| 2017/0072024 A1 | 3/2017 | Malepeyre et al. |
| 2017/0166938 A1 | 6/2017 | Nagy et al. |
| 2017/0202869 A1 | 7/2017 | Madsen, II et al. |
| 2017/0266240 A1 | 9/2017 | Patton et al. |
| 2017/0304452 A1 | 10/2017 | Teruya et al. |
| 2018/0133358 A1 | 5/2018 | Cullen et al. |
| 2018/0177723 A1 | 6/2018 | Devraj et al. |

FOREIGN PATENT DOCUMENTS

| | | |
|---|---|---|
| DE | 103 59316 A1 | 7/2006 |
| DE | 102012100842 A1 | 8/2013 |
| EP | 0133736 A2 | 3/1985 |
| EP | 0 149 096 A2 | 7/1985 |
| EP | 0 236 610 A1 | 9/1987 |
| EP | 0 240 938 A2 | 10/1987 |
| EP | 0 500 387 A2 | 8/1992 |
| EP | 0 518 445 A1 | 12/1992 |
| EP | 0 263 147 B1 | 12/1994 |
| EP | 0 923 939 A1 | 6/1999 |
| EP | 1 230 911 A1 | 8/2002 |
| EP | 1373452 | 9/2002 |
| EP | 1 358 893 A1 | 11/2003 |
| EP | 1 693 073 A2 | 8/2006 |
| EP | 1 852 017 A1 | 11/2007 |
| EP | 1 884 253 A1 | 2/2008 |
| EP | 2 120 851 | 7/2008 |
| EP | 1 237 561 B2 | 4/2009 |
| EP | 2 300 047 | 12/2009 |
| EP | 2 367 443 | 7/2010 |
| EP | 2 506 824 | 6/2011 |
| EP | 2 563 736 | 11/2011 |
| EP | 2 510 944 A1 | 10/2012 |
| EP | 2 721 933 A1 | 4/2014 |

(56) References Cited

FOREIGN PATENT DOCUMENTS

| | | |
|---|---|---|
| EP | 2 801 257 A1 | 11/2014 |
| FR | 2899064 A1 | 10/2007 |
| FR | 3 020 758 A1 | 11/2015 |
| GB | 2391809 A | 2/2004 |
| GB | 2 432 790 A | 6/2007 |
| GB | 2 435 426 A | 8/2007 |
| GB | 2484319 A | 4/2012 |
| GB | 2540130 A | 1/2017 |
| GB | 2540054 A | 4/2017 |
| GB | 2547402 A | 8/2017 |
| GN | 101909666 A | 12/2010 |
| IE | 2009/0232 A1 | 10/2009 |
| JP | S59231011 A | 12/1984 |
| JP | 562213754 A | 9/1987 |
| JP | H05-504567 A | 7/1993 |
| JP | 2000509367 A | 7/2000 |
| JP | 2001521878 A | 11/2001 |
| JP | 2008501361 A | 1/2008 |
| JP | 2010532788 A | 10/2010 |
| JP | 2012006971 A | 1/2012 |
| JP | 2012162621 A | 8/2012 |
| JP | 2013-513608 A | 4/2013 |
| JP | 6-503251 B2 | 4/2019 |
| NZ | 582246 A | 7/2011 |
| PL | 222559 B1 | 1/2014 |
| RU | 2447880 C2 | 4/2012 |
| RU | 2480018 C2 | 4/2013 |
| UA | 117416 C2 | 7/2018 |
| WO | 88/02600 A1 | 4/1988 |
| WO | 92/11042 A1 | 7/1992 |
| WO | WO 92/14484 A1 | 9/1992 |
| WO | 94/05252 A1 | 3/1994 |
| WO | WO 94/23742 A1 | 10/1994 |
| WO | WO 95/04135 A1 | 2/1995 |
| WO | WO 96/38548 A1 | 12/1996 |
| WO | 97026908 A1 | 7/1997 |
| WO | WO 97/44008 A1 | 11/1997 |
| WO | WO 98/22513 A1 | 5/1998 |
| WO | 99/22597 A1 | 5/1999 |
| WO | 2001028600 A1 | 4/2001 |
| WO | WO 01/41776 A2 | 6/2001 |
| WO | WO 01/45762 A2 | 6/2001 |
| WO | WO 02/00296 A1 | 1/2002 |
| WO | WO 02/30467 A2 | 4/2002 |
| WO | 03/047642 A1 | 6/2003 |
| WO | WO 03/080109 A1 | 10/2003 |
| WO | WO 03/090800 A1 | 11/2003 |
| WO | WO 03/106333 A1 | 12/2003 |
| WO | WO 2004000339 A1 | 12/2003 |
| WO | WO 2004093569 A1 | 11/2004 |
| WO | WO 2004/108176 A1 | 12/2004 |
| WO | WO 2004/108917 A1 | 12/2004 |
| WO | WO 2005/034969 A1 | 4/2005 |
| WO | 2005120250 A1 | 12/2005 |
| WO | WO 2006/133523 A2 | 12/2006 |
| WO | WO 2007/045931 A2 | 4/2007 |
| WO | WO 2007/051599 A1 | 5/2007 |
| WO | 2007/085299 A1 | 8/2007 |
| WO | WO 2007/134180 A1 | 11/2007 |
| WO | WO 2007/137881 A1 | 12/2007 |
| WO | WO 2008/012107 A1 | 1/2008 |
| WO | WO 2008/041218 A1 | 4/2008 |
| WO | WO 2008/049251 A1 | 5/2008 |
| WO | WO 2008/049578 A2 | 5/2008 |
| WO | WO 2008/064272 A2 | 5/2008 |
| WO | WO 2008/103673 A1 | 8/2008 |
| WO | 2009/003960 A1 | 1/2009 |
| WO | 2009009156 A1 | 1/2009 |
| WO | WO 2009/009156 A2 | 1/2009 |
| WO | 2009/064879 A2 | 5/2009 |
| WO | WO 2009/116944 A1 | 9/2009 |
| WO | WO 2009/118379 A1 | 10/2009 |
| WO | WO 2009/137697 A1 | 11/2009 |
| WO | WO 2009/147402 A2 | 12/2009 |
| WO | WO 2010/044042 A1 | 4/2010 |
| WO | WO 2010/0082846 A1 | 7/2010 |
| WO | WO 2010/101844 A1 | 9/2010 |
| WO | WO 2011/028965 A2 | 3/2011 |
| WO | WO 2011/059497 A1 | 5/2011 |
| WO | 2011/068514 A1 | 6/2011 |
| WO | 2011/071904 A2 | 6/2011 |
| WO | 2 359 784 A1 | 8/2011 |
| WO | WO 2011/113436 A1 | 9/2011 |
| WO | WO 2011/126384 A1 | 10/2011 |
| WO | WO 2011/139168 A1 | 11/2011 |
| WO | WO 2012/030231 A1 | 3/2012 |
| WO | WO 2012/052425 A1 | 4/2012 |
| WO | WO 2012/134770 A1 | 10/2012 |
| WO | WO 2012/140272 A1 | 10/2012 |
| WO | WO 2013/008054 A1 | 1/2013 |
| WO | WO 2013/009910 A2 | 1/2013 |
| WO | WO 2013/113906 A1 | 8/2013 |
| WO | 2013/172468 A1 | 11/2013 |
| WO | WO 2014/110580 A1 | 7/2014 |
| WO | WO 2015/030609 A1 | 3/2015 |
| WO | WO 2015/041835 A1 | 3/2015 |
| WO | WO 2015/041836 A1 | 3/2015 |
| WO | WO 2015/074159 A1 | 5/2015 |
| WO | WO 2015/166197 A1 | 11/2015 |
| WO | WO 2015/173002 A1 | 11/2015 |
| WO | WO 2015/173522 A1 | 11/2015 |
| WO | WO 2016/007776 A1 | 1/2016 |
| WO | WO 2016/011498 A1 | 1/2016 |
| WO | 2016/022670 A1 | 2/2016 |
| WO | WO 2016/083798 A1 | 6/2016 |
| WO | WO 2016/123539 A1 | 8/2016 |
| WO | WO 2016/124926 A9 | 8/2016 |
| WO | 2017013448 A1 | 1/2017 |
| WO | 2017/042568 A1 | 3/2017 |
| WO | 2017/071663 A1 | 5/2017 |
| WO | 2017178822 A1 | 10/2017 |
| WO | 2018/029698 A1 | 2/2018 |
| WO | 2018/029705 A1 | 2/2018 |
| WO | 2018029705 A1 | 2/2018 |
| WO | 2018/065608 A1 | 4/2018 |
| WO | 2018/065789 A1 | 4/2018 |

OTHER PUBLICATIONS

Sugii S. "Raw Materials from Honey Bee—Its Present State and Actual Application", Fragrance Journal, (2002), vol. 30, No. 3, pp. 11-16, with English-language Abstract.
Wounds UK 2015 Conference in Harrogate, 2015 Wounds UK Annual Conference, Company Press Releases, (Nov. 9, 2015), 2 pages.
"A patient's perspective on his military and civil post-trauma wound care treatment", Wounds UK, EWMA Special, (2016) pp. 52-55.
Gough, Z et al., "When will we take medicinal honey seriously?", BBC Nature, (Jul. 22, 2014), pp. 1-5.
Behera, B. et al., "Modulating the properties of sunflower oil based novel emulgels using castor oil fatty acid ester: Prospects for topical antimicrobial drug delivery", Colloids and Surfaces B: Biointerfaces, (2015), vol. 128, pp. 155-164.
Cooke, J. et al., "The antimicrobial activity of prototype modified honeys that generate reactive oxygen species (ROS) hydrogen peroxide", BMC Research Notes, (2015), vol. 8, No. 20, pp. 1-5.
Dryden, M. et al., "A multi-centre clinical evaluation of reactive oxygen topical wound gel in 114 wounds", Journal of Wound Care, (Mar. 2016), vol. 25, No. 3, pp. 1-8.
Dryden, M. et al., "Engineered honey: In vitro antimicrobial activity of a novel topical wound care treatment", Journal of Global Antimicrobial Resistance, (Sep. 2014), vol. 2, Issue 3, pp. 168-172.
Dryden, M. et al., "The Use of Surgihoney to prevent or eradicate bacterial colonisation in dressing oncology long vascular lines", Journal of Wound Care, (Jun. 2014), vol. 23, No. 6, pp. 1-4.
Dryden, M et al., "Infection prevention in wounds with Surgihoney", Journal of Hospital Infection, (2014), pp. 1-2.
Masker, R., "Man of steel won't let disability stop him in his tracks", Hampshire Chronicle, (Sep. 30, 2013), 4 pages.
Esposito, S. et al., "Hot topics in the diagnosis and management of skin and soft-tissue infections", International Society of Chemotherapy, (Jul. 2016), vol. 48, Issue 1, pp. 19-26.

(56) References Cited

OTHER PUBLICATIONS

Halstead, F. et al.,"The in vitro antibacterial activity of engineered honey (Surgihoney) against important biofilm-forming burn wound pathogens", Surgical Reconstruction and Microbiology Research Centre, (Nov. 2014), Poster, 1 pages.

Halstead, F. et al.," I he in vitro antibacterial activity of engineered honey (Surgihoney) against important biofilmforming burn wound pathogens ", Surgical Reconstruction Microbiology Research Center (Apr. 25, 2015), Poster, 1 page.

Halstead, F. et al., "In vitro activity of an engineered honey, medical-grade honeys, and antimicrobial wound dressings against biofilm-producing clinical bacterial isolates", The Journal of Wound Care, (Feb. 2016), vol. 25, No. 2, 9 pages.

Masker, R., "Ex-soldier Ben Steele to play 'murderball' for his country", ittp://www.hampshirechronicle.co.uk/news/11468966.Ex_solider_to_play_murderball_for_his_country/?ref-var_0, Sep. 11, 2014, 2 pages.

Dryden, M.S. et al., "Reactive oxygen: a novel antimicrobial mechanism for targeting biofilm-associated infection", Journal of Global Antimicrobial Resistance, (Mar. 2017), vol. 8, pp. 186-191.

Dryden, M. et al., "Hot topics in reactive oxygen therapy: antimicrobial and immunological mechanisms, safety and clinical applications", Journal of Global Antimicrobial Resistance, (Dec. 13, 2016), 25 pages.

Winter, G., "Surgery and honey", http://publishing,rcseng.ac.uk/doi/10/1308/rcsbull.2017.52, (Feb. 2, 2017), 7 pages.

Winter, G. F., "The role of bioengineered honey in wound care", Nursing Practice Review Wound Care, (Dec. 10, 2016), vol. 112, No. 39/40, pp. 15-17.

Ridley, M. et al., "Our brilliant biologists are changing the world", The Times, http://www.thetimes.co.uk/edition/comment/our-brilliant-biologists-are-changin-the- . . . , (Dec. 19, 2016) 19 pages.

Dunnill, C. et al., "Reactive oxygen species (ROS) and wound healing: the functional role of ROS and emerging ROS-modulating technologies for augmentation of the healing process", http://onlinelibrary.wiley.com/doi/10.1111/iwj.12557/full, (Feb. 2017), 12 pages.

Saeed, K. et al., "Prosthetic joints: shining lights on challenging blind spots", IJAA, (2016), 7 pages.

"Roger Backhouse QC hails pioneering honey for fighting bacteria that threatened his life", http://www.hampshirechronicle.co.uk/news/14476095.New_surgical_honey_saves_leg_and_possibly_life_of_Winchester_QC/, (May 6, 2016) 2 pages.

Winter, G., "Healing powers, Bioengineered honey could be promising new agent for healing wounds", Nursing Standard, (Sep. 24, 2014), vol. 29, No. 4, p. 23.

Winter, G., "The bee's knees for wounds and infections", http://irishtimes.com/life-and-style/health-family/the-bees-knees-for-wounds-and-infections-1/2709843, (Jul. 5, 2016), 2 pages.

Masker, R., "Why 'super honey' is the bees' knees for wounds and infections", theguardian.com, (Jan. 1, 2014), 3 pages.

Khan, W. et al., "Debridement: Defing something we all do", Journal of Trauma and Orthopaedics, (Mar. 2016), vol. 4, Issue 1, pp. 48-50.

Lipsky, B.A. et al., "Antimicrobial stewardship in wound care: a Position Paper from the British Society for Antimicrobial Chemotherapy and European Wound Management Association", J Antimicrob Chemother, (Jul. 2016), vol. 71, pp. 3026-3035.

Longevity Bulletin: From the Institute and Faculty of Actuaries, "Antimicrobial resistance", (May 2016), Issue 8, 14 pages.

Dryden, M., "Reactive Oxygen—a solution for healing and antimicrobial resistance?", Royal Hampshire Country Hospital, Winchester, (2015), 35 pages.

Arnold, S., "'Miracle' honey that can prevent limb amputation with bacteria-killing properties", http://www.mirror.co.uk/science/miracle-honey-can-prevent-limb-7833500, (Apr. 25, 2016), 4 pages.

Salamat, A.A. et al., "Surgihoney Treatment of CRS-Associated *S. aureus* Biofilms", University of Southhamptom, NHS, (Jan. 9, 2015), 16 pages.

Hoiby, N. et al., "ESCMID guidline for the diagnosis and treatment of biofilm infections 2014", Olin Microbiol Infect, (2015), vol. 21, pp. 1-25.

"Politics First—Reactive Oxygen highlighted as potential breakthrough in battle against superbugs", Company Press Releases, (Jan. 10, 2017), 6 pages.

Matoke Holdings Ltd, "RCT pilot study to compare Surgihoney RO with a conventional dressing in the treatment of bi-lateral vascular leg ulcers", Matoke Holdings LTD, (Oct. 4, 2016), 3 pages.

"Reactive Oxygen: a new solution to antimicrobial resistance", Article reprinted from the British Journal of Nursing, (2016), vol. 25, No. 12, Tissue Viability Supplement, 2 pages.

"Reactive oxygen E-newsletter" (Jul. 2016) 4 pages.

"Reactive oxygen E-newsletter" (Jun. 2016) 5 pages.

"Reactive oxygen E-newsletter" (Nov. 2016) 6 pages.

"Reactive oxygen E-newsletter" (Oct. 2016) 5 pages.

"Reactive Oxygen highlighted in House of Lords as a new solution in fight against antibiotic resistance", Matoke Holdings LTD, (Sep. 15, 2016) 4 pages.

"Reactive oxygen E-newsletter" (Jan. 2017) 7 pages.

"Reactive Oxygen under the spotlight in House of Commons", Matoke Holdings LTD, (Jul. 5, 2016), 4 pages.

"Reactive Oxygen (RO): Transforming wound care & Infection Control in An Age of Antimicrobial Resistance", Wednesday, Apr. 13, 2016, Elgar Concert Hall, Bramall Music Building, University of Birmingham, 90 pages.

"Research project: Evaluation of the role of bacterial biofilms in the pathophysiology of chronic rhinosinusitis", Centre for Biological Sciences, http://www.southampton.ac.uk/biosci/research/projects/role_of_bactenal_biofilms_in . . . , (May 5, 2015), 1 page.

"International Journal of Antimicrobial Agents—Prosthetic joints: shining light on challenging blind spots", http://www.ijaaonline.com/article/S0924-8579(16)30351-X/asbtract, (Dec. 8, 2016), 4 pages.

Suebsaeng, A. et al., "Necrotising Fasciitis with Multi-Drug Resistant Colonisers", Royal Hampshire Country Hospital, (Oct. 6, 2016), 1 page.

Mandal, M.D. et al., "Honey: its medicinal property and antibacterial activity", Asian Pac J Trop Biomed, (2011), 1(2): 154-160.

Elliot, V., "Doctors discover "super honey" with amazing power to treat soldiers' wounds and kill superbug infections", MailOnline, Aug. 10, 2013, 2 pages.

Japanese Notice of Reasons for Rejection dated Dec. 26, 2017 received in Japanese Patent Application No. 2016-565373, together with an English-language translation.

Zohdi, R.M., et al., "Gelam (*Melaleuca* spp.) Honey-Based Hydrogel as Burn Wound Dressing", Evidence-Based Complementary and Alternative Medicine, Jan. 1, 2012, vol. 2012, pp. 1-7.

"Gamma Ray", Wikipedia, URL: https://en.wikipedia.org/w/index.php?title=Gamma_ray&oldid=740638875, Sep. 22, 2016, 16 pages.

United States Office Action dated Feb. 8, 2019 issued in U.S. Appl. No. 15/307,564.

Bang L.M. et al., "The Effect of Dilution on the Rate of Hydrogen Peroxide Production in Honey and Its Implications tor Wound Healing", The Journal of Alternative and Complementary Medicine, (2003), vol. 9, No. 2, pp. 267-273.

Kretavicius J. et al., "Inactivation of glucose oxidase during heat-treatment de-crystallization of honey", Agriculture, (2010), vol. 97, pp. 115-122.

Clarke, L., "The evaluation of SurgihoneyRO™ in the treatment of chronic wounds with suspected biofilms", Brentwood Community Hospital, 2018 (Poster).

Cooke, J. et al., "The antimicrobial activity of prototype modified honeys that generate reactive oxygen species (ROS) hydrogen peroxide", BMC Research Notes, 2015, 8:20, pp. 1-5.

Davies, L., et al., "Multi-Species Biofilm Disruption by Two Wound Care Products Using a Colony Drip Flow Model", 2018 (Poster).

Dryden, M., "Reactive oxygen species: a novel antimicrobial", International Journal of Antimicrobial Agents, Mar. 2018, 51(3):299-303.

Dryden, M., "Reactive-oxygen-made-easy wounds", Wounds UK, Nov. 2018, vol. 14, issue 5, pp. 1-6.

(56) References Cited

OTHER PUBLICATIONS

Dryden, M. et al., "Hot Topics in Reactive Oxygen therapy: Antimicrobial and immunological mechanisms, safety and clinical applications", Mar. 2017, Journal of Global Antimicrobial Resistance, vol. 8, pp. 194-198.
Dryden, M., "Reactive oxygen therapy a novel therapy in soft tissue infection", Current Opinion in Infectious Diseases, Apr. 2017, vol. 30, issue 2, pp. 143-149.
Dryden, M., "Reactive oxygen species treatment in the management of wounds", Wounds UK, 2017, vol. 13, No. 2, pp. 26-33.
Dunnill, C. et al., "Reactive oxygen species (ROS) and wound healing: the functional role of ROS and emerging ROS-modulating technologies for augmentation of the healing process", International Wound Journal, 2015, pp. 89-96.
Filipini, R., "H2O2 (SurgihoneyRO™)—Fast healing autolytic debridement and healing in long standing infected chronic wounds", Guy's & St Thomas' NHS Foundation Trust, 2019 (Poster).
Hall, T.J. et al., "Antimicrobial emulsions: Formulation of a triggered release reactive oxygendelivery system," Materials Science & Engineering C 103 (2019) 1009735.
Halstead, F.D. et al., "Use of an engineered honey to eradicate pre-formed biofilms of important wound pathogens an in vitro study", Journal of Wound Care, Jul. 2016, vol. 26, No. 7, pp. 1-8.
Halstead, F.D.,"Antibiotic-sparing wound gel shows real promise in fighting biofilm infection", SurgihoneyRO, Nov. 17, 2017, 4 pgs.
Hudgell, L. et al., "Improving healing of challenging wounds with SurgihoneyRO™—a novel antimicrobial wound gel with antibiofilm action in vitro", Nov. 15, 2017, The WOUND Clinic (Poster).
Khan, W. et al., "Surgihoney as a Novel Antimicrobial Coating in Salvage Revision Total Knee Arthoplasty", Feb. 21, 2018, Orthopaedicproceedings, vol. 97-B, No. SUPP_15, 2 pgs.
Matoke Holdings Ltd., "Doctor treats remote tribe in Papua, Indonesian New Guinea", Jan. 30, 2017, 3 pgs.
Matoke Holdings Ltd., "Reactive Oxygen® research wins prestigious innovation award", Apr. 4, 2017, 4 pgs.
Matoke Holdings Ltd., "Pilot study on impact of SurgihoneyRO™ in preventing surgical site infection", Reactive Oxygen, Mar. 22, 2017, 3 pgs.
Miravittles, M. et al., "Chronic Respiratory Infection in Patients with Chronic Obstructive Pulmonary Disease: What Is the Role of Antibiotics?", International Journal of Molecular Science, 2017,18(7), 1344, pp. 1-12.
Newby, R.S. et al., "Antimicrobial activity of a novel bioengineered honey against non-typeable Haemophilus influenzae biofilms: an in vitro study", BMJ Journals, 2018, 2 pgs.
Papadopoulou, D. et al., "Evaluation of a bio-engineered honey and its synthetic equivalent as novel *Staphylococcus aureus* biofilm-targeted topical therapies in chronic rhinosinusitis", Am J Rhinol Allergy, Jan. 2020, 34 (1)80-86.
Parker, S. et al., "Impact of Surgihoney Reactive Oxygen on surgical site infection (SSI) after complex abdominal wall reconstruction (AWR) of grade 3 and 4 ventral Hernias: A single arm pilot study", International Journal of Surgery Protocols 5 (2017) pp. 18-21.
Public Health England, "Summary of antimicrobial prescribing guidance—managing common infections", Oct. 2018, pp. 1-107.
Public Health England, SurgihoneyRO, "SurgihoneyRO™ officially recognised by NHS through Public Health England. (PHE) guidance for common infections", Oct. 2, 2017, 2 pgs.
Thomas, H. et al., "Treatment of World Health Organisation priority pathogens using an antimicrobial wound gel", Perfectus Biomed, 2018, (Poster).
Winter, G., "Surgery and Honey, Can this well-established natural remedy for wound infection reduce our reliance on antibiotics?", Feb. 2017, vol. 99 issue 2, pp. 52-55.
Winter, G., "Prudent antibiotic stewardship in wound care management", British Journal of Healthcare Management, 2018, vol. 24, No. 4, pp. 170-171.
English-language translation of Japanese Office Action dated Feb. 4, 2019 issued in JP Patent Application No. 2016-565373.
U.S. Office Action dated Feb. 26, 2019 issued in U.S. Appl. No. 15/528,969.
Al-Waili N.S. et al., "Honey and Microbial Infections: A Review Supporting the Use of Honey for Microbial Control", Journal of Medicinal Food, (2011), 14(10), pp. 1079-1096.
Australian Office Action dated Jun. 25, 2018 issued in corresponding Australian Patent Application No. 2014393037.
International Search Report and Written Opinion of International Searching Authority dated Oct. 14, 2016 issued in PCT/GB2016/052258.
"Dr Beryl Oppenheim", https://www.youtube.com/watch?v=cO-LJ03ntfQ, Apr. 26, 2016, 2 pages.
"Prof Malcolm Richardson", https://www.youtube.com/watch?v=8UqT_STg9Hg, Apr. 26, 2016, 2 pages.
Jull AB et al.I, "Honey as a Tropical Treatment for Wounds", The Cochrane Library, 81 pages (Feb. 28, 2013).
Kwakman, P.H.S. et al., "Antibacterial Components of Honey", IUBMB Life 64(1) 48-55 (Jan. 2012).
European Communication dated Sep. 12, 2017 received in European Patent Application No. 14 728 599.3.
European Communication dated Aug. 28, 2017 received in European Patent Application No. 17 18 1068.2.
"Effects of Surgihoney and its effectiveness against infections found in soft tissue wounds, including multi resistant bacteria like MRSA and *E-coli*" info@reactiveoxygen,co.uk, BBC South Today, Aug. 20, 2013, 1 page.
"SurgihoneyRO & Sinusitis" info@reactiveoxygen.co.uk, Medical Independent, May 27, 2016, 1 page.
"SurgihoneyTM showcased in Science Museum in London" info@reactiveoxygen.co.uk, Company Press Relases, Jul. 10, 2014, 2 pages.
Molan, P.C., "The antibacterial activity of honey", The nature of the antibacterial activity. Bee world, bee research association. vol. 1-2, Jan. 1, 1992 pp. 5-29.
"Nijhuis: Medihoney barrier cream", Nov. 15, 2013 XP055305245, 24 pages.
Davis, P. et al., "Oxygen, and its Role in Wound Healing: A Literature Review" Archimed, Bedford, May 2007, 7 pages.
"Michael Clough and Claire Stephens", https://www.youtube.com/watch?v=aDBBDVIjJ3w, Apr. 26, 2016, 2 pages.
"Dr Jill Brooks", https://www.youtube.com/watch?v=R2jFFuJPYoY, Apr. 26, 2016, 2 pages.
"Prof Jonathan Cooke", https://www.youtube.com/watch?v=r5eL0aLWJjo, Apr. 26, 2016, 2 pages.
"Dr Matthew Dryden", https://www.youtube.com/watch?v=f2E-S2nHTd0, Apr. 26, 2016, 2 pages.
Cimolai, N., "Sweet success? Honey as a topical wound dressing", BC Medical Journal, 49(2):64-67 (2007).
Furrer, P., "The central role of excipients in drug formulation", European Pharmaceutical Review, p. 1-10, Apr. 18, 2013.
Zhu, Y, et al, "Practical Clinical Pharmacy of Traditional Chinese Medicine", Shanxi Science Technology Press, pp. 401-450, Jul. 2013, with English Translation of Portions of Reference.
Combined Search and Examination Report under Sections 17 and 18(3) dated Aug. 20, 2019 received in Great Britain Patent Application No. GB1908998.6.
Summons to attend oral proceedings pursuant to Rule 115(1) EPC dated Sep. 26, 2019, received in European Patent Application No. 16745142.6.
Summons to attend oral proceedings pursuant to Rule 115(1) EPC dated Jul. 5, 2019, received in European Patent Application No. 16711333.1.
Examination report under sections 12 & 13 of the Patents Act, 1970 and Patent Rules, 2003, dated Nov. 15, 2019, received in Indian Patent Application No. 201717030372.
Extended European Search Report dated Nov. 22, 2019, received in European Patent Application No. 19173943.2.
English Translation of Third Notification of Office Action dated Sep. 29, 2019, received in Chinese Patent Application No. 201480080307.5.
United States Final Office Action dated Sep. 13, 2019, received in U.S. Appl. No. 15/528,969.

(56) References Cited

OTHER PUBLICATIONS

United States Final Office Action dated Sep. 19, 2019, received in U.S. Appl. No. 15/307,564.
GB Office Action dated Aug. 3, 2018 issued in GB Patent Application No. GB1707057.4.
International Search Report and Written Opinion dated Jan. 3, 2019 issued in PCT/GB2018/052976.
International Search Report and Written Opinion dated Jan. 3, 2019 issued in PCT/GB2018/052977.
Australian Office Action dated Jan. 16, 2019 issued in Australian Patent Application No. 2014393037.
Ruhl S. et al., "Integrity of Proteins in Human Saliva after Sterilization by Gamma Irradiation", Applied and Environmental Microbiology, (2011), vol. 77, No. 3, pp. 749-755.
Dryden M. et al., "Engineered Honey to Manage Bacterial Bioburden and Biofilm in Chronic Wounds", EWMA Free Paper Session: Infection and Antimicrobials (2015), 3 pages.
Masker, R., "Honey has golden touch in helping beat bacteria at Royal Hampshire Country Hospital", Hampshire Chronicle, (Jul. 11, 2013), 2 pages.
NeilMed Pharmaceuticals—Sinus Rinse Isotonic, http://www.neilmed.com/uk/sinusrinse_isotonic/php, (May 14, 2015), 2 pages.
Lyczak, J.B. et al., "Lung Infections Associated with Cystic Fibrosis", Clinical Microbiology Reviews, (Apr. 2002), vol. 15, No. 2, pp. 194-222.
Sun, F. et al., "Antibiotic Resistance and Novel Therapeutic Strategies", Biofilm-Associated Infections, www.medscape.com, (2013), 8(7):877-886.
"Biofilm bacteria", The Marshall Protocol Knowledge Base, http://mpkb.org/home/pathogenesis/microbiota/biofilm, (May 5, 2015), 6 pages.
Suh, J.D. et al., "Treatment Options for Chronic Rhinosinusitis", Proceedings of the American Thoracic Society, (2011), vol. 8, pp. 132-140.
Cooke, J. et al., "When antibiotics can be avoided in skin inflammation and bacterial colonization: a review of topical treatments", www.co-infectiousdiseases.com, (Apr. 2014), vol. 27, No. 2, pp. 125-129.
Dryden, M. et al., "Using antimicrobial Surgihoney to prevent caesarean wound infection", British Journal of Midwifery, (Jan. 2014), vol. 22, No. 11, pp. 23-27.
Dryden, M. et al., "Surgihoney—Modified honey wound treatment: first report of in vitro activity and early clinical evaluation", Hampshire Hospitals, NHS Foundation, (2013), 1 page.
Heyes, I. et al., "Surgihoney: Biotechnological honey wound treatment: first clinical report of its use in the tropics", Surgihoney, (2013), 1 page.
Simon, A. et al., "Medical Honey for Wound Care-Still the 'Latest Resort'?", eCAM, (2009), 6(2)165-173.
Saha, D. et al., "Hydrocolloids as thickening and gelling agents in food: a critical review", J Food Sci Technol, (Nov.-Dec. 2010), 47(6):587-597.
Doria, A. et al., "Autoinflammation and autoimmunity: Bridging the divide", Autoimmunity Reviews, (2012), vol. 12, pp. 22-30.
Manes, R.P. et al., "Etiology, Diagnosis and Management of Chronic Rhinosinusitis", Expert Rev Anti Infect Ther., (2013), 11(1):25-35.
Gain, R.B. et al., "Update on the management of chronic rhinosinusitis", Infection and Drug Resistance, (Jan. 22, 2013), 6: 1-14.
Weston, R.J., "The contribution of catalase and other natural products to the antibacterial activity of honey: a review", Food Chemistry, (2000), vol. 71, pp. 235-239.
Haynes, J.S. et al., "Properties of honey: its mode of action and clinical outcomes," Wounds uk, (2011), vol. 7, No. 1, pp. 50-57.
White, J.W. et al., "The Identification of Inhibine, The Antibacterial Factor in Honey, as Hydrogen Peroxide and Its Origin in a Honey Glucose-Oxidase System", Biochimica et Biophysica Acta, (1963), vol. 73, pp. 57-70.
Jeffrey, A.E. et al., "Medical uses of honey.", Rev Biomed, (1996), 7:43-49.

Matoke Holdings, "Surgihoney Reactive Oxygen helping patients in the developing world", Reactive Oxygen, (Jul. 25, 2016), 4 pages.
Matoke Holdings, "SurgihoneyRO and Reactive Oxygen hailed as a 'British breakthrough that could be of enormous significance', in fight against antimicrobial resistance by leading science writer", Reactive Oxygen, (Dec. 19, 2016), 2 pages.
"Surgihoney RO Featured at Wound Care Conference", Company Press Releases, (Jan. 26, 2016), 2 pages.
"Surgihoney in prestigious International Wound Journal", Company Press Releases, (Jan. 6, 2016), 4 pages.
Winter, G. et al., "A sniff of sinutis", themedicalindependent, mindo.ie, (May 19, 2016) p. 28.
Dryden, M., "Reactive oxygen therapy: a novel therapy in soft tissue infection", www.co-infectiousdiseases.com, (2017), vol. 29, pp. 1-7.
"Honey's Potential to Save Lives by Destroying Harmful Fungus", http://www.dddmag.com/news/2016/02/honeys-potential-save-lives-destroying-harmful-fungus, University of Manchester, (Sep. 2, 2016), 3 pages.
"Could honey combat respiratory disease?", http://www.southhampton.ac.uk/news/2016/04/surgihoney.page, University of Southhampton, (Apr. 29, 2016), 3 pages.
"University of Southhampton investigates potential benefits of Surgihoney in treating chronic rhinosinusitis", Company Press Releases, (Jan. 5, 2016), 4 pages.
Matoke Holdings Ltd, "University Researchers joining forces with British biotech business to tackle global threat of antibiotic resistance", Reactive Oxygen, (Sep. 22, 2016), 3 pages.
Williams, R.L. et al., "Honey as a Novel Antimicrobial Coating in Salvage Revision Total Knee Arthroplasty", European Bone & Joint Infection Society in Lisbon, (2016), Poster, 1 page.
"Woundcare4Heroes conference", Company Press Releases, (Aug. 1, 2015), 1 page.
Kwakman, P. H. S et al., "Two Major Medicinal Honeys Have Different Mechanisms of Bactericidal Activity", PLoS ONE, (Mar. 2011), vol. 6, Issue 3, pp. 1-8.
European Search Report dated Aug. 28, 2017 issued in EP 17181068.2.
Minden-Birkenmaier, B. A. et al., "Preliminary investigation and Characterization of Electrospun Polycaprolactone and Manuka Honey Scaffolds for Dermal Repair", Journal of Engineered Fibers and Farbrics, (2015), vol. 10, Issue 4, pp. 126-138.
Kanani, A.G. et al., "Effect of Changing Solvents on Poly(E-Caprolactone) Nanofibrious Webs Morphology", Journal of Nanomaterials, (2011), 11 pages.
Liverani, L. et al., "Electrospinning with benign solvents: feasibility study and versatile use of poly(epsilon-caprolactone) fibers", (Mar. 30, 2016), 2 pages.
Mele, E. et al., "Electrospinning of natural polymers for advanced wound care: towards responsive and adaptive dressings", J Mater Chem B, (2016), vol. 4, pp. 4801-4812.
Andreu, V. et al., "Smart Dressings Based on Nanostructured Fibers Containing Natural Origin Antimicrobial, Anti-Inflammatory, and Regenerative Compounds", Materials, (2015), vol. 8, pp. 5154-5193.
Written Opinion of The International Searching Authortiy dated Jun. 16, 2017 issued in PCT/GB2017/051033.
Combined Search and Examination Report dated Jul. 10, 2017 issued in GB1709530.8.
GB Search Report dated Dec. 16, 2010 issued in GB1013150.6.
New Zealand Examination Report dated Aug. 17, 2010 issued in NZ 587355.
New Zealand Examination Report dated Jun. 7, 2011 issued in NZ 587355.
International Search Report dated Jun. 21, 2013 issued in PCT/GB2012/052693.
GB Examination Report dated Nov. 1, 2016 issued in GB 1608422.0.
GB Examination Report dated Jul. 18, 2016 issued in GB 1608422.0.
Combined Search and Examination Report dated Nov. 1, 2016 issued in GB 1613597.2.

(56) References Cited

OTHER PUBLICATIONS

International Search Report dated Aug. 12, 2014 issued in PCT/GB2014/051337.
International Search Report dated Jan. 29, 2016 issued in PCT/GB2015/053584.
International Search Report and Written Opinion dated Jun. 2, 2016 issued in PCT/GB2016/050253.
GB Office Action dated Oct. 17, 2018 issued in corresponding GB Application No. 1707057.4.
Lu J. et al. "The Effect of New Zealand Kanuka, Manuka and Clover Honeys on Bacterial Growth Dynamics and Cellular Morphology Varies According to the Species", PLoS ONE, (2013), 8(2): e55898.
Morgulis, S., "Studies of the Inactivation of Catalase", Journal of Biological Chemistry, vol. 86, pp. 75-85, (1930).
Nijhuis, W.A. et al., "A Randomised Trial of Honey Barrier Cream versus Zinc Oxide Ointment", British Journal of Nursing, 21(20), S23-24, 27-28 (2012).
Xie, H., "Antibacterial Properties of Honey and its Application in Medicine", Strait Pharmaceutical Journal, vol. 16, No. 4 (Aug. 30, 2004), with English language abstract.
Chinese Office Action dated Mar. 3, 2020 in Chinese Patent Application No. 201680020338.0, together with an English language translation.
U.S. Office Action dated Jun. 23, 2020 received in U.S. Appl. No. 15/307,564.
Artemuk E.G. et al., "Institution of Education", Fermenty, pp. 7-15 (2010), together with an English-language translation.
Davydova M.E. et al., "Stability and Catalytic Properties-Glucosooxidase from Penicillium Funiculosum G-15", Lomonosov Moscow State University, Biological Faculty, vol. 43(6), pp. 366-370 (2002), together with an English-language translation.
Sagona S. et al., "Preliminary Evaluation of Glucose Oxidase and its Products In Vitro Antimicrobial Activities on Paenibacillus Larvae ATCC9545 Vegetative Form", Bulletin of Insectology 68(2):233-237 (2015).
Tyzhigirova V.V., "Quality Indicators and Features Analysis of Solutions", Handbook, Irkutsk, MGMU, pp. 5-15 (2016), together with an English-language translation.
Timmons, J., "Oxyzyme(TM) sterile wound dressing: a new concept for wound healing", Wounds UK, Jan. 1, 2007, 15 pages.

a)

b)

a)

b)

c)

a)

b)

a)

b)

a)

b)

c)

d)

e)

f)

a)

b)

a)

b)

a)

b)

c)

a)

b)

c)

a)

b)

c)

d)

a)

b)

a)

b)

a)

b)

a)

b)

c)

d)

e)

f)

g)

h)

ANTIMICROBIAL COMPOSITIONS

This invention relates to compositions, particularly storage-stable compositions, for generating antimicrobial activity, antimicrobial compositions and solutions, use of the compositions and solutions, particularly for wound healing, and methods for their production.

Honey has been used for treatment of microbial infections since ancient times. In recent years there has been a resurgence of interest in the therapeutic efficacy of honey, particularly in the area of wound healing. Clinical trials have shown that honey is an effective broad-spectrum antimicrobial agent which is effective against common wound-infecting organisms, such as *Pseudomonas aeruginosa, Staphylococcus aureus, Candida albicans* and *Escherichia coli*, and is effective against antibiotic-resistant strains of bacteria. As a natural product, honey also offers an attractive alternative to drug-based treatments.

Many different types of honey have antimicrobial activity. This activity is attributed largely to osmolarity, pH, hydrogen peroxide production and the presence of phytochemical components. Manuka honey, which originates from the Manuka tree (*Leptospermum scoparium*), has been recognised to have superior antimicrobial activity, compared to most other honeys, due to the high levels of antibacterial phytochemical activity present in this type of honey. However, manuka honey is in relatively limited supply and cannot meet the demands of a global market.

In addition to its antimicrobial action, several other activities of honey are believed to assist in wound healing, particularly healing of chronic wounds. In particular, honey has an ability to autolytically debride and deodorise wounds. Debridement is the removal of dead, damaged or infected tissue to improve the healing potential of the remaining healthy tissue. Honey has also been reported to have anti-inflammatory properties, to be able to stimulate tissue growth, and to manage pain and minimise scarring.

Several honey-based wound care dressings are currently available on the market. Many of these use manuka honey, or other honey with a high level of non-peroxide antibacterial activity, because the acidity, catalase activity, and protein-digesting enzymes present in wound fluids can reduce the antibacterial effectiveness of hydrogen peroxide.

Currently marketed honey-based dressings include the Medihoney range of products, manufactured by Comvita/Derma Sciences, which contain manuka honey, and Activon, a pure manuka honey with no additives, manufactured by Advancis. Other honey-based dressings contain honey and one or more additional ingredients. These include Melladerm Plus, which is an antibacterial wound gel made by SanoMed. The gel contains honey from a multiflower mountain region in Bulgaria that has a naturally high glucose oxidase and phenolic content (the main phytochemical components in honey are phenolic compounds). During processing, the honey is not heated or irradiated because this is considered to destroy its healing properties, in particular the production of hydrogen peroxide by glucose oxidase. It is instead sterilized using an ozonation method, described in WO 2008/049578, in which ozone gas is bubbled through liquefied honey in an ozone-resistant container. However, ozone has been approved by the US Food and Drug Administration (FDA) as a sterilant only for reusable medical devices, and so is not currently authorised by the US FDA for sterilisation of honey-based products for use in wound healing.

The Mesitran range is a further range of honey-enriched wound care products. L-Mesitran ointment, manufactured by Triticum, contains 48% medical grade honey, and several other components, including lanolin, sunflower oil, cod liver oil, marigold, Aloe vera, Vitamins C and E, and zinc oxide.

The difference in antimicrobial potency among honeys can be more than one hundred-fold, depending on the geographical, seasonal and botanical source of the honey, as well as the harvesting, processing and storage conditions. Honey-based dressings, therefore, have varying antimicrobial efficacy depending on the type of honey used. A study authored by Jenkins, Burton, and Cooper ("The determination of antimicrobial activity of three honey impregnated wound dressings by challenge test with EMRSA-15", Advancis) found that honey-based dressings containing Activon, Medihoney, or Mesitran product all had differing efficacies against EMRSA-15. The Activon impregnated dressing was the most effective, followed by the Medihoney dressing, with the Mesitran product having a much reduced effect.

There is, therefore, a need to reduce variability in the antimicrobial potency of honeys, and to improve the antimicrobial activity of honeys with low antimicrobial potency. It is also desirable to provide effective honey-based wound care products that do not rely on use of honeys with high levels of phytochemical components. It is also desirable to provide effective honey-based wound care products that have not been sterilised by ozonation.

Several other anti-bacterial wound care dressings are available that do not include honey. These include silver-containing dressings, such as ConvaTec's Aquacel® Ag dressing, which releases ionic silver in a controlled manner as wound exudate is absorbed into the dressing. However, silver-resistant organisms, such as *Staphylococcus aureus, Pseudomonas aeruginosa* and *enterococci*, have been reported, and may contribute to indolence in wound healing.

Povidone-iodine (PVP-I) is a stable chemical complex of polyvinylpyrrolidone (povidone, PVP) and elemental iodine. It is a broad spectrum antiseptic for topical application in the treatment and prevention of infection in wounds. It has been demonstrated that bacteria do not develop resistance to PVP-I. Since 1994 PVP-I has been approved by the US FDA for the first aid treatment of small, acute wounds. However, there has been some controversy over its safety and efficacy, and it was not recommended for use with pressure ulcers by the US Department of Health & Human Services.

Chlorhexidine has rapid, bactericidal activity against a wide spectrum of non-sporing bacteria. Antibacterial activity against *Staphylococcus aureus, Pseudomonas aeruginosa* and a range of clinical isolates has been documented. However, Methicillin-resistant *Staphylococcus aureus* (MRSA) has been observed to be resistant to chlorhexidine. In the UK, the Medicines and Healthcare Products Regulatory Agency (MHRA) has also issued a patient safety alert on the risk of anaphylactic reactions from the use of medical devices and medicinal products containing chlorhexidine.

There is also a need, therefore, to provide anti-microbial wound care products with broad-spectrum activity that are non-toxic, and which can be used for the treatment of chronic wounds.

The applicant has appreciated that the antimicrobial activity of honey depends on a delicate inter-relationship between natural inhibitors and activators, and has developed compositions in which the natural antimicrobial activity of honey can be released with reduced variability between different types and harvests of honey, and in which the antimicrobial properties of honeys with poor antimicrobial potency can be improved. The applicant has also found that such compositions have remarkable wound healing properties, even following sterilisation by exposure to gamma irradiation. The applicant has appreciated that these findings also have application to other natural substances.

The Applicant has found that the antimicrobial potency of the compositions can be precisely enhanced and controlled over a wide range. This makes it possible to provide compositions with antimicrobial potency that is most suited to the intended use.

In its broadest sense, the invention provides a composition for generating anti-microbial activity, which comprises an enzyme that is able to convert a substrate to release hydrogen peroxide, and a substance that includes a substrate for the enzyme. The enzyme is additional (i.e. added as a result of human intervention) to any enzyme activity able to convert the substrate to release hydrogen peroxide (referred to herein as "substrate conversion activity") that may be present in the substance. Preferably the composition is a storage-stable composition which does not include sufficient free water to allow the enzyme to convert the substrate.

According to the invention there is provided a storage-stable composition for generating antimicrobial activity, which comprises: a purified enzyme that is able to convert a substrate to release hydrogen peroxide; and a substance that includes a substrate for the enzyme; wherein the composition does not include sufficient free water to allow the enzyme to convert the substrate.

According to the invention there is also provided a method for producing a storage-stable composition for generating antimicrobial activity, which comprises: contacting a purified enzyme that is able to convert a substrate to release hydrogen peroxide with a substance that includes a substrate for the enzyme, wherein the composition does not include sufficient free water to allow the enzyme to convert the substrate.

According to the invention there is further provided a storage-stable composition for generating antimicrobial activity, which comprises: an enzyme that is able to convert a substrate to release hydrogen peroxide; and a substance that lacks catalase activity and that includes a substrate for the enzyme; wherein the composition does not include sufficient free water to allow the enzyme to convert the substrate.

According to the invention there is also provided a method for producing a storage-stable composition for generating antimicrobial activity, which comprises: contacting an enzyme that is able to convert a substrate to release hydrogen peroxide with a substance that lacks catalase activity and that includes a substrate for the enzyme, wherein the composition does not include sufficient free water to allow the enzyme to convert the substrate.

In the presence of sufficient water, the enzyme of the storage-stable composition is able to convert the substrate and release hydrogen peroxide. Hydrogen peroxide is known to be effective against a wide variety of different microbes. Thus, antimicrobial activity is generated following dilution of a storage-stable composition of the invention.

According to the invention there is also provided a method for producing an antimicrobial composition or solution, which comprises diluting a storage-stable composition of the invention with sufficient water to allow the enzyme to convert the substrate and release hydrogen peroxide.

According to the invention there is further provided an antimicrobial composition or solution, which comprises a storage-stable composition of the invention diluted with sufficient water to allow release of hydrogen peroxide by conversion of the substrate by the enzyme.

Catalase is an enzyme that catalyses the decomposition of hydrogen peroxide to water and oxygen. The use of a substance that lacks catalase activity means that there is no variability in the amount of this activity between similar substances from different sources, or from different harvests from the same source. This reduces the variability in antimicrobial activity that can be generated from such substances. Alternatively, if the substance does include catalase activity, and it is not possible or desirable to inactivate the catalase activity in the substance prior to contacting the substance with the enzyme, then sufficient enzyme may be used such that the effect of catalase activity on the hydrogen peroxide that can be generated from the substance is reduced. This also reduces the variability in antimicrobial activity that can be generated from the substance. In some embodiments it is preferred that the substance lacks catalase activity.

Catalase is present in many plants and animals. Catalase activity may be removed during processing or extraction of the substance, or inactivated before use of the substance in a composition of the invention. Catalase activity may be heat inactivated, for example by pasteurisation. A suitable temperature for heat inactivation of catalase activity is at least 60° C., 70° C., or 80° C., preferably for at least 2 minutes.

The term "storage-stable" is used herein to mean that the composition can be stored at ambient temperature for at least several days, preferably at least a week, more preferably at least one or two months, whilst retaining the ability to generate antimicrobial activity following dilution of the composition. A preferred storage temperature is below 37° C., preferably 20-25° C. Preferably compositions are stored away from exposure to light.

Hydrogen peroxide is generally unstable at ambient temperature. The lack of sufficient free water in a storage-stable composition of the invention prevents the enzyme converting the substrate to release hydrogen peroxide, and thus helps to maintain the stability of the composition for extended periods at ambient temperature. A storage-stable composition of the invention may include some water provided that there is not sufficient free water to allow the enzyme to convert the substrate. Suitable amounts of water will vary depending on the precise components of the composition. However, typically, a storage-stable composition of the invention preferably comprises less than 20% total water content, for example, 10%-19%, water.

Hydrogen peroxide may be released for a sustained period following dilution of a composition of the invention, depending on the amount of substrate present in the composition, and the activity of the enzyme. It will be appreciated that the amount of substrate and/or the activity of enzyme in the composition may be selected to provide for release of a relatively high level of hydrogen peroxide for a short period, or for release of a lower level of hydrogen peroxide for a longer period, following dilution of the composition. Preferably the composition provides for sustained release of hydrogen peroxide for a period of at least twenty four hours, more preferably at least forty eight hours, following dilution of the composition. Preferably the composition provides for sustained release of hydrogen peroxide at a level of less than 2 mmol/litre for a period of at least twenty four hours, following dilution of the composition.

The enzyme present in a composition of the invention is additional to any enzyme activity able to convert the substrate to release hydrogen peroxide (referred to herein as "substrate conversion activity") that may be present in the substance, i.e. compositions of the invention comprise the substance and added enzyme. In some embodiments it is preferred that there is no substrate conversion activity in the substance.

It will be appreciated that there should be sufficient enzyme present in a storage-stable composition of the invention to convert the substrate and form hydrogen peroxide as needed following dilution of the composition.

In view of the importance of generation of hydrogen peroxide by storage-stable compositions of the invention in the presence of sufficient water, it will be appreciated that compositions of the invention should not contain any added peroxidase.

Preferably the enzyme is a purified enzyme. The term "purified enzyme" is used herein to include an enzyme preparation in which the enzyme has been separated from at least some of the impurities originally present when the enzyme was produced. Preferably impurities that have been removed or reduced include those that would otherwise interfere with the ability of the enzyme to convert the substrate to release hydrogen peroxide.

It may not always be necessary or desirable that the purified enzyme is at a high level of purity provided that the enzyme is able to convert the substrate to release hydrogen peroxide. In some circumstances, it may be desirable to used a relatively crude enzyme preparation. Examples of suitable purity levels include at least 10%, 20%, 30%, 40%, 50%, 60%, 70%, 80%, or 90% pure.

It is preferred, however, that the amount of any catalase that may originally have been present when the enzyme was produced has been reduced. The enzyme may have been produced by recombinant or non-recombinant means, and may be a recombinant or non-recombinant enzyme. The enzyme may be purified from a microbial source, preferably from a non genetically modified microbe.

The level of purity of the enzyme may be selected as appropriate depending on the intended use of the composition. For example, if the composition is intended for human consumption, a food grade of purity may be appropriate. For medical use, a medical grade or medical device grade of purity should be used.

Preferably the enzyme is an oxidoreductase enzyme. Examples of oxidoreductase enzymes that can convert a substrate to release hydrogen peroxide include glucose oxidase, hexose oxidase, cholesterol oxidase, galactose oxidase, pyranose oxidase, choline oxidase, pyruvate oxidase, glycollate oxidase, and amioacid oxidase. The corresponding substrates for these oxidoreductase enzymes are D-glucose, hexose, cholesterol, D-galactose, pyranose, choline, pyruvate, glycollate and aminoacid, respectively.

A mixture of one or more oxidoreductase enzymes and one or more substrates for the oxidoreductase enzymes may be present in a composition of the invention.

According to a preferred embodiment of the invention, the oxidoreductase enzyme is glucose oxidase and the substrate is D-glucose.

The substance may be any substance that includes a substrate for the enzyme. Preferably the substance lacks catalase activity. Preferably the substance is an unrefined substance. The term "unrefined" is used herein to refer to substances that have not been processed into a pure form. Unrefined substances include substances that may have been concentrated, for example by drying or boiling.

Preferably the substance includes one or more substrates from a natural source (termed herein a "natural substance"). Examples of natural substances include substances from a plant source, including from sap, roots, nectar, flowers, seeds, fruit, leaves, or shoots. More preferably the substance is an unrefined natural substance.

Preferably the substance comprises one or more of the following substrates: D-glucose, hexose, cholesterol, D-galactose, pyranose, choline, pyruvate, glycollate or aminoacid.

Preferably the substance is a sugar substance. The term "sugar substance" is used herein to mean any substance that includes one or more sugars. The term "sugar" is used herein to refer to a carbohydrate with the general formula $C_m(H_2O)_n$. Preferred sugars include monosaccharides, such as D-glucose, hexose, or D-galactose. Preferably the sugar substance includes one or more sugars from a natural source (termed herein a "natural sugar substance"). More preferably the natural sugar substance is an unrefined natural sugar substance. The unrefined natural sugar substance may be (or be derived from) a natural sugar product. In a preferred embodiment, the unrefined natural sugar product is a honey. In some preferred embodiments, the honey is a honey that has been treated to remove or inactivate catalase activity. Alternatively, the unrefined natural sugar substance may be a processed natural sugar, such as a syrup or an inverted syrup.

As discussed above, the substance itself may preferably lack an enzyme activity that is able to convert the substrate to release hydrogen peroxide (referred to as "substrate conversion activity"). Absence of substrate conversion activity from the substance has the advantage that there is then no variability in the amount of this activity between similar substances from different sources, or from different harvests from the same source. This further reduces the variability in antimicrobial activity that can be generated from such substances. Substrate conversion activity is then provided only by the enzyme that is contacted with the substance, and so the amount of substrate conversion activity present in the composition can be controlled.

Substrate conversion activity may be removed during processing or extraction of the substance, or inactivated before use of the substance in a composition of the invention. Substrate conversion activity may be inactivated by heat inactivation, for example by pasteurisation. A suitable temperature for heat inactivation of substrate conversion activity is at least 80° C., preferably for at least two minutes. An advantage of heat inactivation is that both catalase activity and substrate conversion activity can be inactivated in a single heat inactivation step.

A storage-stable composition of the invention may include an antimicrobial agent. For example, hydrogen peroxide may be present if the storage-stable composition is formed by contacting the enzyme with the substance in aqueous solution under conditions for conversion of the substrate by the enzyme, and then drying the composition to reduce its water content to a level where there is insufficient free water to allow the enzyme to convert the substrate. Preferably, however, the storage-stable antimicrobial composition does not include any detectable hydrogen peroxide. Such composition may be formed, for example, by contacting the enzyme with the substrate in the absence of sufficient free water to allow the enzyme to convert the substrate. Examples of other antimicrobial agents that may be present in a storage-stable composition of the invention include: an antibiotic, an antiviral agent, or an anti-fungal agent.

It is particularly preferred that a composition of the invention is a food standard composition. Such compositions may be used for human consumption. In other particulrly preferred embodiments, the composition is medical grade or medical device grade composition. Alternatively, a composition of the invention may be of animal food standard for animal consumption.

It is particularly preferred that each component of the composition is a natural substance (i.e. each component is derived from a natural source). Compositions of the invention which contain only natural ingredients provide an attractive alternative to drug-based antimicrobial formulations.

Preferably the substance is a honey. The honey may preferably be a medical grade or medical device grade honey. In some embodiments, it is preferred that the honey is a honey that has been treated to remove or inactivate catalase activity originally present in the honey. According to a preferred embodiment of the invention, the substance is a pasteurised honey, and the enzyme is a glucose oxidase. According to preferred embodiments, the substance is a medical grade or medical device grade honey, and the enzyme is a medical grade or medical device grade enzyme, preferably glucose oxidase.

Honey is a natural product made by honey bees using nectar from flowers. It is a saturated or super-saturated solution of sugars. Honey is defined in the Codex Alimentarius international food standard as "the natural sweet substance produced by honey bees from the nectar of plants or from secretions of living parts of plants or excretions of plant sucking insects on the living parts of plants, which the bees collect, transform by combining with specific substances of their own, deposit, dehydrate, store and leave in the honey comb to ripen and mature" (Revised Codex Standard for Honey, 2001).

Nectar typically includes approximately 14% simple sugars (w/w), 1% phenol compounds, and 85% water. The phenol compounds give the honey its taste, aroma and colour. In the warm conditions of the hive, typically 36° C., the nectar would very quickly ferment. To prevent this, the nectar is mixed with secretions, containing enzymes, from the salivary and hypopharyngeal glands of foraging bees. In the hive the nectar is passed from bee to bee and more secretions are added before it is stored in the cells of the hive. The amount of enzymes present varies with the age, diet and physiological stage of the bees (when a bee is a forager its glands produce more digestive enzymes), strength of the colony, temperature of the hive, and the nectar flow and its sugar content.

The enzymes added to nectar by bees include diastase, which catalyses the conversion of starch to dextrin and sugar, Invertase, which catalyses the conversion of sucrose to fructose and glucose, and glucose oxidase, which catalyses the conversion of glucose to hydrogen peroxide and gluconic acid. Low doses of hydrogen peroxide prevent the growth of yeasts that would quickly ferment the nectar. As the bees progressively dry the nectar to form honey, the gluconic acid makes the honey acidic (between pH 3.5 and 4.5). Water is effectively trapped to the sugar molecules in the honey and is not available for further chemical reactions. The amount of 'free' water in honey is measured as the water activity ($a_w$). The range of $a_w$ found in honey has been reported to be 0.47-0.70, with mean values of 0.562 and 0.589 (RCIEGG, M; BLANC, B, 1981, The water activity of honey and related sugar solutions. Lebensmittel-Wissenschaft and Technologie 14:1-6). The $a_w$ of ripened honey is too low to support the growth of any species, with no fermentation occurring if the water content is below 17.1% (Molan, P. C. (1992). The antibacterial activity of honey: 1. The nature of the antibacterial activity. Bee World, 73(1), 5-28). The acidity of the honey and the lack of free water prevent the further risk of fermentation, and stop the glucose oxidase working. Honey also contains variable amounts of catalase originating from the nectar.

A typical chemical composition of blossom honey is:

TABLE 1

| | Blossom honey | |
|---|---|---|
| Component | Average (% w/w) | Min-Max (% w/w) |
| Water content | 17.2 | 15-20 |
| Fructose | 38.2 | 30-45 |
| Glucose | 31.3 | 24-40 |
| Sucrose | 0.7 | 0.1-4.8 |
| Other disaccharides | 5 | |
| Total sugars | 79.7 | |
| Minerals | 0.2 | 0.1-0.5 |
| Amino acids, Proteins | 0.3 | 0.2-0.8 |
| Acids | 0.5 | 0.2-0.8 |
| pH | 3.9 | 3.5-4.5 |

In addition, trace amounts of pollen are present, which can be used to identify the botanical origin of the honey, as well as the enzymes invertase, diastase, catalase, and glucose oxidase. There is also phytochemical component. This varies but is typically up to ~1%, depending on the source of the honey.

Once diluted, the glucose oxidase present in natural honey is able to convert glucose substrate in the diluted honey to release hydrogen peroxide. However, the variability in the content of honey (particularly in the content of glucose oxidase activity, glucose, and catalase activity) means that honeys from different sources, or different harvests of honey from the same source, can be very variable in their antimicrobial effectiveness.

According to an embodiment of the invention, the honey may be pasteurised. Pasteurisation of honey inactivates the catalase and glucose oxidase activity present in the honey. Optionally, the pasteurised honey may be filtered to remove any particles (such as wax particles and bee wings) that may be in the honey post harvest. To form a storage-stable composition of the invention, a glucose oxidase is contacted with the pasteurised honey once it has cooled to a temperature (suitably 35-40° C.) that will not inactivate the added glucose oxidase and at which the honey remains sufficiently liquid to facilitate mixing with glucose oxidase.

Honey can be pasteurised at a temperature that is sufficient for the heat inactivation of catalase activity. A suitable minimum temperature is from 60° C. to 80° C. This temperature should be maintained preferably for at least two minutes.

The control of the heat process may be important, since a bi-product of heating honey is the formation of HMF (HydroxyMethylFurfuraldehyde) which is used as an indicator of heat and storage changes in honey. HMF is formed by the breakdown of fructose in the presence of acid. Heat increases the speed of this reaction. The increase in speed is exponential with increasing heat. For every degree that the honey is raised above 40° C., close to the normal hive ambient temperature, HMF increases rapidly. HMF is not a harmful product. Jams, Molasses, Golden Syrup etc. can have levels of HMF 10 to 100 times that of honey. However HMF levels are used as an indication of degradation of honey and under the Codex Alimentarius Standard 40 mg/l is the maximum permissible level in the EU for table honey.

To prevent the build up of HMF it is preferred that the honey is raised rapidly to temperature levels to inactivate the catalase and then the honey is brought quickly down in temperature to a maximum of between 40 and 45° C. using a heat exchange mechanism.

No water is added during the process of this preferred embodiment, and so the resulting composition does not include sufficient free water to allow the glucose oxidase to convert the glucose present to release hydrogen peroxide. The storage-stable composition comprises: pasteurised honey, and added glucose oxidase. There is no detectable hydrogen peroxide present. The composition can be stored at ambient temperature for at least several days.

In other embodiments of the invention, the honey may be unpasteurised.

According to some preferred embodiments, the honey (pasteurised or unpasteurised) is a creamed honey. Creamed honey is a honey that has been processed to control crystallization. Creamed honey contains a large number of small crystals, which prevent the formation of larger crystals that can occur in unprocessed honey. A method for producing creamed honey was described in U.S. Pat. No. 1,987,893. In this process, raw honey is first pasteurised, then previously processed creamed honey is added to the pasteurized honey to produce a mixture of 10% creamed honey and 90% pasteurised honey. The mixture is then allowed to rest at a controlled temperature of 14° C. This method produces a batch of creamed honey in about one week. A seed batch can be made by allowing normal honey to crystallize and crushing the crystals to the desired size. Large scale producers have modified this process by using paddles to stir the honey mixture while holding the mixture at 14° C. In alternative creaming methods, the pasteurisation step may be omitted, with the honey instead being slowly warmed to 37° C.

The glucose oxidase is preferably a purified natural glucose oxidase preparation which is of food standard for human consumption, or of medical grade or medical device grade for medical applications. The activity of the glucose oxidase may be selected depending on the desired rate of production of hydrogen peroxide following dilution of the storage-stable composition. Several glucose oxidase preparations are commercially available (glucose oxidase is identified by the reference CAS:9001-37-0). Common microbial sources for glucose oxidase from non genetically modified organisms include selected strains of *Aspergillus niger, Penicillium amagasakiense, Penicillium variabile, Penicillium notatum*. Medical device grade glucose oxidase, from GMO *Aspergillus niger*, is available from Biozyme UK, activity 240 iu/mg. Food standard glucose oxidase, from *Aspergillus niger*, is available from BIO-CAT INC, activity 15,000 Units/g. Non-Genetically Modified glucose oxidase is available from BIO-CAT INC, activity 12,000/g. Glucose oxidase (GO3B2), from *Apsergillus niger*, is available from BBI Enzymes Limited, activity 360 Units/mg. Contaminants: alpha amylase no greater than 0.05%, Saccharase no greater than 0.05%, maltase no greater than 0.05% and GO/Cat no less than 2000.

The enzyme activity (for example, the glucose oxidase activity) may range, for example, from 1-400 IU/mg, or 1-300 IU/mg, for example 250-280 IU/mg. The amount of enzyme used is likely to depend on several factors, including the desired use of the composition, the amount of any catalase activity present in the substance, the amount of substrate present in the substance, the desired level of hydrogen peroxide release, and the desired length of time for hydrogen peroxide release. A suitable amount of enzyme can readily be determined by a person of ordinary skill in the art, if necessary using a well diffusion assay as described in Example 2 below to determine the extent of hydrogen peroxide release for different amounts of enzyme. Suitable amounts of enzyme (such as glucose oxidase) may be from 0.0001% to 0.5% w/w of the composition. The amount of enzyme used may be selected so as to produce a composition for generating antimicrobial activity that is equivalent to a selected phenol standard (for example a 10%, 20%, or 30% phenol standard).

Compositions of the invention, particularly compositions of the invention in which the substance is honey (for example, unpasteurised honey), and the enzyme is glucose oxidase that is able to convert D-glucose in the honey to release hydrogen peroxide, may comprise at least 1 unit, and preferably up to 1500 units, of glucose oxidase per gram of the composition. The glucose oxidase is additional (i.e. added as a result of human intervention) to any glucose oxidase activity that may naturally be present in the substance.

A "unit" is defined herein as the amount of enzyme causing the oxidation of 1 micromole of glucose per minute at 25 degrees centigrade at pH 7.0.

The Applicant has found that the antimicrobial potency of compositions of the invention may be increased simply by increasing the amount of glucose oxidase activity present in the composition.

In some embodiments of the invention, a composition of the invention comprises more than 15 units, for example at least 30 units, at least 50 units, or at least 100 units, and suitably less than 685 units, for example 100-500 units, of glucose oxidase per gram of the composition. Such compositions have been found to have superior antimicrobial properties than compositions with up to 15 units of glucose oxidase per gram of the composition. In particular, such compositions have increased potency against a wide range of microorganisms, including MSSA, MRSA, Group A and B *Streptococci, Enterococcus, E.coli, E.coli* ESBL, *Serr.liquefaciens* Amp C, *Kleb.pneumoniae, Pseud.aeruginosa*, and *Candida albicans*.

In other embodiments of the invention, a composition of the invention comprises at least 500 units, for example 500-1000 units, or 685-1000 units, of glucose oxidase per gram of the composition. Such compositions have been found to have even more superior antimicrobial properties. In particular such compositions have further increased potency against a wide range of microorganisms, including MSSA, MRSA, *E.coli* ESBL, and *Staphylococcus aureus*.

The pasteurisation process inactivates any enzyme activity present in the honey, and so there is no variability in catalase and substrate conversion activity between pasteurised honeys from different sources, or between different harvests of honey from the same source. The amount of substrate conversion activity can be controlled by addition of a purified glucose oxidase preparation with a defined amount and activity of the enzyme. Thus, the inherent variability in antimicrobial properties between different types and harvests of honey is considerably reduced, and the antimicrobial properties of honeys with low antimicrobial potency are improved.

According to further preferred embodiments of the invention, the substance may be an inverted substance, preferably an inverted syrup, such as inverted maple syrup. The term "inverted" is used herein to mean that sucrose originally present in a substance has been converted to glucose and fructose, for example by the activity of an invertase or sucrase enzyme. Such inverted substances may then be used in compositions of the invention with the enzyme glucose oxidase.

Maple syrup is made from the sap of sugar maple or black maple trees. In cold climate areas, these trees store starch in their stems and roots before the winter, which when converted to sugar, rises in the sap in the spring. Maple trees can be tapped and the exuded sap collected and concentrated to form maple syrup. Maple syrup typically comprises approximately 66% sucrose, 33% water, and 1% glucose and fructose. Because of the low amount of glucose present, maple syrup does not have potent antimicrobial generating properties when combined with glucose oxidase. However, if the sucrose is first converted to glucose and fructose, for example by treatment with an invertase or a sucrase, the resulting inverted syrup includes a much higher level of substrate for glucose oxidase.

According to the invention there is further provided an antimicrobial composition, or a composition for generating antimicrobial activity, which comprises a substance that lacks catalase activity, and an enzyme that is able to convert a substrate in the substance to release hydrogen peroxide.

There is also provided according to the invention a method for producing an antimicrobial composition, or a composition for generating antimicrobial activity, which comprises: contacting an enzyme that is able to convert a substrate to release hydrogen peroxide with a substance that lacks catalase activity and that includes a substrate for the enzyme.

There is further provided according to the invention an antimicrobial composition, or a composition for generating antimicrobial activity, which comprises: a substance; and a purified enzyme that is able to convert a substrate in the substance to release hydrogen peroxide.

There is also provided according to the invention a method for producing an antimicrobial composition, or a composition for generating antimicrobial activity, which comprises: contacting a purified enzyme that is able to convert a substrate to release hydrogen peroxide with a substance that includes a substrate for the enzyme.

A composition, or an antimicrobial composition, of the invention may further comprise hydrogen peroxide. There is further provided according to the invention an antimicrobial solution which comprises a composition, or an antimicrobial composition, of the invention.

Compositions and solutions of the invention can be used to treat any microbial infection that can be treated by hydrogen peroxide. Examples include infection caused by gram positive bacteria, gram negative bacteria, acid-fast bacteria, viruses, yeasts, parasitic or pathogenic micro-organisms or fungi. In particular, infections caused by the following micro-organisms may be treated: *Escherichia coli, Staphylococcus aureus, Pseudomonas aeruginosa, Candida albicans, Propionibacterium acnes, Staphylococcus aureus, Staphylococcus epidermidis, Staphylococcus saprophytics*, Beta haemolytic *Streptococci* Group A or B, *Campylobacter coli, Campylobacter jejuni*, Methicillin Resistant *Staphylococcus Aureus* (MRSA), Methicillin Sensitive *Staphylococcus Aureus* (MSSA), *Botrytis cinerea, Mycobacterium tuberculosis, Cryptosporidium, Plasmodium*, and *Toxoplasma*.

According to the invention there is also provided use of a composition or solution of the invention to prevent or inhibit microbial growth.

There is also provided according to the invention a composition or solution of the invention for use as a medicament. There is further provided according to the invention a composition or solution of the invention for the prevention, treatment, or amelioration of a microbial infection. The invention also provides use of a composition or solution of the invention in the manufacture of a medicament for the prevention, treatment, or amelioration of a microbial infection.

There is further provided according to the invention a method of preventing, treating, or ameliorating a microbial infection, which comprises administering a composition or solution of the invention to a subject in need of such prevention, treatment or amelioration. The subject may be a human or animal subject. Compositions of the invention may be topically administered.

The Applicant has found that compositions of the invention, in particular compositions of the invention in which the unrefined natural substance is a honey, have remarkable wound healing properties. In particular, chronic wounds that have persisted for one month to over a year have visibly begun to heal within a few days of treatment with a composition of the invention.

In particular, it is believed that the wound healing activity of such compositions is due to the sustained, low level release of hydrogen peroxide that is provided when compositions of the invention are diluted, for example by wound exudate. This results in the delivery of oxygen to the wound site.

Oxygen has a variety of important roles in support of wound healing. The complex wound healing process demands large amounts of energy. If a wound becomes infected, then there is an even bigger energy demand, which in turn means that there is an even greater demand for oxygen. Oxygen is involved in many of the mechanisms of the natural healing process. It has a key role in metabolic support, matrix repair, antisepsis/infection control and signalling and control of cell responses. Wounds which receive adequate oxygen generally heal at an increased rate compared to those which don't have an adequate oxygenation. Ischemia/hypoxia can directly inhibit wound healing processes such as angiogenesis, collagen synthesis and epithelialisation, and also impedes the ability of leukocytes to kill bacteria. As bacteria multiply, more leukocytes are recruited to the wound site, further increasing oxygen consumption.

For a wound to heal, it must have sufficient energy and nutrients to drive the healing process. Oxygen is essential in these metabolic processes. Tissue regeneration and healing involves formation of granulation tissue, epithelialisation, contraction, and re-modelling. The healing process requires the proliferation of cells of various types, as matrix is built-up, new blood vessels are formed and epithelium is replaced. Such cellular activity depends on oxygen availability to allow unhindered respiration. The biosynthetic pathways needed to build all the biopolymers (e.g. proteoglycans, structural proteins) are dependent on oxygen to satisfy the underlying energy requirements. Various enzymes are required, including the matrix metallo-proteinases, and these, too, are costly in terms of energy, and hence oxygen, requirements.

Collagen synthesis is a fundamental part of these processes. The deposition of collagen is crucial for rebuilding of connective tissue and as part of the process of angiogenesis. Oxygen is a co-factor required in the hydroxylation of proline and lysine during the formation of pro-collagen. Mature collagen synthesis requires prolyl-hydroxylase and lysyl-hydroxylase enzymes, both of which are dependent on oxygen for their function.

Neovascularization/angiogenesis is essential for complete healing. This must be triggered by an appropriate signal. In high oxygen environments, macrophage leukocytes can trigger this signal, leading to an orchestrated, complex series of events involving tissue degradation followed by collagen formation and organisation, endothelial cell migration/colonisation and vessel formation.

When a wound is created the body's natural defences are activated. Neutrophils gather at the wound site shortly after trauma and release bactericidal reactive oxygen species (ROS) and hydrogen peroxide ($H_2O_2$) to kill bacteria and prevent infection. Macrophages arrive at the wound in response to environmental stimuli, phagocytose foreign particles, and release vascular endothelial growth factor (VEGF), an angiogenic factor crucial for wound healing. Oxygen has a key role in these events. One of the main microbial killing mechanisms of macrophages and neutrophil leukocytes is the "respiratory burst"—a natural activity by which these cells kill microbes. Individuals with defects in their respiratory burst process fall victim to bacterial infections. Leukocytes need oxygen to deliver the respiratory burst effect, and enhanced oxygen levels can boost its potency. These leukocytes also have other bacterial killing mechanisms, triggered when they swallow-up the microbes (phagocytosis). This is an oxygen-dependent process, as it involves substantial energy expenditure, so it does not work well in an oxygen-deprived environment. It works best in an oxygen-enriched situation. Oxygen is also lethal to anaerobic bacteria and is important in the effective functioning of some antibiotics.

Molecular oxygen is an important cell signal interacting with growth factors and other signals (for example, redox signals) to regulate signal transduction pathways. The molecular signal released by macrophages to trigger angiogenesis is "Vascular Endothelial Growth Factor" (VEGF). High oxygen levels can cause macrophage leukocytes to release VEGF. The genes for a number of other important factors and enzymes are induced by high oxygen levels.

The production of nitric oxide (NO) is also recognised as a pivotal signalling and control event in wound healing. NO is made by the enzyme nitric oxide synthase (NOS), and in the early stages of wound healing the inducible form of the enzyme (iNOS) is up-regulated. However, it can only function if arginine and oxygen are in plentiful supply, to enable production of NO at the appropriate rate.

Oxygen also has a direct role in signalling (stimulating) the process of epithelialisation, a key later-stage healing event in which new epithelial cells proliferate, organise themselves and differentiate into structured epithelium.

Thus, the sustained supply of oxygen to the wound site by compositions of the invention is believed to be particularly important in promoting wound healing.

It is believed that the wound healing activity of preferred compositions of the invention is also contributed to by a number of activities of the compositions in addition to their hydrogen-peroxide releasing activity. In particular, preferred compositions are believed to have ability to debride and deodorise a wound, to have anti-inflammatory properties, to be able to stimulate tissue growth, and to manage pain and minimise scarring.

Malodour is a common feature of chronic wounds and is attributed to the presence of anaerobic bacterial species that produce malodorous compounds from decomposed serum and tissue proteins. In addition to the antimicrobial action, compositions of the invention that include glucose (preferably 24-40% by weight) allow bacteria to metabolise this in preference to amino acids, resulting in the production of a non-odorous metabolite, lactic acid.

Compositions of the invention with a high osmolarity (suitably having an $a_w$ in the range similar to honey, i.e. 0.47-0.7) are believed to facilitate the debridement of wounds by the autolytic action of tissue proteases. Compositions of the invention create a moist wound environment by drawing out lymph fluid from the wound tissues through their strong osmotic action. This provides a constant supply of proteases at the interface of the wound bed and the overlying necrotic tissue. This action also washes the surface of the wound bed from beneath. The activation of proteases by hydrogen peroxide released by compositions of the invention in contact with water may also assist. The debriding action may also contribute to the lowering of a wound's bacterial load by removal of dead tissue. Dead tissue is well known to provide an excellent medium for bacterial growth and increase the risk of infections if left in the wound.

The body's inflammatory response marks the beginning of the healing process, but a prolonged reaction can inhibit healing, causing further damage to the tissues and making it harder to manage the wound. A prolonged inflammatory response is often associated with high levels of exudate. Suppressing inflammation, as well as reducing pain for the patient, reduces the opening of blood vessels, thus lessening oedema and exudate. It is thought that the ability of compositions of the invention to clear infection and debride wounds contributes to the anti-inflammatory action. Compositions of the invention that include antioxidants (preferably one or more antioxidants present in honey) may also reduce excessive inflammation by mopping up free radicals.

Prolonged inflammation causes fibrosis that manifests as hypertrophic scarring in wounds. Preferred compositions of the invention may reduce scarring by reducing inflammation, promoting angiogenesis and stimulating the formation of granulation tissue. Preferred compositions of the invention may also stimulate the growth of epithelium.

Compositions of the invention are also believed to have immunostimulatory effects mediated by interleukin-1 (IL-1). Compositions of the invention are believed to promote the release of IL-1 from skin cells. IL-1 is a cytokine which is also secreted by macrophages, monocytes and dendritic cells. It is an important part of the inflammatory response of the body against infection. It increases the expression of adhesion factors on endothelial cells to enable transmigration of leukocytes to sites of infection. It also acts on the thermoregulation centre of the brain leading to an increased body temperature. It is referred to as an endogenous pyrogen. The increased body temperature helps the body's immune system to fight infection. This is the initial phase of an inflammatory immune response which augments the antimicrobial activity of the system. The inflammatory response plays a central role in wound healing through its defence against possible infection and by participating in cell and tissue repair and re-growth. The antimicrobial effect of compositions of the invention is believed to be aided and complemented by the immunostimulatory effect which aids the re-growth and repair of damaged tissues and/or cells.

Compositions of the invention, particularly honey-based compositions, provide a moist healing environment for wound tissue with no risk of maceration of the surrounding skin, and prevent adherence of dressings to the wound bed so that there is no pain and no tissue damage when dressings are changed. Such compositions also stimulate healthy cell development and accelerate granulation and epithelialisation processes in the wound. The compositions also have an occlusive action to protect the wound and damaged tissues. It is also believed that honey-based compositions cause a significant decrease in wound pH which favours the healing process.

According to a preferred aspect of the invention, a composition of the invention may be used in a method of wound care, including the treatment of a wound, or the treatment or management of wound sepsis.

The wound may be an acute wound, chronic wound, surgical wound (for example, a Caesarean wound), chronic burn, or an acute burn. A composition of the invention may be used in the prophylactic prevention of wound sepsis. If a storage-stable composition of the invention is used, it will be appreciated that this may be diluted by liquid present at the wound site, which thereby leads to the release of hydrogen peroxide by the diluted composition.

A wound occurs when the integrity of any tissue is compromised (e.g. skin breaks, muscle tears, burns, or bone fractures). A wound may be caused by an act (a trauma) or surgical procedure, by an infectious disease, or by an underlying condition.

Acute wounds include surgical incisions and traumatic injuries such as lacerations, abrasions, avulsions, penetrations or bites, and burn injuries. Acute wounds normally proceed through an orderly and timely reparative process that results in sustained restoration of anatomic and functional integrity.

A chronic wound is a wound that has been in existence for more than three weeks or that has failed to proceed through an orderly and timely process to product anatomic and functional integrity or to proceed through the repair process without establishing a sustained and functional result (Lazarus et al, Arch Dermatol. 1994;130(4):489-493).

Chronic wounds can be classified into four categories: venous ulcers, arterial ulcers, diabetic ulcers, and pressure ulcers. A small number of wounds that do not fall into these categories may be due to causes such as radiation poisoning or ischemia.

Venous ulcers, which usually occur in the legs, account for about 70% to 90% of chronic wounds and mostly affect the elderly. They are thought to be due to venous hypertension caused by improper function of valves that exist in the veins to prevent blood from flowing backward. Ischemia results from the dysfunction and, combined with reperfusion injury, causes the tissue damage that leads to the wounds. In venous disease, ulcers are usually located in the gaiter area between the ankle and the calf, often on the medial aspect of the leg.

Arterial leg ulcers occur as a result of reduced arterial blood flow and subsequent tissue perfusion. Atherosclerosis or peripheral vascular disease is the most common cause of arterial leg ulceration. A reduction in blood supply, if left untreated, can cause death of tissue in the area being fed by the affected artery. Ulcer development is often rapid with deep destruction of tissue. Arterial leg ulcers can occur anywhere on the lower leg and are often deeper and rounded, with clearly defined borders.

Diabetic ulcers: diabetes causes immune compromise and damage to small blood vessels, preventing adequate oxygenation of tissue, which can cause chronic wounds. Diabetes causes neuropathy, which inhibits nociception and the perception of pain. Thus, patients may not initially notice small wounds to legs and feet, and may therefore fail to prevent infection or repeated injury. Pressure also plays a role in the formation of diabetic ulcers. Diabetics have a 15% higher risk for amputation than the general population due to chronic ulcers.

Pressure ulcers usually occur in people with conditions such as paralysis that inhibit movement of body parts that are commonly subjected to pressure such as the heels, shoulder blades, and sacrum. Pressure ulcers are caused by ischemia that occurs when pressure on the tissue is greater than the pressure in capillaries, and thus restricts blood flow into the area. Muscle tissue, which needs more oxygen and nutrients than skin does, shows the worst effects from prolonged pressure. As in other chronic ulcers, reperfusion injury damages tissue.

When treating ulcers it is desirable to: create a barrier to protect the wound while it is healing; provide a moist wound environment; deslough the wound; reduce bacterial load; and ideally promote healing with immunomodulation and improved nutrition. No conventional wound treatment product is able to achieve all of these effects. Some conventional treatments have some of these effects, but are quite toxic, and so are not ideal treatments. However, compositions of the invention, in particular compositions of the invention in which the substance is a honey, have all of these properties. In addition, the antimicrobial potency of compositions of the invention can be controlled to be far more potent than other honey-based wound care products, and the compositions are effective against a range of pathogens involved in chronic wounds, including antibiotic resistant organisms, such as MRSA.

Compositions of the invention are particularly advantageous in the early treatment of wounds, especially in patients, such as diabetic patients, where the wounds are likely to get worse. Early treatment with compositions of the invention prevents the complications that arise in chronic wounds, keeps the patients active, and avoids the expense of dealing with complications.

Compositions of the invention have also been found to be effective at reducing or preventing infection of surgical wounds. Infection of surgical wounds is a problem, particularly in Caesarean sections which have quite a high infection rate of around 10%. Compositions of the invention are simple to apply post surgery. For example, a composition of the invention may be applied to a dressing, and then contacted with the wound, and held in place with a secondary dressing. Example 40 below demonstrates that a single application of a composition of the invention to a Caesarean wound post surgery reduced the rate of surgical site infection by 60% compared to historical data.

Peripherally inserted central catheters (PICC lines) are used to administer chemotherapy treatment and/or other medicines. A PICC line is a long, thin, flexible tube which is inserted into one of the large veins of the arm near the bend of the elbow. It is then threaded into the vein until the tip sits in a large vein just above the heart. It is, however, possible for an infection to develop inside the line or in the area where it goes into the vein. If an infection develops, patients are typically given antibiotics. If these don't clear the infection, or if the infection is serious, the line may be removed. To reduce the chances of an infection developing, a dressing containing an antimicrobial agent such as chlorhexidine or silver may be applied to the line entry site.

Compositions of the invention have been found to be effective at preventing and clearing colonisation of PICC lines by topical application of a composition of the invention to the line entry site (see Example 39 below).

Compositions of the invention can be easily applied without any specialist training or complex equipment. The compositions are highly suitable for use in the third world, where patients often have increased susceptibility to infection, and the materials and instruments used in surgery and wound care are often more infected than in developed countries.

Compositions of the invention are non toxic, and do not have any of the problems associated with silver-containing dressings, PVP-I, or chlorhexidine.

Compositions of the invention may also be used to treat donor or recipient graft sites.

According to the invention there is provided a method of treating a wound, which comprises administering a composition of the invention to the wound.

There is also provided according to the invention a composition of the invention for treatment of a wound.

There is further provided according to the invention use of a composition of the invention in the manufacture of a medicament for treatment of a wound.

There is also provided according to the invention a method of treating inflammation, which comprises administering a composition of the invention to a site of inflammation.

There is also provided according to the invention a composition of the invention for treatment of inflammation.

There is further provided according to the invention use of a composition of the invention in the manufacture of a medicament for treatment of inflammation.

There is also provided according to the invention a method of stimulating tissue growth, which comprises administering a composition of the invention to a site in need of such stimulation.

There is also provided according to the invention a composition of the invention for stimulating tissue growth.

There is further provided according to the invention use of a composition of the invention in the manufacture of a medicament for stimulating tissue growth.

There is also provided according to the invention a method of debriding a wound, which comprises administering a composition of the invention to a wound in need of debridement.

There is also provided according to the invention a composition of the invention for debriding a wound.

There is further provided according to the invention use of a composition of the invention in the manufacture of a medicament for debriding a wound.

There is also provided according to the invention a method of deodorising a wound, which comprises administering a composition of the invention to a wound in need of deodorising.

There is also provided according to the invention a composition of the invention for deodorising a wound.

There is further provided according to the invention use of a composition of the invention in the manufacture of a medicament for deodorising a wound.

For wound healing applications, compositions of the invention may be administered at an appropriate frequency determined by the healthcare provider. Suitably compositions of the invention may be administered at least every several days, for example every week, but preferably every day or every other day.

The amount of a composition of the invention administered will depend on many factors, such as the strength of the antimicrobial properties of the composition, and other wound healing properties of the composition, on the size of the wound, and on the age and condition of the subject to be treated. However, for many applications it is expected that administration of 2-100 g, or 5-100 g of a composition of the invention will be suitable, preferably 10-50 g.

According to preferred embodiments of the invention, a composition of the invention is sterile. Sterile compositions are preferably used for medical applications such as wound healing.

Compositions of the invention may be sterilised by any suitable means. The Applicant has found that compositions of the invention retain glucose oxidase activity (and, therefore, the ability to release hydrogen peroxide on dilution) following sterilisation by exposure to gamma irradiation.

Thus, according to the invention there is provided a composition of the invention that has been sterilised by exposure to gamma irradiation.

There is also provided according to the invention a method of sterilising a composition of the invention, which comprises exposing the composition to gamma irradiation.

A suitable level of gamma irradiation is 10-70 kGy, preferably 25-70 kGy, more preferably 35-70 kGy.

Since ozone has not been authorised by the US FDA for sterilisation of honey-based products for use in wound healing, compositions of the invention preferably have not been sterilized by ozonation, and do not include ozone, or any components that have been subjected to sterilisation by ozonation. In particular, compositions of the invention should not comprise ozonized honey or ozonated oil.

Preferred compositions of the invention for medical use are sterile, single use compositions.

Sterilised compositions of the invention that are stored away from exposure to light are expected to retain stability for at least six months. For example, such compositions may be packaged in high-density polyethylene/low-density polyethylene (HDPE/LDPE) tubes or in polyester-aluminium-polyethylene (PET/Al/PE) sachets.

A composition of the invention is preferably a medical grade or medical device grade composition. Preferably the unrefined natural substance is a honey, suitably a medical grade or medical device grade honey.

Preferably a composition of the invention comprises a creamed honey, more preferably a creamed unpasteurised honey. Such compositions can readily be administered topically because the presence or number of large crystals has been minimised by the creaming process.

For compositions of the invention that comprise honey, it will be appreciated that there may be no need to use pasteurised honey in the composition if the composition is sterilised. It may instead be preferable to use unpasteurised honey (preferably creamed honey) or other unrefined natural substance. In particularly preferred embodiments, compositions of the invention comprise unpasteurised honey, and added purified glucose oxidase.

Thus, according to the invention there is provided a storage-stable composition for generating antimicrobial activity, which comprises unpasteurized honey, and added purified glucose oxidase that, in the presence of sufficient free water, is able to convert D-glucose in the honey to release hydrogen peroxide, wherein the composition does not include sufficient free water to allow the glucose oxidase to convert the D-glucose.

According to the invention there is also provided a method for producing a storage-stable composition for generating antimicrobial activity, which comprises: contacting unpasteurized honey with purified glucose oxidase that, in the presence of sufficient free water, is able to convert D-glucose in the honey to release hydrogen peroxide, wherein the composition does not include sufficient free water to allow the glucose oxidase to convert the D-glucose.

Such compositions preferably comprise at least 1 unit, and preferably up to 1500 units, of glucose oxidase per gram of the composition. Suitably such compositions comprise more than 15 units of glucose oxidase per gram of the composition, for example at least 100 units, and preferably 100-500 units, of glucose oxidase per gram of the composition, or at least 500 units, and preferably 500-1000 units, of glucose oxidase per gram of the composition.

The honey of such compositions may comprise a creamed unpasteurized honey.

Also according to the invention, there is provided a pharmaceutical composition comprising a composition of the invention together with a pharmaceutically acceptable carrier, excipient, or diluent.

According to certain preferred aspects of the invention, there is provided a dressing comprising a composition of the invention. Suitable dressings include gauzes, bandages, tissues, films, gels, foams, hydrocolloids, alginates, hydrogels, or polysaccharide pastes, granules or beads. A composition of the invention may be present together with a wound-dressing matrix, such as a collagen or collagen-glycosaminoglycan matrix.

A composition of the invention may be in the form of a solid or semi-solid preparation. Examples of solid or semi-solid preparations include capsules, pellets, gel caps, powders, hydrogels, pills, pillules, or globules. Alternatively, a composition of the invention may be in the form of a liquid preparation. Examples of liquid preparations include a syrup, paste, spray, drop, ointment, cream, lotion, oil, liniment, or gels. A typical gel includes an alcoholic gel such as an isopropanol, ethanol, or propanol gel, or a hydrogel.

A composition of the invention may be in a form suitable for administration to a human or animal subject. Suitable forms include forms adapted for topical or oral administration. Forms suitable for topical administration include a topical ointment, cream, lotion, oil, liniment, liquid, gel, or a dissolvable strip. Forms suitable for oral administration include a capsule, pellet, gel cap, pill, pillule, globule, lozenge, dental floss, toothpaste, mouthwash, dissolvable film strips. If a storage-stable composition of the invention is used, this may be diluted by liquid present at the site of administration (for example, by saliva for oral administration, or by exudate from a wound), leading to release of hydrogen peroxide at the administration site.

A composition of the invention may be present with at least one suitable antimicrobial or immunostimulatory component, excipient or adjuvant, or any other suitable component where it is desired to provide ability to generate antimicrobial activity. For example, a composition of the invention may be present with an antiseptic, a cough medicine, a nappy care formulation, a moisturiser, an itch relief formulation, a cleanser, a scrub, a wash, a barrier formulation, an exfoliating formulation. Preferably, however, compositions of the invention do not include any antibiotic.

A composition of the invention may be in a form suitable for controlled or sustained-release delivery. For example, an oral administration form may have an enteric coating to provide for controlled or sustained-release delivery.

According to another aspect of the invention, a composition of the invention may be in a form for use as a cosmetic composition. A composition of the invention may be present with at least one suitable cosmetic excipient or adjuvant. Cosmetic applications cover many different personal care applications, including the treatment of hair conditions, such as dandruff, or the treatment of body odour.

A composition of the invention may be provided in the form of a prophylactic hand barrier solution or hand sanitizer solution. Such a hand barrier solution may be provided in the form of a cream, lotion, or hydrogel, and is used as a hand wash type product with advantageous properties for the prophylactic prevention of microbial infection.

Advantageously, a composition of the invention may be used in the treatment or prevention of MRSA or other antibiotic resistant micro-organisms and bacteria. The invention overcomes the problem of emerging antibiotic resistant strains of micro-organisms in a non-toxic manner. For this application, a composition of the invention may be administered topically, for example as a topical ointment, cream, lotion, oil, liniment, liquid and/or gel. A composition of the invention may be administered as part of a tissue or skin wipe.

The microbial infection may be an oral, eye, ear, skin, chest, or nail infection. The oral infection may be gum disease, oral ulceration and/or an oral hygiene disorder. The oral hygiene disorder may be halitosis and/or gingivitis. Alternatively, the oral infection may be a throat infection or a nasal infection, including nasal Staphylococci infections. An eye infection may include conjunctivitis. The skin infection may be a fungal skin infection. Fungal skin infections include athlete's foot and/or ringworm in humans. In veterinary medicine, fungal skin conditions include foot rot, ringworm and the control of zoonotic skin infections. The nail infection may be a fungal nail infection, such as onychomycosis.

A composition of the invention may be used for the treatment of a skin disorder, such as acne, eczema, or psoriasis. Acne and eczema may have a microbial infection component which can be treated by the composition, and secondary microbial infections of psoriatic lesions caused by scratching can be treated by a composition of the invention.

A composition of the invention may be used in veterinary medicine. Important veterinary applications include the treatment of microbial infections and the treatment or management of wound care, or burn treatment. Specific conditions include chronic skin infections in dogs (subcutaneous *Staphylococcus* infections), Otitis externa (ear infections), oral care in animals, *Campylobacter* infections in chickens, coliosis, enteric microbial infections in pigs, poultry and cattle, Cryptosporidium infections, clearance of zoonotic infections, wound dressing, e.g. horn removal, and abscess treatment. The present invention has particular advantages in veterinary usage, in that it allows the treatment of microbial infections without introducing antibiotics into the food chain.

A composition of the invention may be provided with any other composition or product for which it is desired to provide the ability to generate antimicrobial activity. The composition of the invention may be provided as a mixture with the other composition or product, or separately therefrom, for example packaged as a kit with the other composition or product. Where a composition of the invention is provided as a mixture with the other composition or product, it is preferred that this other composition or product does not include sufficient free water to allow the enzyme to convert the substrate of the composition of the invention.

A composition of the invention may be provided with instructions for use of the composition. For example, a composition of the invention may be packaged as a kit with the instructions.

According to the invention there is provided a kit for preventing, treating, or ameliorating a microbial infection, or for treating a wound, which comprises a composition or solution of the invention, and instructions for administering the composition or solution.

There is further provided according to the invention a method for preventing or inhibiting microbial growth, which comprises applying a composition or solution of the invention to a surface or region where it is desired to prevent or inhibit microbial growth.

Compositions or solutions of the invention may be particularly useful for preventing or inhibiting growth of a plant or insect pathogen. For example, compositions or solutions of the invention may be particularly suitable for prolonging the shelf-life of edible produce (such as a fruit or a vegetable), or other produce (such as high value plant material, including bulbs, especially lily bulbs, or flowers), by preventing or inhibiting microbial growth that would otherwise spoil the produce. Treatment of edible produce, or other produce, with a composition or solution of the invention, particularly where this contains only natural ingredients, may be preferred to use of a pesticide or pharmaceutical product.

According to a preferred embodiment, a composition or solution of the invention may be used to prevent or inhibit growth of *Erwinia*. *Erwinia* is a genus of Enterobacteriaceae which contains mostly plant pathogenic species. These species produce enzymes that hydrolyze pectin between plant cells, causing the cells to separate, a disease termed "plant rot". A well-known member of the genus is the species *E. amylovora*, which causes fireblight on apple, pear, and other Rosaceous crops. *Erwinia carotovora* (also known as *Pectobacterium carotovorum*) is another species, and has a wide host range, including carrot, potato, tomato, leafy greens, squash and other cucurbits, onion, green peppers. This species is able to cause disease in almost any plant tissue it invades. It is a common cause of decay in stored fruits and vegetables, and so is a very important pathogen. Decay caused by *E. carotovora* is often referred to as bacterial soft rot (BSR).

*Erwinia* infection is a particular problem for storage of potatoes. Significant losses can occur if *Erwinia* germinates, and causes black putrefaction of the centre of the potato. This problem is currently controlled with a pharmaceutical product. According to a preferred embodiment of the invention a composition or solution of the invention may be used to prevent or inhibit decay of potatoes caused by *Erwinia* infection. Use of compositions or solutions of the invention that contain only natural ingredients is particularly preferred.

According to a further aspect of the invention, a composition or solution of the invention may be used to prevent or inhibit growth of an insect pathogen, and in particular growth of *Nosema* in bees.

*Nosema* is the most widespread of adult honey bee diseases. It is caused by a unicellular microsporidian parasite which exists in two stages—a long-lived spore and a replicating vegetative stage. If an adult bee ingests spores they germinate into the vegetative stage which penetrates cells lining the bee's gut. There are two described species that infect honey bees, *Nosema apis* and *Nosema ceranae*. *Nosema apis* reduces the lifespan of infected bees. *Nosema ceranae* has crossed the species barrier from its Asiatic host, and has been found to be more virulent than *N. apis*. Infected foraging bees die away from the hive and this continuous loss of bees reduces food brought in to the hive until the colony collapses.

Treatment of Nosema with the antibiotic Fumidil B (prepared from *Aspergillus fumigatus*, the causative agent of Stone Brood) inhibits the reproduction of spores in the mid-gut, but does not kill the spores. This antibiotic is also very expensive, and must be applied in the off-season to minimise the risk that it will contaminate marketable honey and enter the human food chain.

We have found that compositions of the invention are able to kill the spores and the vegetative stage of *Nosema*. According to the invention there is provided a method for preventing or treating *Nosema* in bees, which comprises administering a composition or solution of the invention to bees. Preferably a storage-stable composition of the invention in the form of a powder is diluted with water and applied to a bee hive. A storage-stable composition of the invention in the form of a powder may be produced, for example, by dry pasteurisation of honey prior to contact with glucose oxidase in powder form.

Preferred embodiments of the invention are now described, by way of example only, with reference to the accompanying drawings in which.

Figure 36:
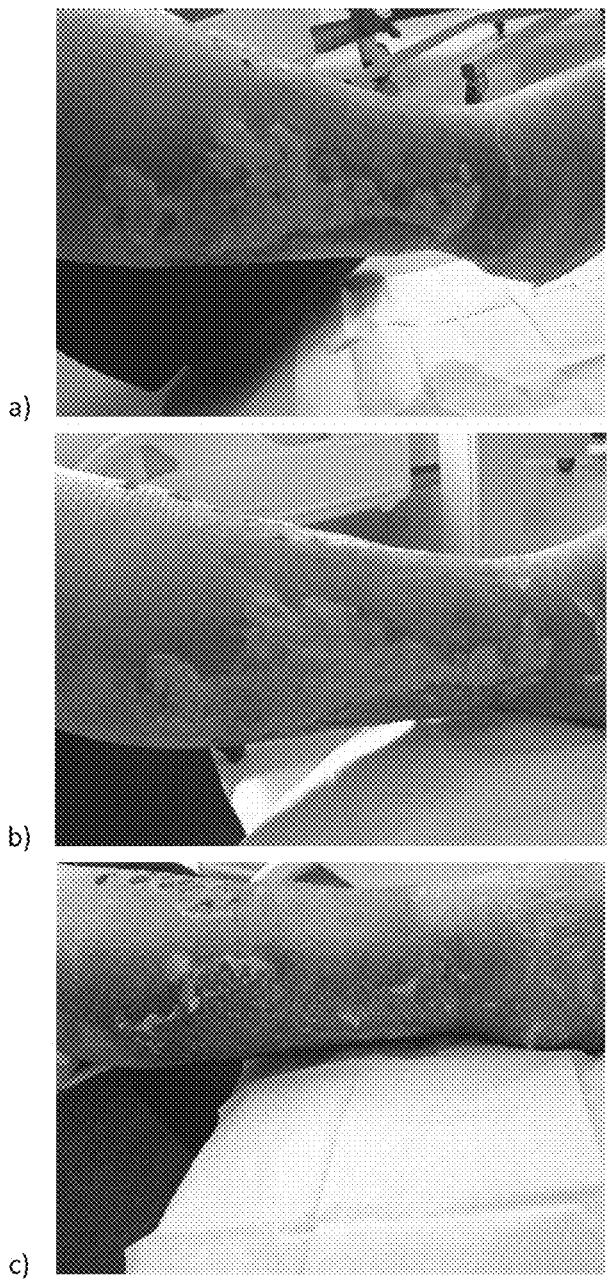
Figure 37:
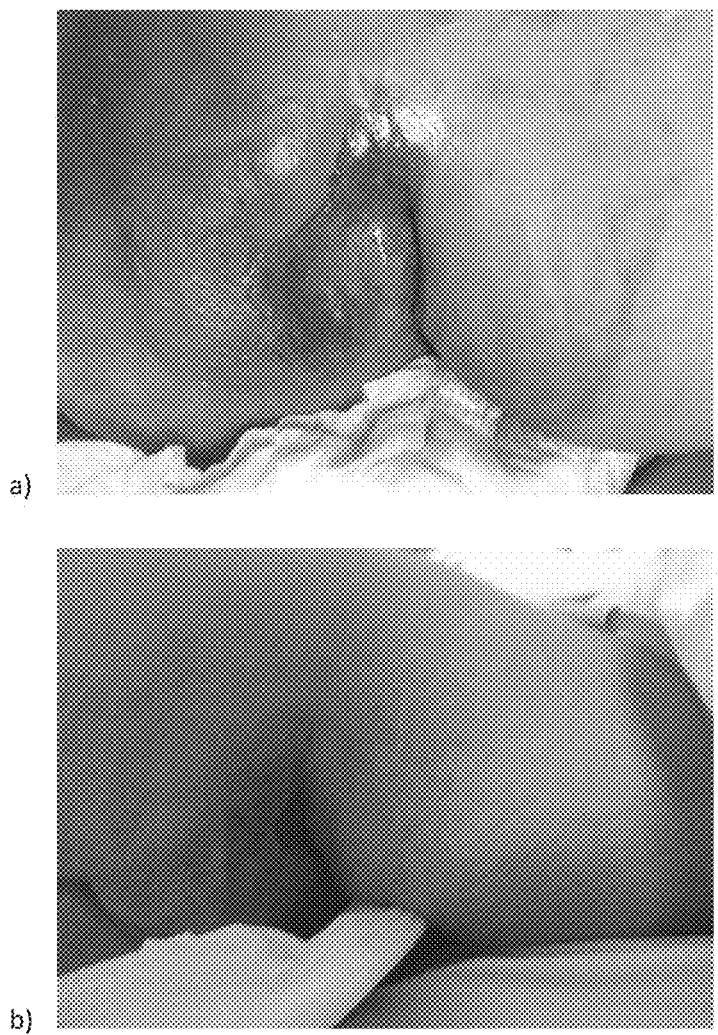
Figure 38:
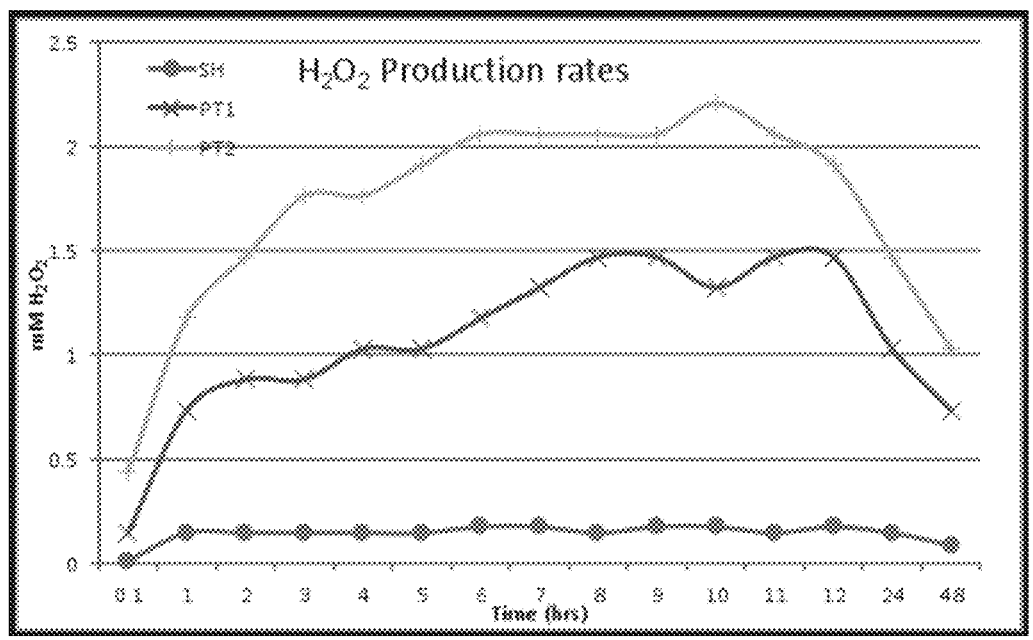
Figure 39:
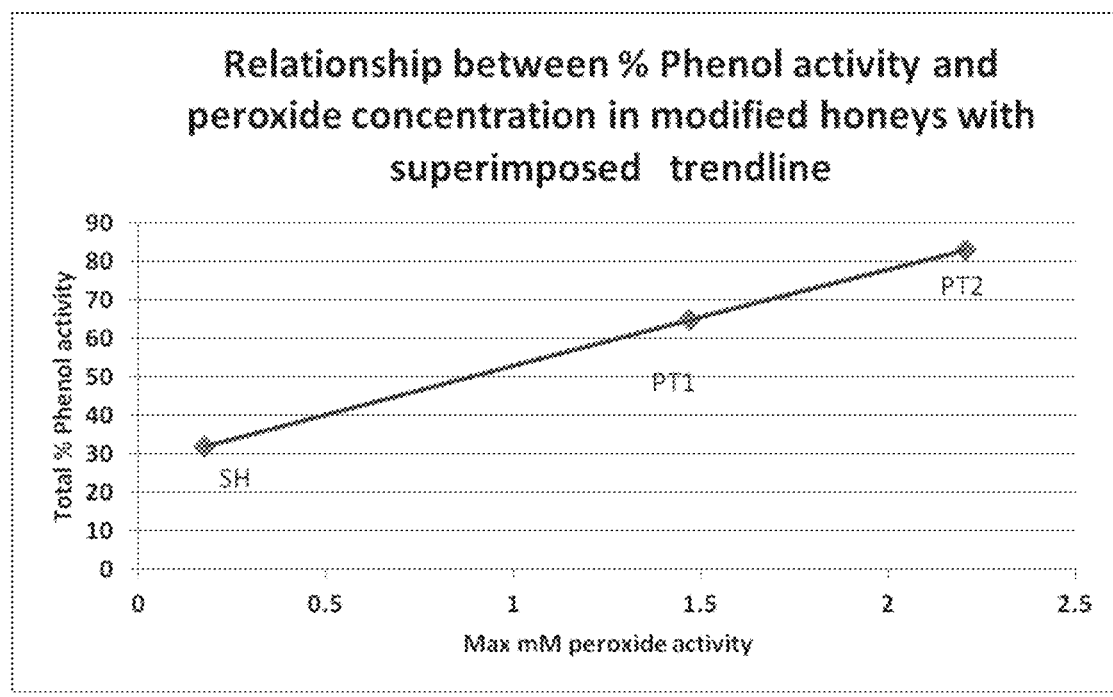

FIG. 36 shows photographs of the results of use of S1 Surgihoney to treat an infected leg ulcer, in which: (a) shows day 1 of treatment; (b) shows day 4 of treatment; and (c) shows day 7 of treatment;

FIG. 37 shows photographs of the results of use of S1 Surgihoney to treat a pressure sore, in which: (a) shows day 1 of treatment; and (b) shows day 30 of treatment;

FIG. 38 shows different hydrogen peroxide production rates for Surgihoney (SH) and two modified prototypes, PT1 and PT2; and FIG. 39 shows the relationship between phenol activity and maximum hydrogen peroxide activity in modified honeys, SH, PT1 and PT2.

EXAMPLE 1

This example describes a preferred process for production of a storage-stable composition of the invention, and dilution of the storage-stable composition to release hydrogen peroxide.

Process for Manufacture of "Activated" Honey

Honey is heated for 2 minutes to 80° C. using a heat exchanger (a lower temperature could be used if desired, suitably at least 60° C., provided this is sufficient to inactivate catalase). The purpose of this heating process is to pasteurise the honey, reduce its viscosity so that it can be filtered to remove any wax particles and bee wings that may be in the honey post harvest, and inactivate any catalase in the honey that would affect the efficient production of hydrogen peroxide.

The pasteurised honey is then filtered, and left to cool naturally to normal hive temperatures (35-40° C.). Glucose oxidase is then added at a low level (equivalent to the level found normally in honey) to replace the glucose oxidase naturally found in the honey but which has been inactivated by the pasteurisation process. The filtered pasteurised honey is fairly liquid at 35-40° C. so it can easily be mixed with the glucose oxidase. There is, however, no other reason why the mix could not be done at room temperature. The resultant "activated" honey is then stored at ambient temperature.

Apart from the replacement of the inactivated glucose oxidase there is no modification to the composition of the natural honey. There is no detectable hydrogen peroxide in the "activated" honey.

Dilution of "Activated" Honey

Following dilution of the "activated" honey, hydrogen peroxide is released after a lapse of time, as free water becomes available and the glucose oxidase starts to convert the glucose present in the honey. The hydrogen peroxide level is less than 2 mmol/litre but is released for an extended period.

EXAMPLE 2

This example describes the results of tests demonstrating the antimicrobial effect of activated Ulmo honey. The honey is described as "activated" if it contains added glucose oxidase.

Well Diffusion Assay

*Staphylococcus aureus* (NCIMB 9518) was grown on nutrient agar or in nutrient broth.

Antibiotic diffusion agar plates were inoculated with culture by swabbing overnight culture onto the surface of agar plates. Plates were allowed to stand at room temperature for 15 minutes. Wells 7 mm diameter were bored into the surface of the agar. Two hundred microlitres of sample (phenol standard, or honey) was placed into each well.

Plates were incubated for 16 hrs and zones of inhibition were measured using a dial calliper (+/−0.1mm). The diameter of zones, including the diameter of the well, were recorded.

Phenol standards were prepared by diluting phenol in purified water at the required concentration. For example, a 10% phenol standard was prepared by diluting 1 g of phenol in 9 g of purified water. The standards were stored at 30° C. and shaken before use.

Honey

Honey: Pasteurised Ulmo honey.

Non-activated honey (i.e. honey to which no glucose oxidase had been added) was used as a control.

Enzyme Preparation

Glucose oxidase: medical device grade material, non food grade, from GMO *Aspergillus niger*, supplied by Biozyme UK, activity 240 iu/mg. Initially 0.5% w/w enzyme was used, but this could be reduced to 0.005% w/w enzyme to achieve a 20% phenol standard equivalent.

Detection of Hydrogen Peroxide

Peroxide test from Merckoquant: Cat. No. 1.10011.0002 Measuring range/colour-scale graduation mg/l H2O2 0.5-2-5-10-25.

Procedure determination in aqueous solutions: dissolve honey in water 50/50 w/w. Immerse the reaction zone of the test strip in the measurement sample (15-30° C.) for 1 second. Allow excess liquid to run off via the long edge of the strip onto an absorbent paper towel and after 15 seconds (Cat. No. 110011) or after 5 seconds (Cat. No. 110081) determine with which colour field on the label the colour of the reaction zone coincides most exactly. Read off the corresponding result in mg/l $H_2O_2$ or, if necessary, estimate an intermediate value.

To determine that no endogenous hydrogen peroxide is available in the honey, dissolve in methanol 50/50 w/w. Determination in organic solvents (readily volatile ethers): Immerse the reaction zone of the test strip in the measurement sample (15-30° C.) for 1 second. After the solvent has evaporated (gently fan the strip back and forth for 3-30 seconds) immerse the reaction zone in distilled water for 1 second and allow excess liquid to run off via the long edge of the strip onto an absorbent paper towel or gently blow on the reaction zone four times, for 3-5 seconds each time. After 15 seconds (Cat. No. 110011) or after 5 seconds (Cat. No. 110081) determine with which colour field on the label the colour of the reaction zone coincides most exactly. Read off the corresponding result in mg/l $H_2O_2$ or, if necessary, estimate an intermediate value.

Results

Figure 1:
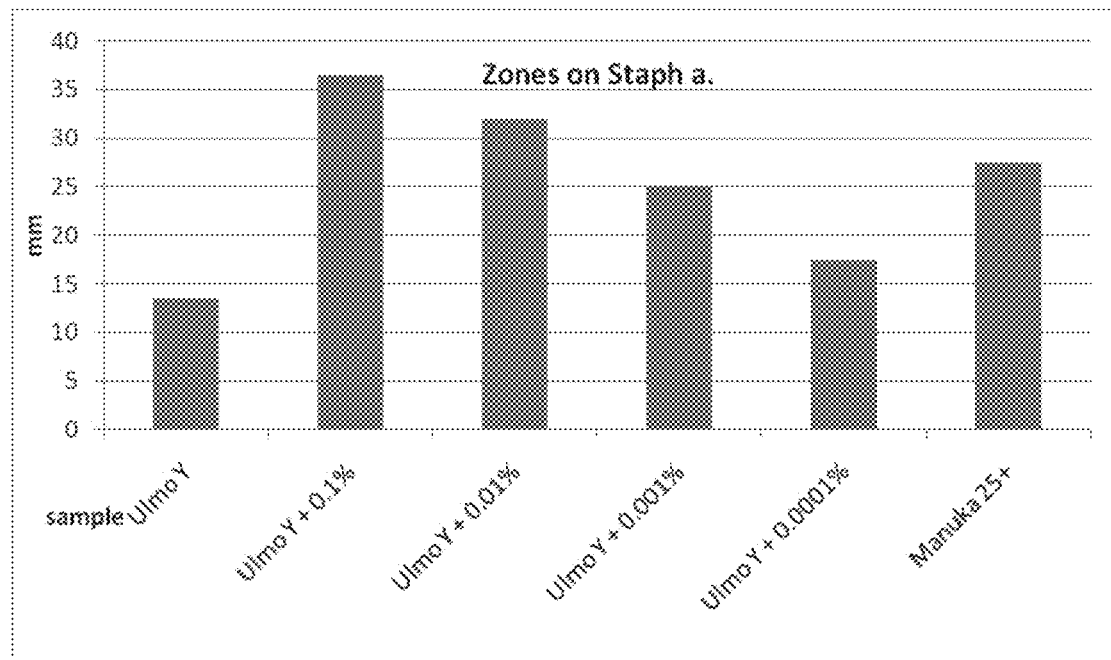
FIG. 1 shows the results from well diffusion assays for the antimicrobial effect of pasteurized Ulmo honey with different amounts of added glucose oxidase.
Figure 1:
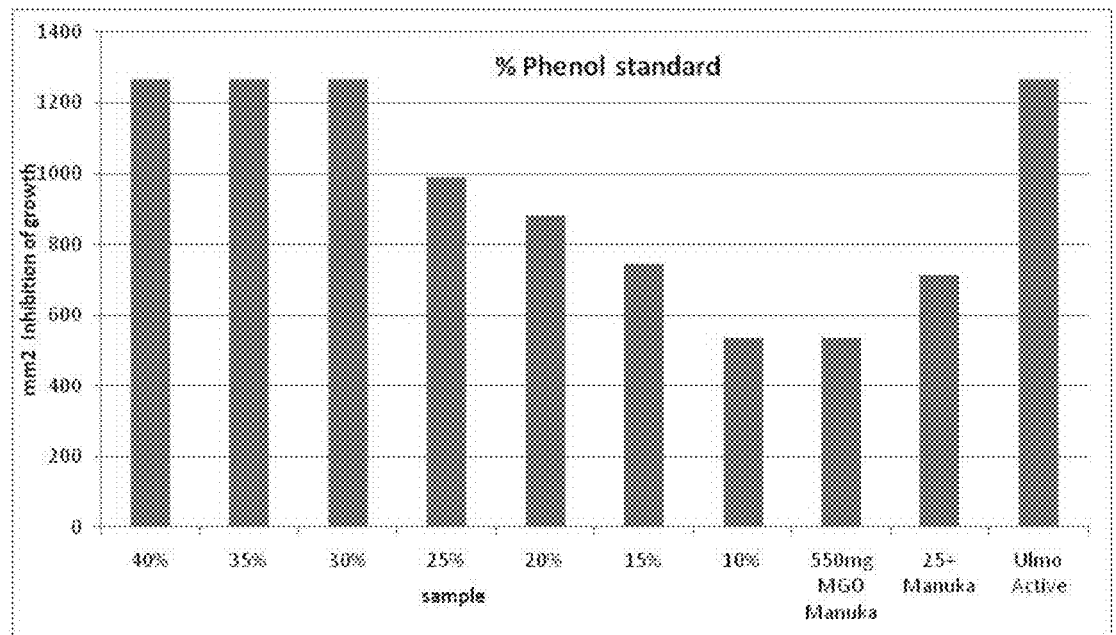

FIG. 1a shows the results from a well diffusion assay in which samples containing pasteurized Ulmo honey, pasteurized Ulmo honey to which different amounts of glucose oxidase enzyme preparation had been added (0.1%, 0.01%, 0.01%, 0.0015, or 0.0001% w/w), or Manuka UMF 25+ honey were added to the wells of an agar plate inoculated with *Staphylococcus aureus*. The results show the diameter of the zone of inhibition recorded for each sample.

The antimicrobial effect of activated honey containing at least 0.001% w/w glucose oxidase (240 iu/mg) on *Staphylococcus aureus* was equivalent to that of Manuka 25+ honey.

The effect of the activated honey is bactericidal.

FIG. 1b shows the results from a well diffusion assay in which a sample containing pasteurized Ulmo honey to which 0.5% w/w glucose oxidase enzyme preparation had been added was compared with samples of MGO Manuka honey, Manuka 25+ honey, and a range of different phenol standards (10%-40%). The results show the area of the zone of inhibition for each sample.

The results show that the effect of the activated Ulmo honey was equivalent to a 30% phenol standard, and was over twice as effective as MGO Manuka honey, and nearly twice as effective as Manuka UMF 25+ honey.

Figure 2:
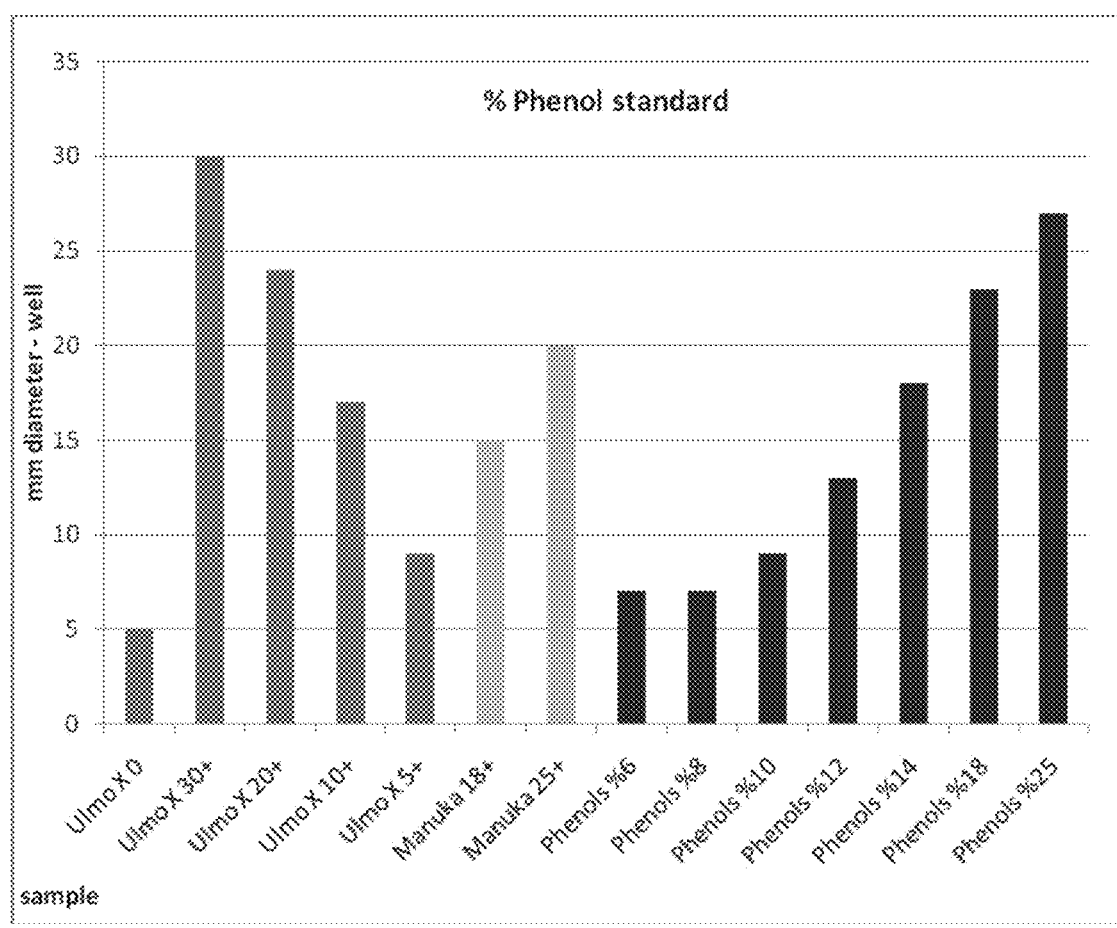
FIG. 2 shows the results from well diffusion assays for the antimicrobial effect of compositions of the invention with different amounts of enzyme in comparison with the effects of different phenol standards.

FIG. 2 demonstrates that the potency of the activated honey can be tailored to suit requirements by addition of a suitable amount of enzyme.

EXAMPLE 3

This example describes the results of tests demonstrating the antimicrobial effect of activated Tineo honey. The honey is described as "activated" if it contains added glucose oxidase.

Figure 3:
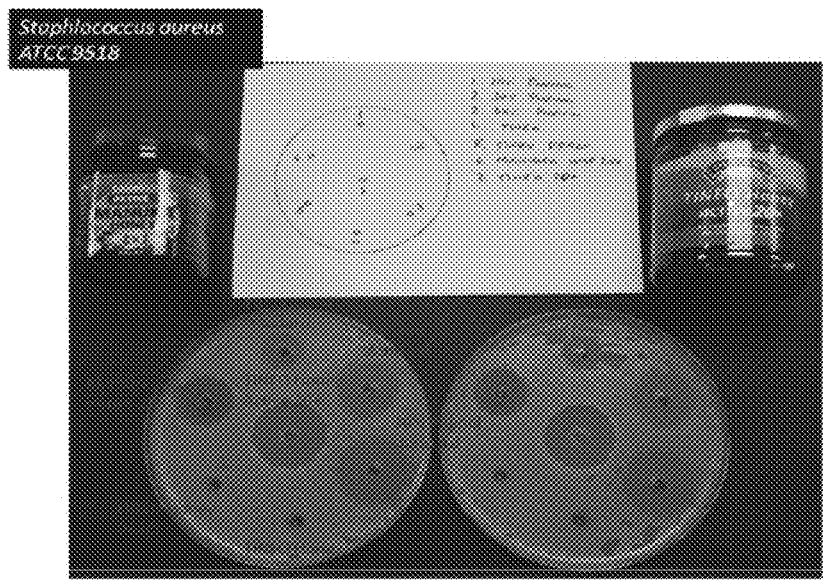
FIG. 3 shows photographs of the results from well diffusion assays for the antimicrobial effect of pasteurized Tineo honey with added glucose oxidase.
Figure 3:
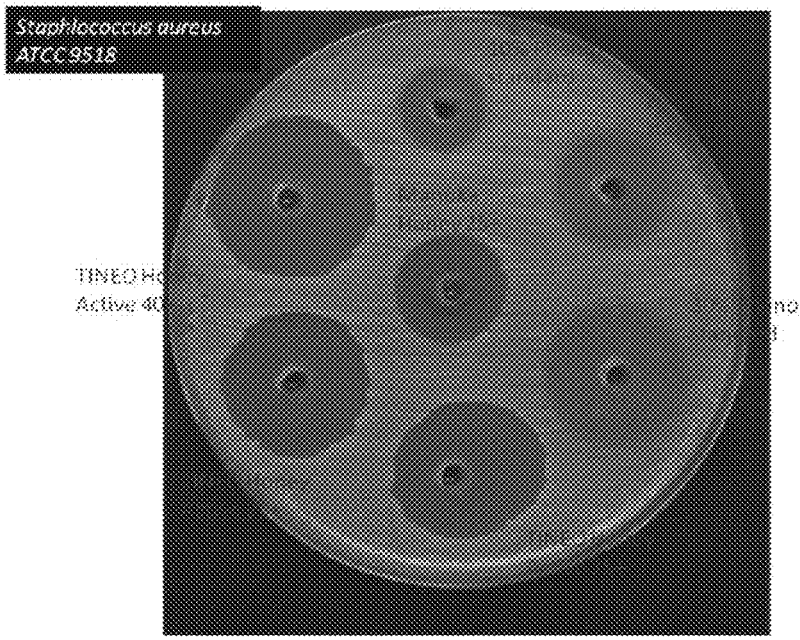
Figure 3:
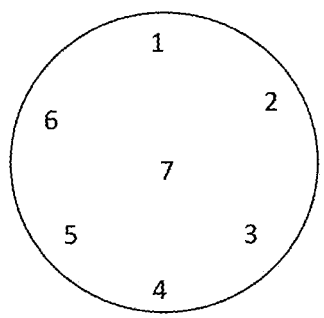

Well diffusion assays as described in Example 2 were carried out using samples of TINEO honey and different phenol standards. FIG. 3a is a photograph of duplicate agar plates showing zones of inhibition of *Staphylococcus aureus* caused by the different samples. The figure includes a representation showing the layout of the samples in the wells of the agar plate:
1. 10% Phenol Standard
2. 20% Phenol Standard
3. 30% Phenol Standard
4. TINEO Honey (pasteurized TINEO honey containing no added glucose oxidase)
5. TINEO Deact (pasteurized TINEO honey, with further heat deactivation)
6. Manuka UMF 25+
7. TINEO 20+ (pasteurized TINEO honey with added glucose oxidase, 0.005% Biozyme enzyme)

FIG. 3a shows that neither TINEO honey alone, nor TINEO deactivated honey caused inhibition of *Staphylococcus aureus* growth. The effect of TINEO honey with added glucose oxidase (TINEO 20+) was greater than the effect of Manuka UMF 25+, and equivalent to the 30% phenol standard.

FIG. 3b is a photograph of an agar plate showing zones of inhibition of *Staphylococcus aureus* caused by different samples, which were arranged as shown below:
1. 10% Phenol Standard
2. 20% Phenol Standard
3. 30% Phenol Standard
4. TINEO Honey Active 25+ (0.005% enzyme w/w)
5. TINEO Honey Active 25+ (0.005% enzyme w/w)
6. TINEO Honey Active 40+ (0.05% enzyme w/w)
7. Manuka Honey UMF 25+

FIG. 3b shows that the TINEO Honey Active 25+ and 40+ samples were more effective in inhibiting growth of *Staphylococcus aureus* than the Manuka Honey 25+ sample.

EXAMPLE 4

This example describes the results of tests demonstrating the antimicrobial effect of activated Ulmo and Tineo honey.

Figure 4:
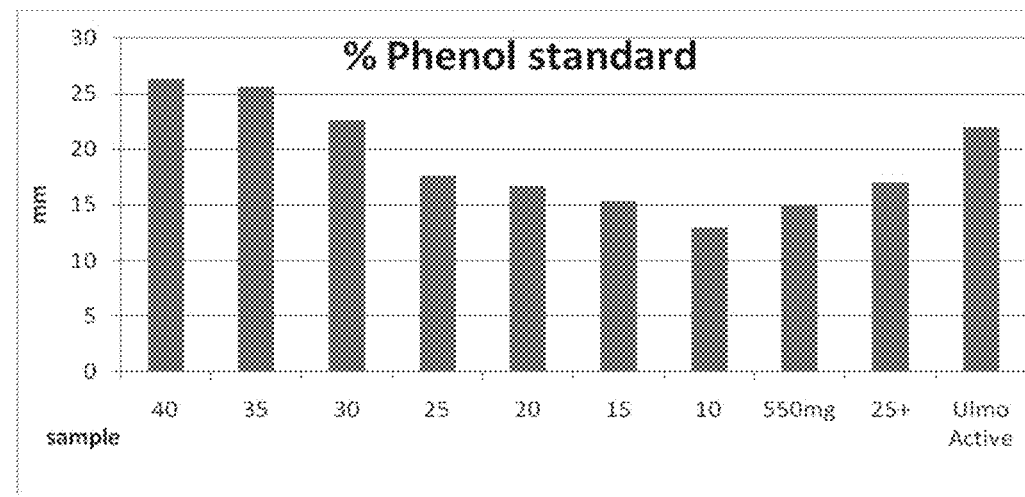
FIG. 4 shows the results from well diffusion assays for the antimicrobial effect of different compositions of the invention.
Figure 4:
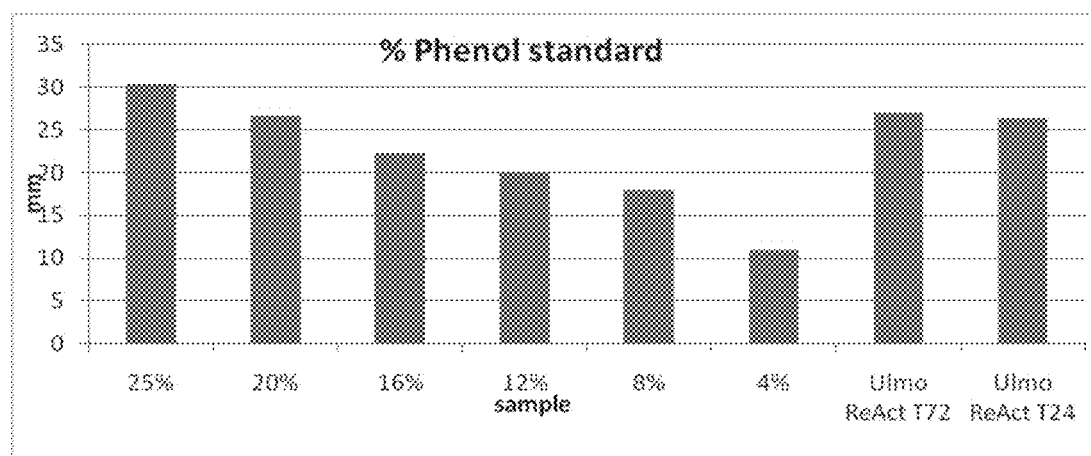
Figure 4:
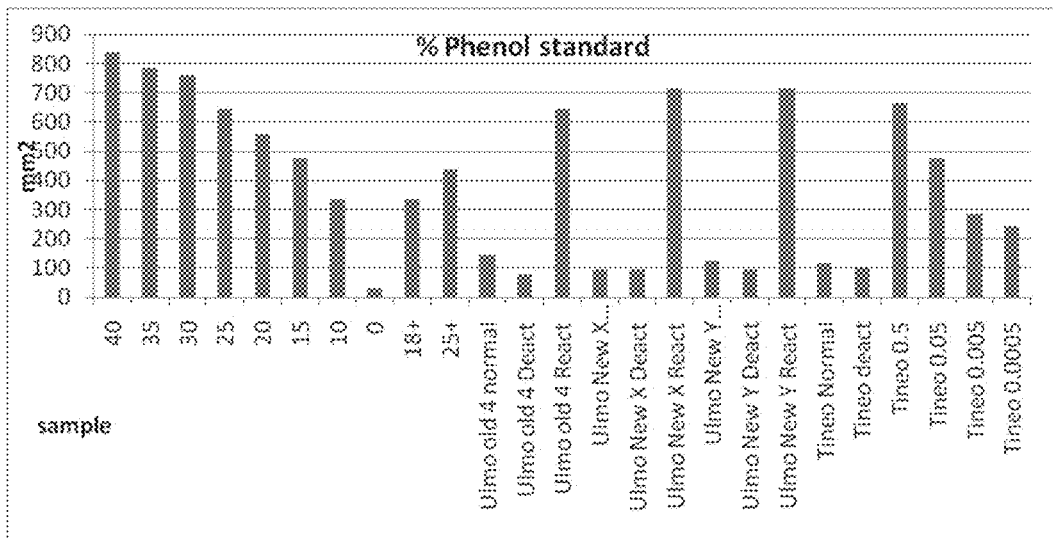

FIG. 4a shows the results of three repeats from a well diffusion assay, carried out as described in Example 2, measuring the zones of inhibition of growth of *Staphylococcus aureus* following 24hrs incubation. Samples of phenol in DI water at a range of concentrations from 40-10%, and samples of 2 types of Manuka (Manuka UMF 25+, Manuka 550MGO, and activated Ulmo honey with 0.01% w/w Biozyme glucose oxidase (as in Example 2).

FIG. 4b shows the results from a further well diffusion assay. Glucose oxidase (Biozyme preparation as described in Example 2) was added to pasteurized Ulmo honey (0.005% enzyme w/w), and stored at 40° C. for 24 or 72 hours. Samples from the stored activated honeys were then tested for activity against *Staphylococcus aureus* in a well diffusion assay, as described in Example 2, and compared with a range of phenol standards from 4-25%. FIG. 4b shows that the activated honey was stable when stored at 40° C. for 72 hours, and that the activated honey was equivalent to the 20% phenol standard in its effectiveness against *Staphylococcus aureus*.

FIG. 4c shows the results from a further well diffusion assay in which the activity of new and old batches (the old batch was received approximately four months before the new batch) of pasteurized Ulmo honey (Biozyme preparation as described in Example 2, 0.5% w/w), and Tineo honey with increasing amounts of added glucose oxidase (Biozyme preparation as described in Example 2, 0.0005-0.5% w/w) were compared with Manuka 18+ and 25+ UMF honey, and a range of phenol standards from 10-40%. In FIG. 4c, "normal" refers to pasteurized honey as received, "Deact" refers to pasteurized honey that has been further heat deactivated, and "React" refers to pasteurized honey that has been further heat deactivated, prior to addition of glucose oxidase. Thus, the Ulmo honey was tested without ("Ulmo old 4 normal", "Ulmo New X", and "Ulmo New Y") and with added glucose oxidase. FIG. 4c shows the area of the zones of inhibition of *Staphylococcus aureus*. It can be seen that the old batch of pasteurized Ulmo honey ("Ulmo old 4 React") retained equivalent activity to the new pasteurized batches ("Ulmo New X React" and "Ulmo New Y React"). All of these batches showed approximately two-fold higher activity than Manuka honey 18+, and higher activity than Manuka honey 25+. Adding increasing amounts of glucose oxidase to the pasteurized Tineo honey increased the activity of the honey.

In this test, 0.005% w/w enzyme was approximately equivalent to the 10% phenol standard, 0.05% w/w enzyme was approximately equivalent to the 15% phenol standard, and 0.5% w/w enzyme was approximately equivalent to the 25% phenol standard. The Manuka 18+ honey was equivalent to the 10% phenol standard, and the Manuka 25+ honey showed activity that was intermediate between the 10% and 15% phenol standard.

EXAMPLE 5

In this example, the effect of different glucose oxidase enzyme preparations was tested with pasteurized Tineo honey. The enzyme preparations used were the Biozyme preparation as described in Example 2, and a food grade, non-GMO source, glucose oxidase from ANHUI MINMETALS DEVELOPMENT I/E CO., LTD (referred to as the "Anhui" enzyme preparation below).

Figure 5:
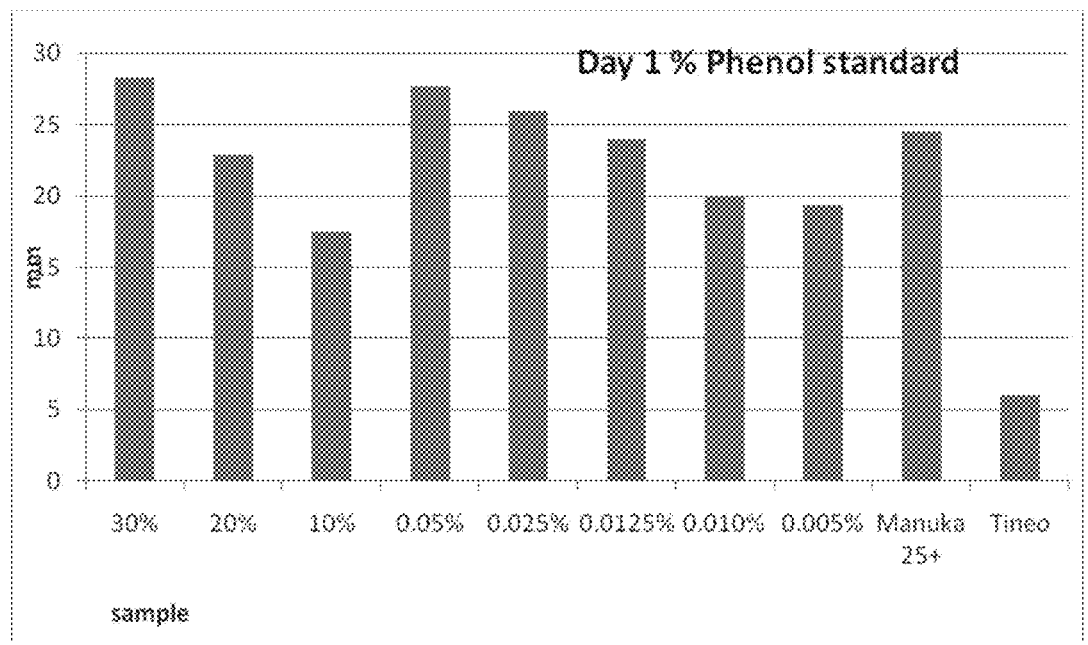
FIG. 5 shows the results from well diffusion assays for the antimicrobial effect of compositions of the invention that include different enzyme preparations.
Figure 5:
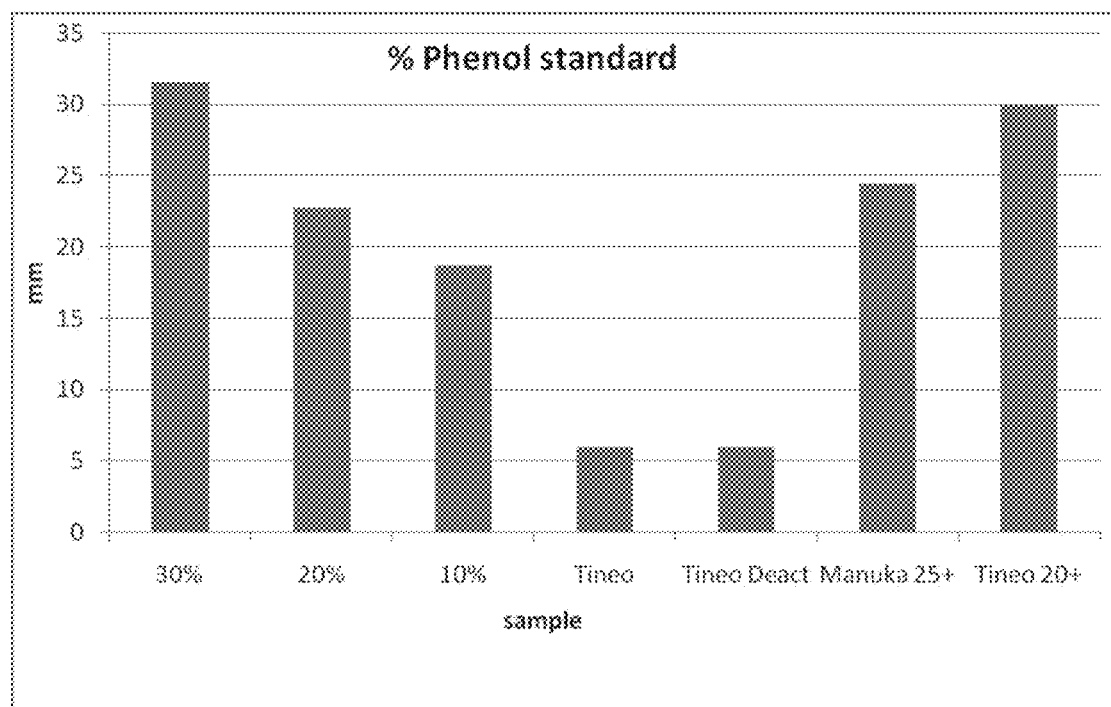

FIG. 5a shows the results from a well diffusion assay carried out as described in Example 2, in which samples of pasteurized Tineo honey containing either no enzyme, or 0.005-0.05% w/w Anhui enzyme were compared with different phenol standards (10%, 20%, 30%) and a sample of Manuka honey UMF 25+. The results show that increasing the amount of enzyme increases the effectiveness of the activated honey against *Staphylococcus aureus*. 0.0125% w/w enzyme was approximately equivalent to the 20% phenol standard and the Manuka honey sample, and 0.05% w/w enzyme was approximately equivalent to the 30% phenol standard.

FIG. 5b shows the results from a well diffusion assay carried out as described in Example 2, in which different amounts of the enzyme was added to samples of a commercial batch of pasteurized Tineo honey. The "Tineo" sample is the pasteurized honey with no added glucose oxidase. The "Tineo Deact" sample is the pasteurized honey which has been further heat treated, and contains no added glucose oxidase. The "Tineo 20+" sample contains 0.005% w/w of the Biozyme glucose oxidase. The results show that the Tineo sample has no activity against *Staphylococcus aureus*. The Tineo 20+sample was more effective against *Staphylococcus aureus* than the Manuka 25+, and was intermediate between the 20% and 30% phenol standards.

EXAMPLE 6

This example describes the results of tests of the stability of activated honeys stored for 60 or 90 days.

Glucose oxidase enzyme from Biozyme, as described in Example 2, was added to pasteurized Ulmo or Tineo honey at 0.005% w/w, and the resulting mixtures were stored at 37° C. for two months (Ulmo honey samples) or at room temperature for 90 days (Tineo honey samples). The amount of enzyme used corresponds to the amount that would be used for a commercial food product.

Figure 6:
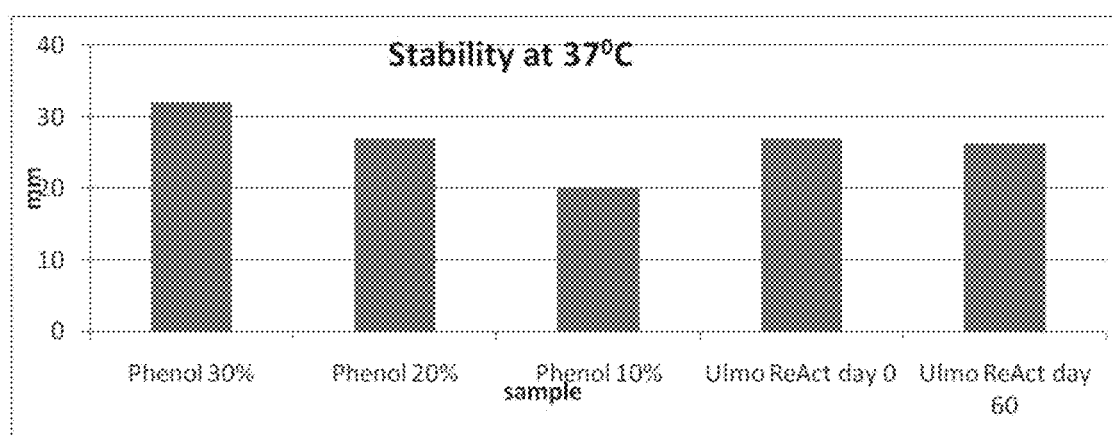
FIG. 6 shows the results from well diffusion assays for the antimicrobial effect of compositions of the invention after storage for 60 or 90 days.
Figure 6:
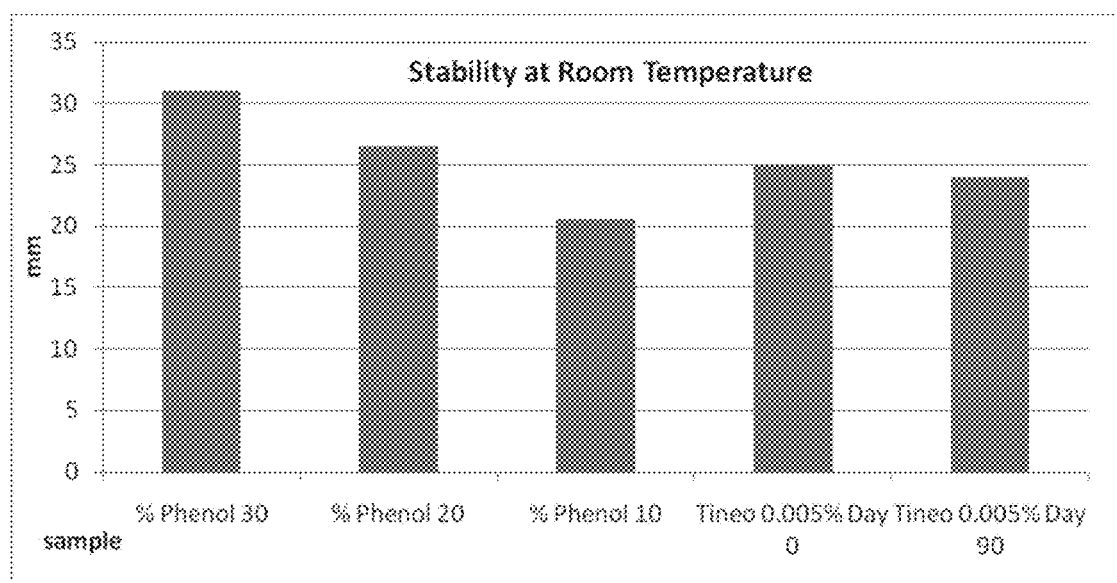

After storage, the samples were tested in a well diffusion assay against *Staphylococcus aureus* carried out as described in Example 2. The stored samples were compared with 10%, 20%, and 30% phenol standards. FIG. 6a shows the results for the Ulmo honey samples, and FIG. 6b shows the results for the Tineo honey samples. There was no apparent loss of activity for the storage period for either type of honey.

EXAMPLE 7

This example describes the results of tests of the antimicrobial activity of a powdered activated honey in which glucose oxidase enzyme in powder form is added to a powdered honey.

Figure 7:
FIG. 7 shows the results from well diffusion assays for the antimicrobial effect of powdered formulations of compositions of the invention.
Figure 7:
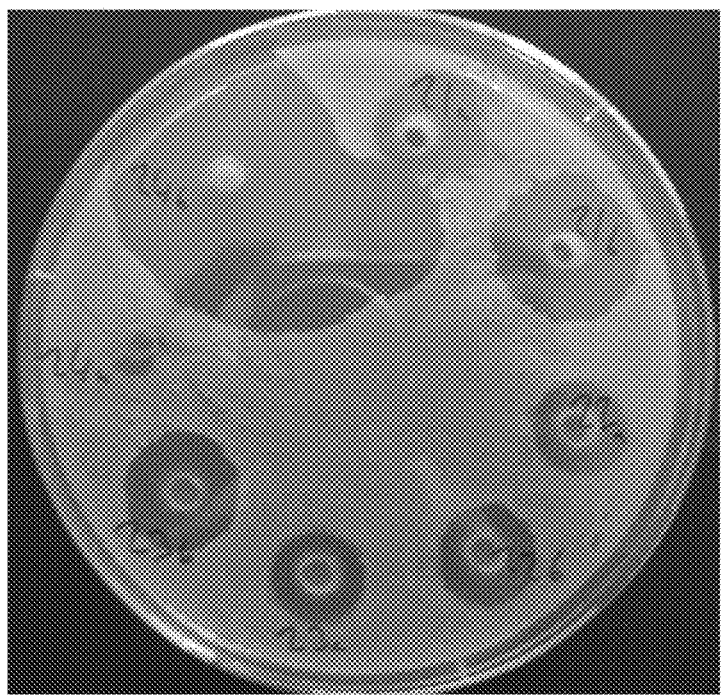

Powdered honey was obtained from Honi Bake from ADM Specialty Ingredients. 0.1% w/w Biozyme glucose oxidase (as described in Example 2) was added to the powdered honey. The antimicrobial activity of the mixture was tested in a well diffusion assay against *Staphylococcus aureus* as described in Example 2. The mixture was added to two different wells of the agar plate. A control was used with honey powder only. The results are shown in FIG. 7a. The control well showed no activity, but the activated honey showed clear zones of inhibition.

FIG. 7b shows the results of another well diffusion assay in which a different powdered honey was mixed with powdered enzyme from ANHUI MINMETALS DEVELOPMENT I/E CO., LTD (Example 5). Sample well 24a is the honey powder only, and sample well 24b is honey powder mixed with 1% w/w enzyme. Again, a clear zone of inhibition can be seen.

EXAMPLE 8

Figure 8:
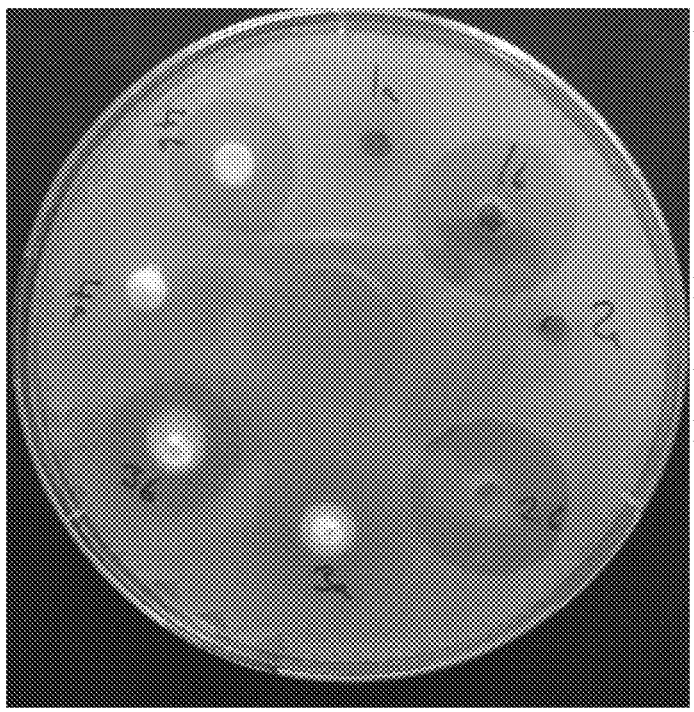
FIG. 8 shows the results from well diffusion assays for the antimicrobial effect of different products in the presence and absence of a composition of the invention.
Figure 8:
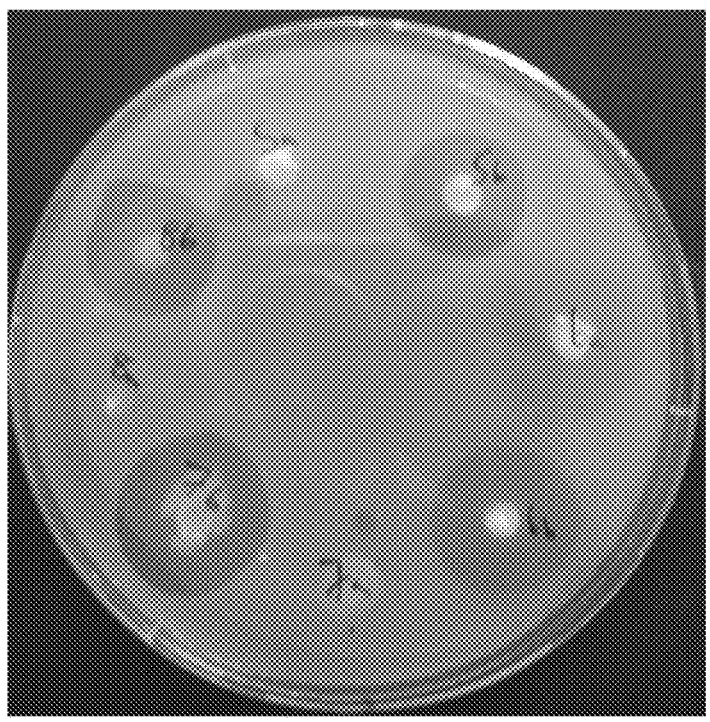
Figure 8:
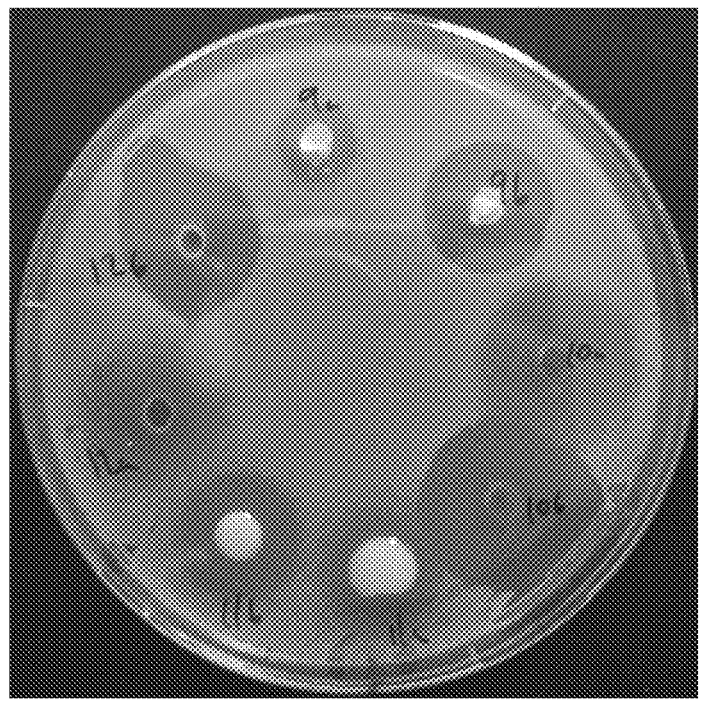
Figure 8:
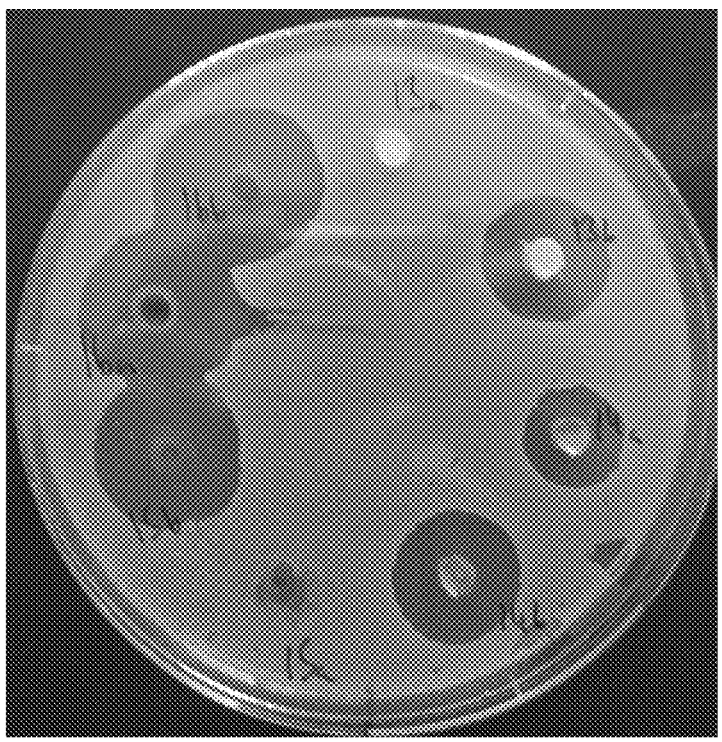
Figure 8:
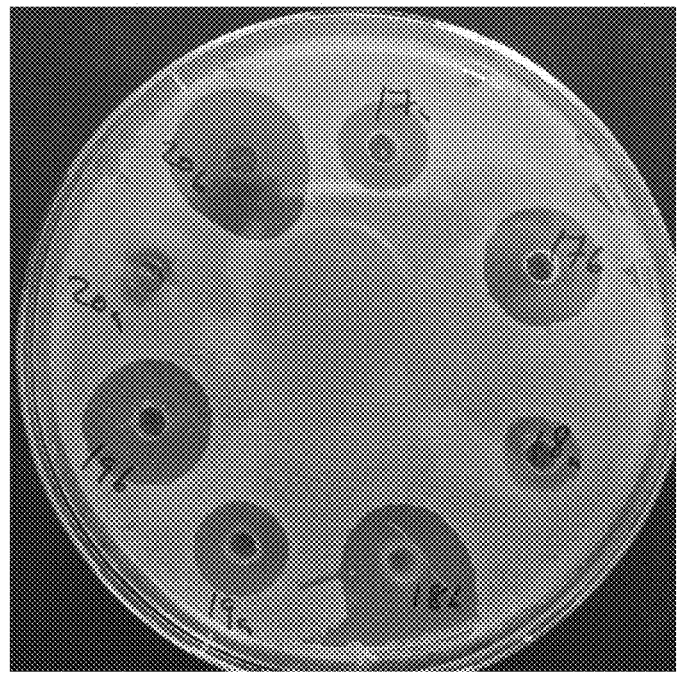
Figure 8:
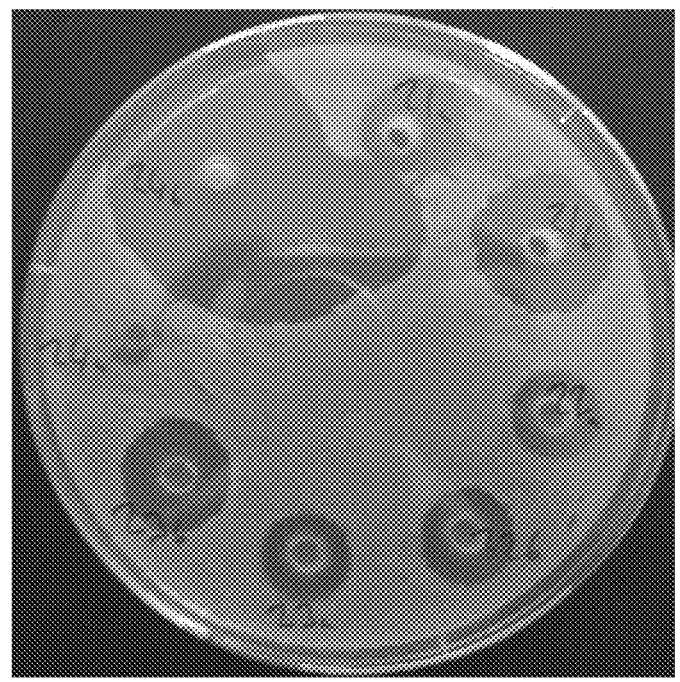

This example shows the results of tests of the antimicrobial activity of various different products on their own, and when mixed with activated honey (i.e. honey with added glucose oxidase). Antimicrobial activity against *Staphylococcus aureus* was tested in a well diffusion assay carried out as described in Example 2. The different samples tested are listed in Table 2 below, and photographs of the results are shown in FIG. 8.

TABLE 2

| Sample Number | A | B |
|---|---|---|
| 1 | Chesty Cough Syrup Formula | +10% Activated Honey powder |
| 2 | Cough Syrup with honey | +10% Activated Honey powder |
| 3 | Branded Nappy cream | +10% Activated Honey powder |
| 4 | Branded Itch Relief Cream | +10% Activated Honey powder |
| 5 | Branded hand Cream | +10% Activated Honey powder |
| 6 | Face cleanser | +10% Activated Honey powder |
| 7 | Branded smoothing facial scrub | +10% Activated Honey powder |
| 8 | Barrier Vaseline | +10% Activated Honey powder |
| 9 | Branded baby nappy cream | +10% Activated Honey powder |
| 10 | Branded gentle cleanser face wash | +10% Activated Honey powder |
| 11 | Branded face care exfoliating wash | +10% Activated Honey powder |
| 12 | Branded facial wash | +10% Activated Honey powder |
| 13 | Branded nappy care ointment | +10% Activated Honey powder |
| 14 | Antiseptic wound cream | +10% Activated Honey powder |
| 15 | Branded hand gel with Alovera | +10% Activated Honey powder |
| 16 | Branded antiseptic wound spray | +10% Activated Honey powder |
| 17 | Miel vida dulce y sana | +0.015% Glucose oxidase |
| 18 | Miel de Abejas | +0.015% Glucose oxidase |
| 19 | Pure Honey sample jars | +0.015% Glucose oxidase |
| 20 | Propolis tablets | +0.15% Glucose oxidase |
| 21 | Propolis and Honey spray | +0.015% Glucose oxidase |
| 22 | Propolis spray | +0.015% Glucose oxidase |
| 23 | Propolis dropper | +0.015% Glucose oxidase |
| 24 | Honey powder | +2% Glucose oxidase |

The results clearly show the increased antimicrobial effectiveness of the products when mixed with activated honey.

EXAMPLE 9

Figure 9:
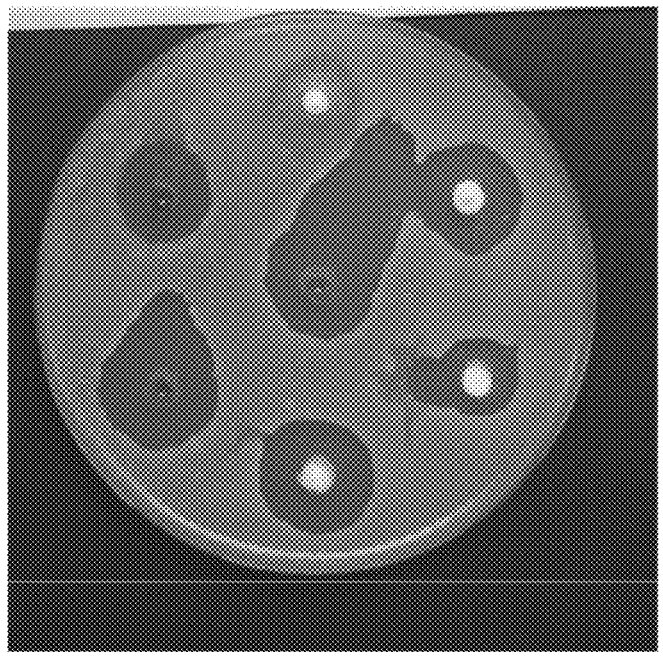
FIG. 9 shows the results from well diffusion assays for the antimicrobial effect of different products in the presence and absence of a composition of the invention.
Figure 9:
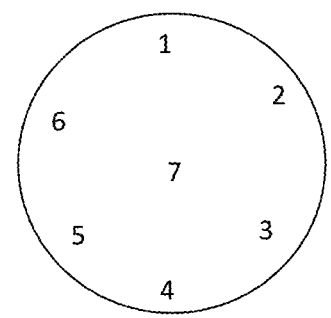
Figure 9:
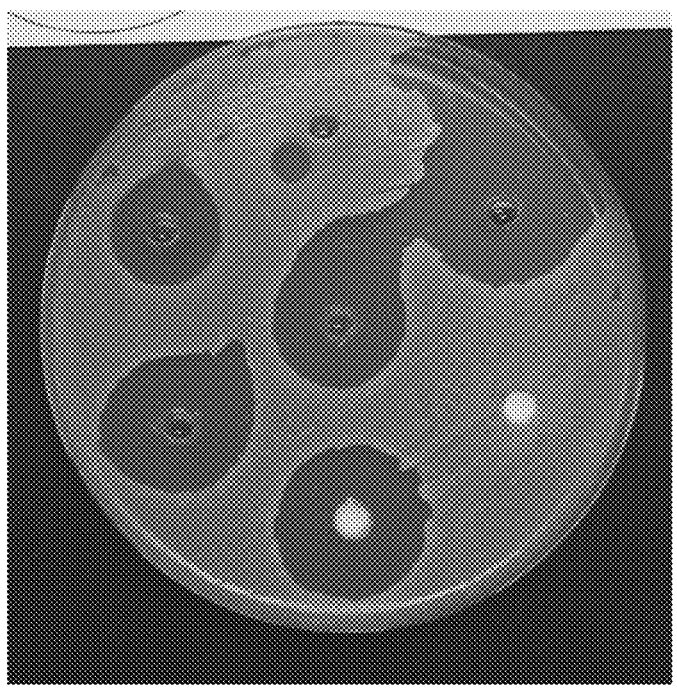
Figure 9:
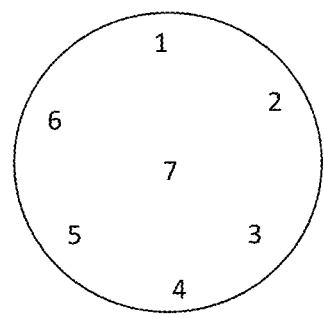

This example shows the results of further tests of the antimicrobial activity of various different products on their own, and when mixed with activated honey (i.e. honey with added glucose oxidase). Antimicrobial activity against *Staphylococcus aureus* was tested in a well diffusion assay carried out as described in Example 2. The different samples tested are listed below, and photographs of the results are shown in FIG. 9.

FIG. 9a:
1. Branded antiseptic cream #1
2. Branded antiseptic cream #1+10% Ulmo 40+
3. Branded antiseptic cream #2
4. Branded antiseptic cream #2+10% Ulmo 40+
5. TINEO Honey Active 20+
6. Manuka Honey 25+
7. Ulmo Honey Active 20+

FIG. 9b:
1. Cough syrup
2. Cough syrup+10% Ulmo 40+
3. Branded hand cream
4. Branded hand cream+10% Ulmo 40+
5. TINEO Honey Active 20+
6. Manuka Honey 25+
7. Ulmo Honey Active 20+

The results clearly show the increased antimicrobial effectiveness of the products when mixed with activated honey.

EXAMPLE 10

This example describes sterilisation of a composition of the invention that comprises unpasteurised honey and added purified glucose oxidase.

Ten sealed sachets each containing 50 g of the composition were gamma irradiated at a target dose of 11.6-14.2 kGy (the dose was 13.1-13.6 kGy as determined by dosimeters), and subsequently individually tested for sterility.

For the sterility testing, all work was carried out in a cleanroom under a laminar flow. 10 g of the same was added to 100 ml of sterile Tryptone Soya Broth (TSB: pancreatic digest of casein, 17 g/L, papaic digest of soya bean meal, 3 g/L, sodium chloride, 5 g/L, dibasic potassium phosphate, 2.5 g/L, glucose 2.5 g/L, pH 7.3±0.2) and shaken to mix, then transferred to a sterile container. A further 100 ml of TSB was added to remove any sample residue and added to the same container. TSB was added to the sample and incubated at 30° C.±2° C. for a minimum of 14 days and inspected for signs of microbial growth. Positive controls were performed on all media before testing commenced.

One positive result was noted after the full incubation period. Substantiation of 35 kGy as a sterilization dose was accepted.

Testing of sachets before and after sterilisation by gamma irradiation using a well diffusion assay similar to the assay described in Example 2 confirmed that the effect of irradiation on the antimicrobial activity of the composition was negligible. There was no observable reduction in activity level following sterilisation.

EXAMPLE 11

This example describes the results of tests demonstrating the antimicrobial effect of a composition of the invention that comprises unpasteurised honey and added purified glucose oxidase (referred to as "Surgihoney") that has been sterilised using gamma irradiation, compared with Manuka UMF 25+ honey, and a heat-deactivated honey (Non Active Honey).

Figure 10:
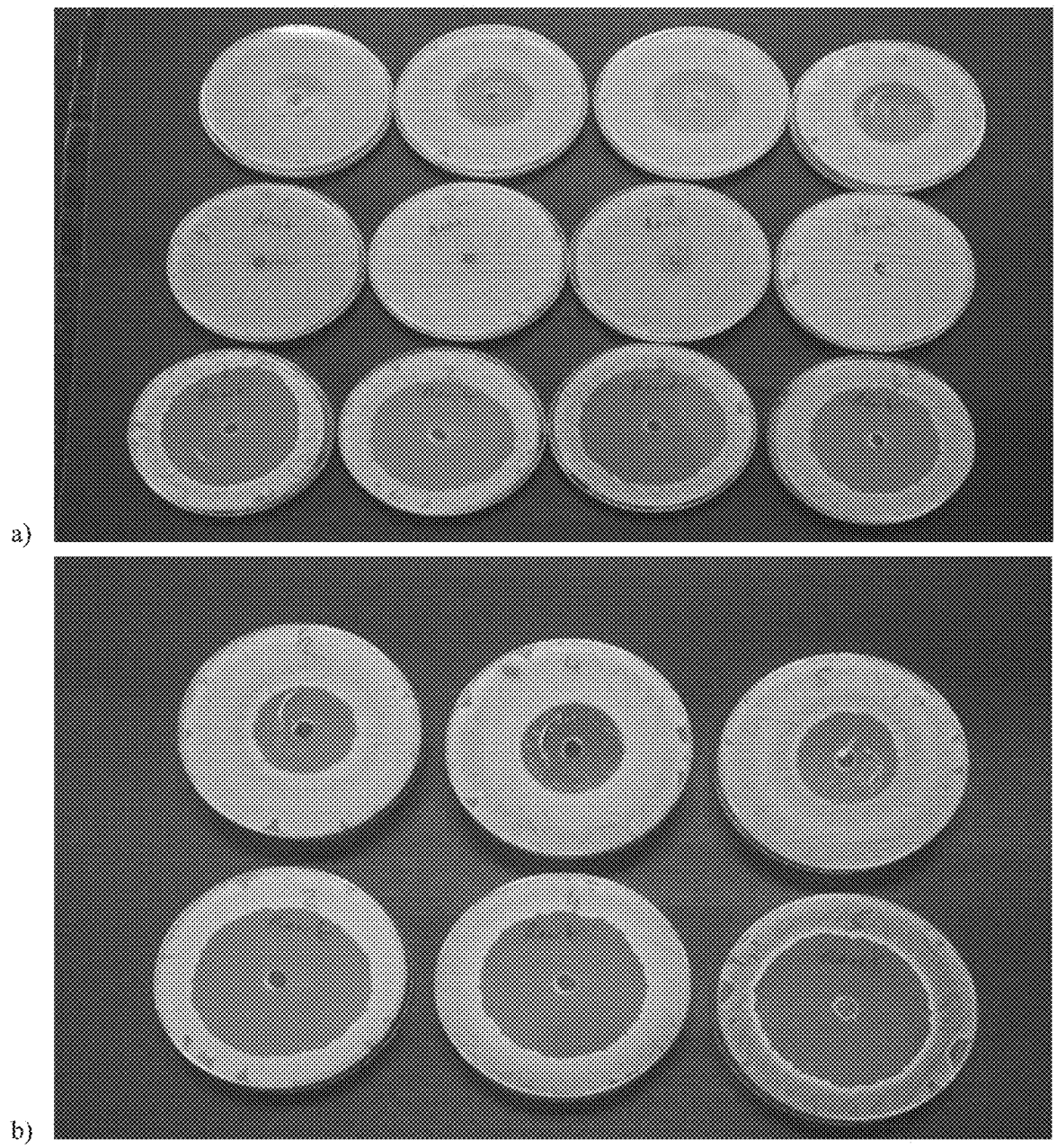
FIG. 10 shows the results from well diffusion assays for the antimicrobial effect of a sterilised honey-based composition of the invention compared with Manuka UMF 25+ honey.

Well diffusion assays as described in Example 2 were carried out using samples of Manuka honey UMF 25+, Non Active Honey, and Surgihoney. FIG. 10(a) is a photograph of agar plates showing zones of inhibition of *Staphylococcus aureus* (ATCC 9518) caused by the different samples. Manuka Honey UMF 25+ is in the top row of plates in the figure, Non Active Honey is in the middle row, and Surgihoney is in the bottom row. FIG. 10(b) shows plates treated with Manuka UMF 25+ honey (top row) and plates treated with Surgihoney (bottom row).

The results clearly show that Surgihoney retains significant antimicrobial activity against *Staphylococcus aureus* after sterilisation, and that the Surgihoney was more effective against *Staphylococcus aureus* than Manuka honey UMF 25+.

EXAMPLE 12

Stability testing of a composition of the invention that comprises unpasteurised honey and added purified glucose oxidase that has been sterilised using gamma irradiation (at a minimum dose of 35 kGy).

Accelerated aging techniques are based on the assumptions that the chemical reactions involved in the deterioration of materials follow the Arrhenius reaction rate function. This function states that a 10° C. increase or decrease in the temperature of a homogenous process, results in approximately a two times or ½ time change in the rate of a chemical reaction. For example, at 55° C., 5.3 weeks is equivalent to 1 year on-the-shelf, and at 55° C., two years would be equivalent to 10.6 weeks and five years would be 26.5 weeks.

Products from two different production batches were used for this study. Products were sachets that contained 10 g of the composition. The sachets had been sterilized at a minimum dose of 35 kGy gamma irradiation. Samples were stored, under accelerated aging conditions, at 55° C. (±2° C.).

The relationship between real time and accelerated ageing is as follows:

TABLE 3

| Real Time equivalent | Accelerated Aging @ 55° C. | |
|---|---|---|
| (Months) | Days | Weeks |
| 3 | 9 | 1.3 |
| 6 | 19 | 2.6 |
| 12 | 37 | 5.3 |
| 24 | 74 | 10.6 |
| 36 | 111 | 15.9 |
| 48 | 148 | 21.2 |
| 60 | 185 | 26.5 |

Testing, Test Intervals and Samples Required

Samples from each batch were tested at the same time intervals. The following table summarises the tests performed, and the total number of samples required at each time point for each batch.

TABLE 4

| Test | Time Intervals (Real = R; Accelerated = A) all in weeks 26 weeks | |
|---|---|---|
|  | 26R | 2.6A |
| Filled sachet weight | 10 | 10 |
| Pressure test | 10* | 10* |
| pH of honey | 5** | 5** |
| Moisture level | 5** | 5** |
| Colour | 1 | 1 |
| Sterility |  |  |
| Samples per batch | 11 | 11 |
| Total Samples | 33 | 33 |

*Use same samples as for filled sachet weight test
**Use five samples from pressure test Test Methods Filled sachet weight: An empty sachet has an average tare weight of 1.7 g. 10 sachets were weighed individually on a calibrated laboratory balance, the tare weight was subtracted, and the results were recorded.

Pressure Test: Each sachet was tested on a Pressure Test Rig in accordance with standard operating procedures. The number of passes and failures was recorded.

pH of honey: The contents of five sachets were pooled into a glass beaker. A Hanna pH meter was calibrated using three standard solutions, then the electrode was rinsed in DI water. The pH electrode and temperature probe were immersed into the honey sample and the pH value and temperature were read from the digital display, and recorded.

Moisture level: Five sachets of honey were taken from each time point. A sample of approximately 1 ml from each sachet was taken and placed on the sample plate of a refractometer (one sample at a time). The sample cover was closed and the user looked through the lens whilst pointing the instrument at a source of light such as a window. The value of the scale was read, as indicated by the line of shadow, and the result was recorded.

Colour: One sachet of honey was opened and some of the honey composition was placed onto a white tile. The colour of the honey composition was compared with the Honey Colour Chart Pfund Scale, and the score was recorded (30-800).

Results
Filled Sachet Weights—Accelerated Ageing
Batch A:

TABLE 5

| Test interval | Weight of honey in grams - total weight minus tare weight | | | | | | | | | |
|---|---|---|---|---|---|---|---|---|---|---|
| (weeks) | 1 | 2 | 3 | 4 | 5 | 6 | 7 | 8 | 9 | 10 |
| 2.6 | 10.3 | 10.3 | 10.1 | 10.2 | 10.3 | 10.3 | 10.2 | 10.3 | 10.3 | 10.2 |

Batch B:

TABLE 6

| Test interval | Weight of honey in grams - total weight minus tare weight | | | | | | | | | |
|---|---|---|---|---|---|---|---|---|---|---|
| (weeks) | 1 | 2 | 3 | 4 | 5 | 6 | 7 | 8 | 9 | 10 |
| 2.6 | 10.3 | 12.1 | 10.3 | 10.6 | 10.6 | 9.8 | 10.1 | 10.1 | 10.1 | 9.8 |

Pressure Test Results—Accelerated Ageing

TABLE 7

| Test interval (weeks) | Batch A | Batch B |
|---|---|---|
| 2.6 | 10/10 | 10/10 | pH Test Results—Accelerated Ageing

TABLE 8

| Test interval | Batch A | | Batch B | |
|---|---|---|---|---|
| (weeks) | pH | Temp (° C.) | pH | Temp (° C.) |
| 2.6 | 3.8 | 23.1 | 3.71 | 23.0 |

Moisture Content Test Results—Accelerate Ageing
Batch A:

TABLE 9

| Test interval (weeks) | Sample 1 (%) | Sample 2 (%) | Sample 3 (%) | Sample 4 (%) | Sample 5 (%) |
|---|---|---|---|---|---|
| 2.6 | 15.8 | 15.8 | 15.8 | 15.8 | 15.6 |

Batch B:

TABLE 10

| Test interval (weeks) | Sample 1 (%) | Sample 2 (%) | Sample 3 (%) | Sample 4 (%) | Sample 5 (%) |
|---|---|---|---|---|---|
| 2.6 | 15.6 | 15.8 | 15.6 | 16.2 | 16.2 |

Colour Test Results—Accelerate Ageing

TABLE 11

| Test interval | Pfund scale score | |
|---|---|---|
| (weeks) | Batch A | Batch B |
| 2.6 | 90-120 | 90-120 |

Examples 13-35 below describe the results of treatment of wounds using a composition of the invention comprising unpasteurised honey with added glucose oxidase (the composition is referred to in the examples as "Surgihoney"). The Surgihoney was provided in sealed sachets, each containing 10 g of the composition. The sachets had been sterilised using gamma irradiation. Sachets were used from day 0 of treatment. Each dressing change involved a fresh application of Surgihoney. The dressing was changed at each of the days recorded in the example, or sometimes more frequently. The Surgihoney was applied to a dressing, or directly to the wound, and then covered by a dressing. In both cases the Surgihoney was in direct contact with the wound and was covered by a dressing.

EXAMPLE 13

Figure 11:
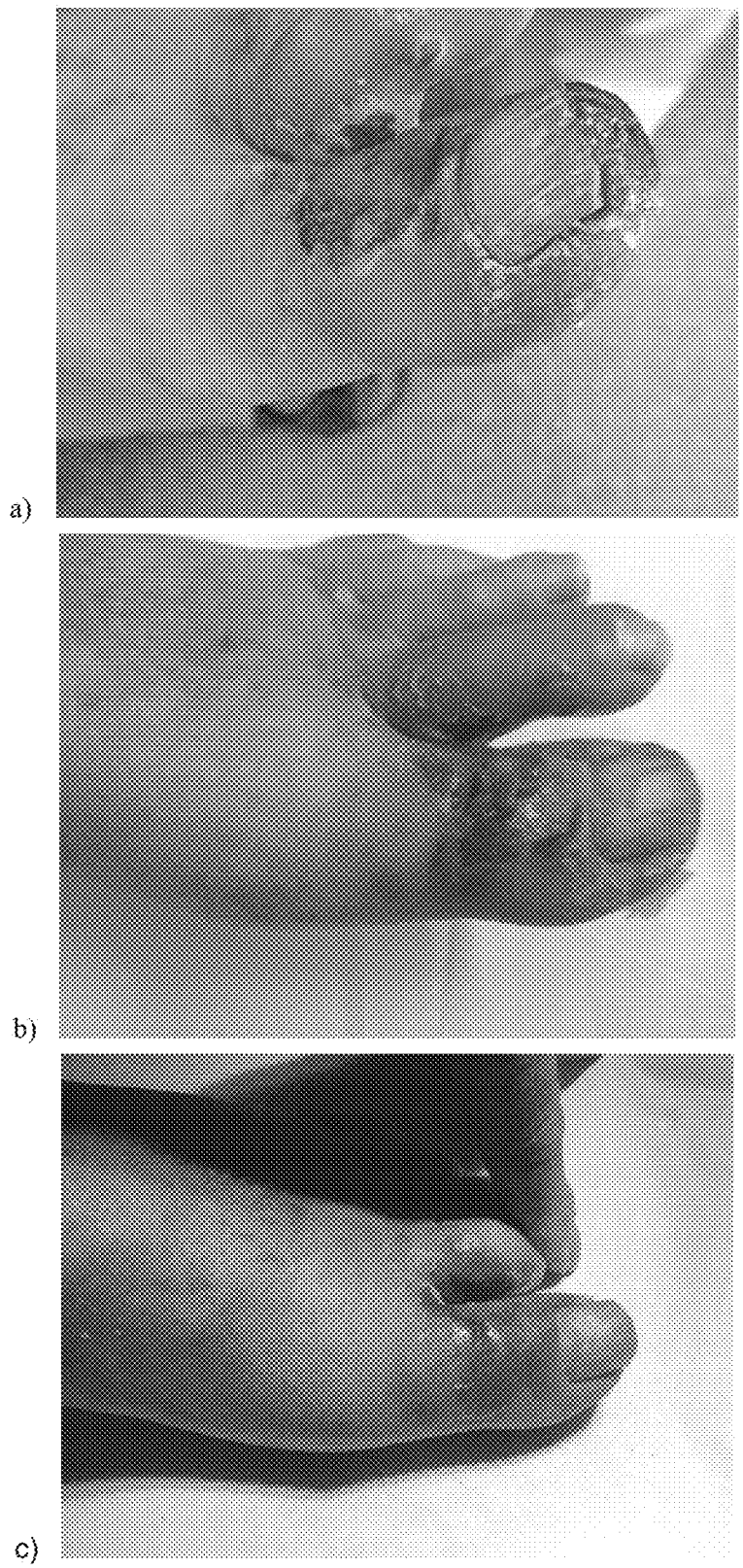
FIG. 11 shows the effect of treatment of an infected toe using a sterilised honey-based composition of the invention.

This example describes the results of treatment of an infected toe using Surgihoney. The results are shown in FIG. 11.

The patient was a 78 year old diabetic male. The wound on the left foot developed over the month before treatment began and was causing mild pain.
 a) Day 0—Wound Profile: wound: 3×2×1 cm; 99% Healthy granulation but 1% green colonisation; surrounding skin excoriated; small amount of yellow pus exudate giving off an odour;
 b) Day 5—Wound Profile: Wound improved; Second dressing change with 1 honey sachet applied each time; Metrondiazole & amoxicillin; Also Tea tree oil applied;
 c) Day 10—Wound Profile: Wound improved; Green colonisation gone; Wound cleaned, dry skin removed and further sachet of honey applied

EXAMPLE 14

Figure 12:
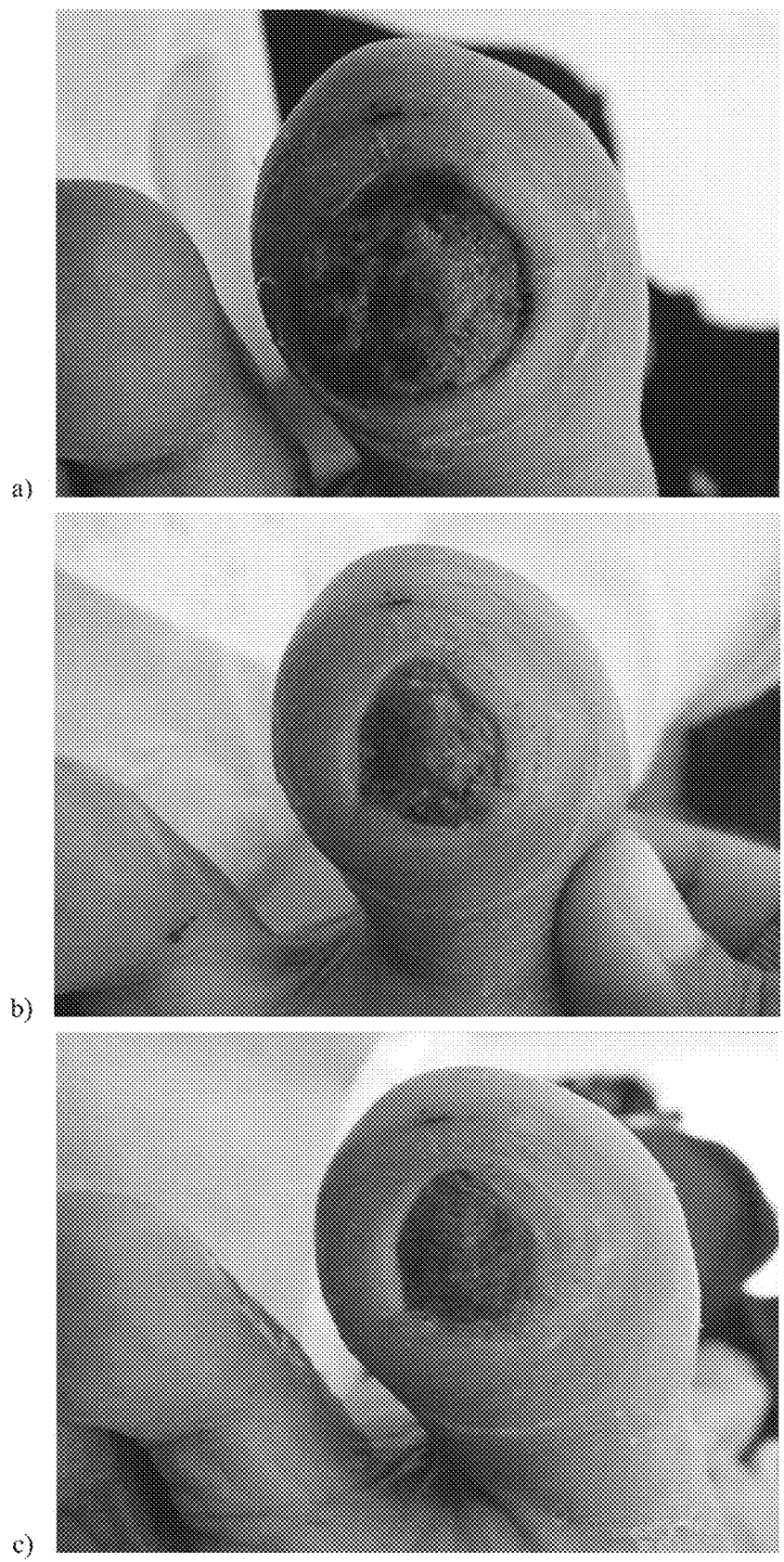
FIG. 12 shows the effect of treatment of a toe ulcer using a sterilised honey-based composition of the invention.

This example describes the results of treatment of a toe ulcer using Surgihoney. The results are shown in FIG. 12.

The patient was a 61 year old diabetic female with an infected toe ulcer on the right foot developing over a month-long period prior to treatment, and causing mild pain.
 a) Day 0—Wound Profile: Wound: 2×2×0.2 cm; 1% yellow brown slough, rest granulated tissue; Low amount of yellow exudate;
 b) Day 7—Wound Profile: Wound improved; Daily application on 0.5 sachets of Surgihoney with dressing change; Flucox;
 c) Day 10—Wound Profile: Wound improved further; Flucox stopped.

EXAMPLE 15

Figure 13:
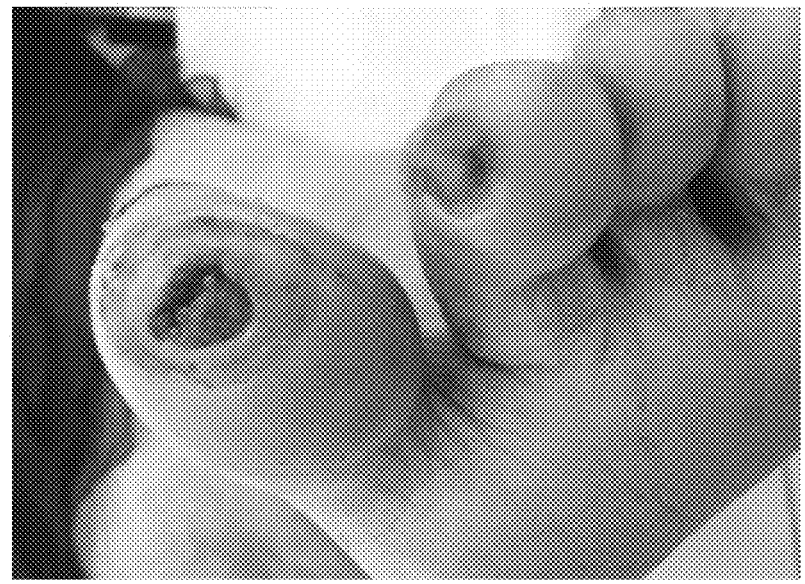
FIG. 13 shows the effect of treatment of toe ulcers using a sterilised honey-based composition of the invention.
Figure 13:
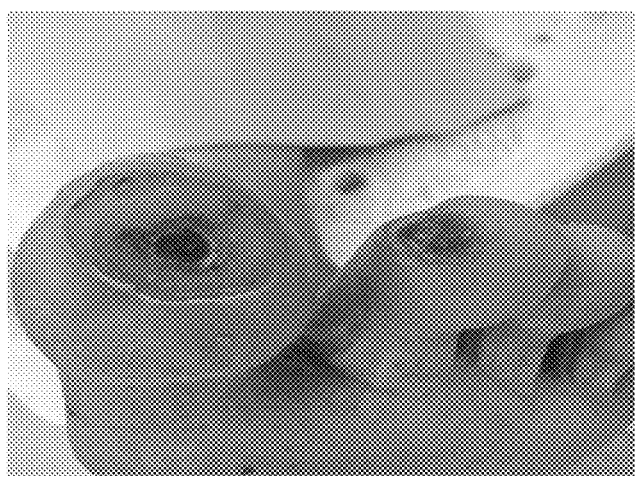
Figure 13:
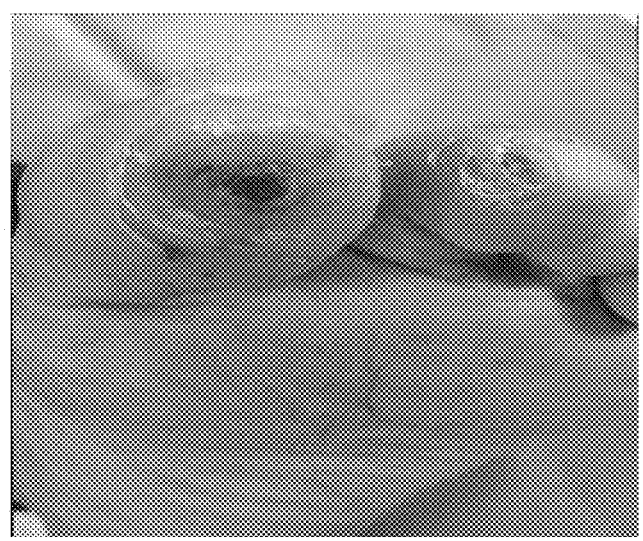

This example describes the results of treatment of toe ulcers using Surgihoney. The results are shown in FIG. 13.

The patient was a 61 year old diabetic female with toe ulcers on both 1st and 2nd toes of left foot. Mild pain.
 a) Day 0—Wound Profile: Wound: 0.8×0.8×0.2 cm; 100% Granulitic tissue; Small amount of serous exudates;
 b) Day 7—Wound Profile: Wound healed to the extent that it is no longer open; Half a sachet of honey each day; Flucox;
 c) Day 10—Wound Profile: Wound improved; Now dry, no slough or exudates; Flucox stopped.

EXAMPLE 16

Figure 14:
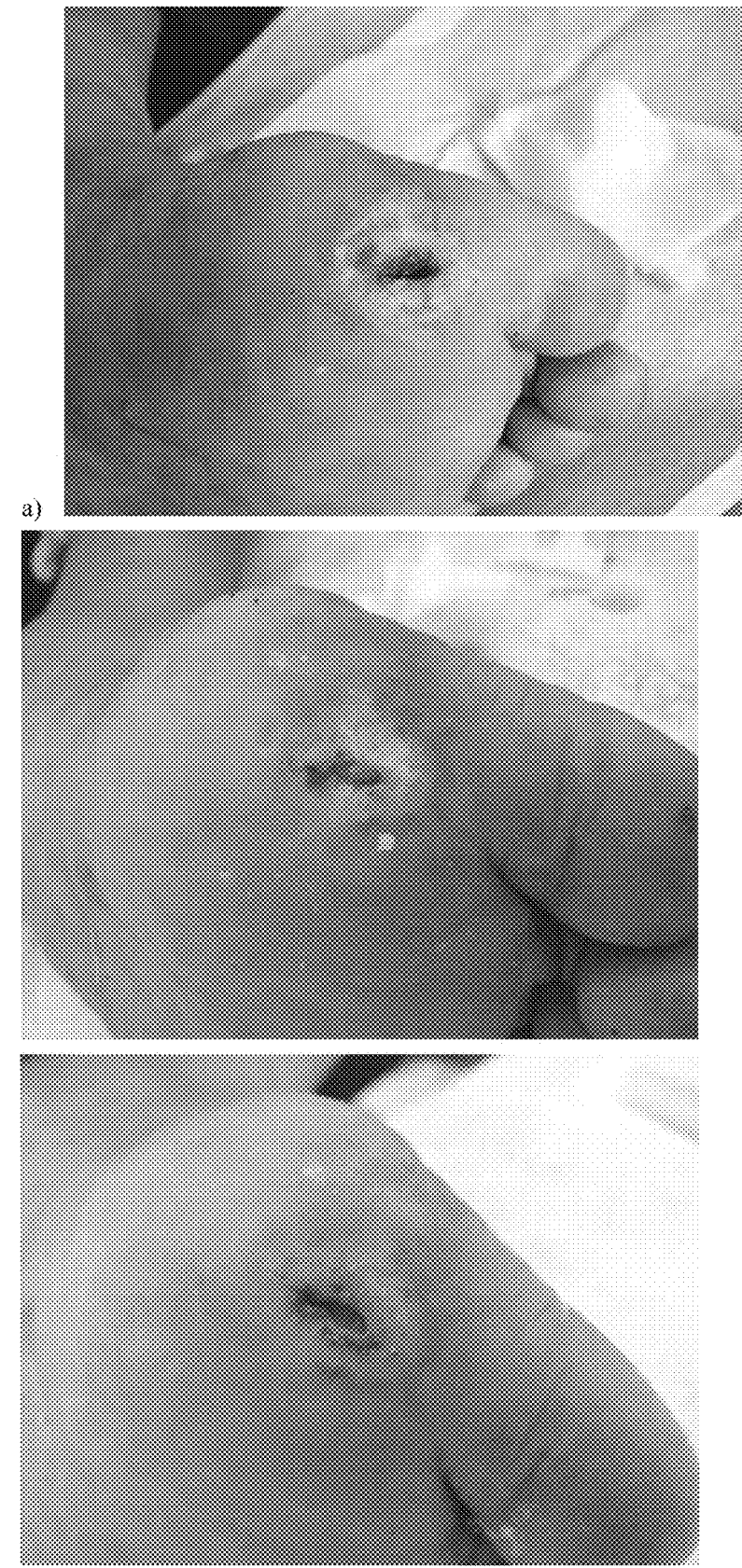
FIG. 14 shows the effect of treatment of a foot ulcer using a sterilised honey-based composition of the invention.

This example describes the results of treatment of a foot ulcer using Surgihoney. The results are shown in FIG. 14.

The patient was a 50 year old female diabetic with a foot ulcer that had developed the month before treatment. Fragile skin but no pain was reported.
 a) Day 0—Wound Profile: Wound: 1×0.5×0.5 cm; 1% yellow brown slough, rest granulated tissue; Very low amount of low, yellow exudates;
 b) Day 7—Wound Profile: Wound improved; Dry; slough replaced by healthy granulation; Size and depth reduced; Wound cleaned with saline and then honey dressing (0.5 sachet) applied; Nil antibiotics;
 c) Day 9—Wound Profile: Wound much improved; Nearly closed with no exudates present; Dressings continue to be applied with 0.5 sachets on each.

EXAMPLE 17

Figure 15:
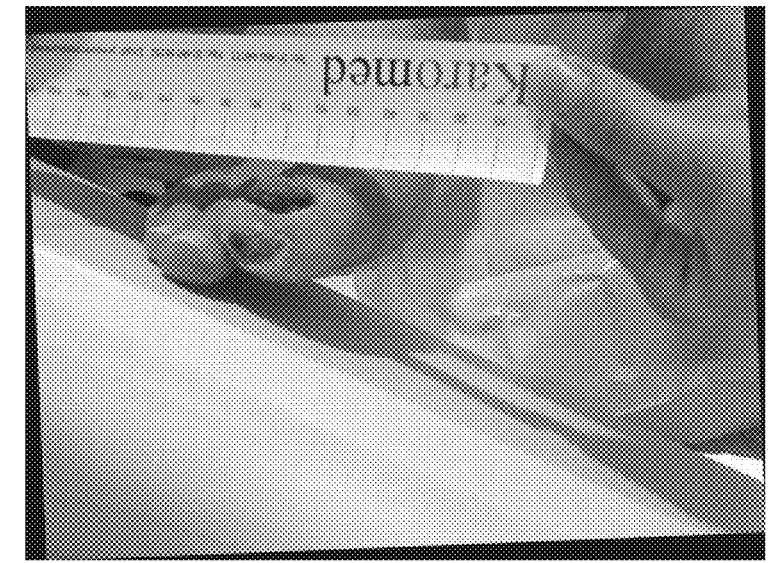
FIG. 15 shows the effect of treatment of a foot ulcer using a sterilised honey-based composition of the invention.
Figure 15:
Figure 15:

This example describes the results of treatment of a foot ulcer using Surgihoney. The results are shown in FIG. 15.

The patient was an 87 year old diabetic male with a peripheral vascular disease with a diabetic foot ulcer that had developed over more than a year. Surrounding skin was fragile though no pain apparent.
 a) Day 0—Wound Profile: Wound: 1×1.8 cm; 1% yellow brown slough, rest granulated tissue; Small amount of yellow serous exudate;
 b) Day 3—Wound Profile: Wound improved; 1 honey sachet applied with dressing change; No reports of pain; nil antibiotics;
 c) Day 6—Wound Profile: Wound improved; Wound bed now 100% granulitic tissue; Further honey sachet applied; Diprosalic on dry skin surrounding ulcer.

EXAMPLE 18

Figure 16:
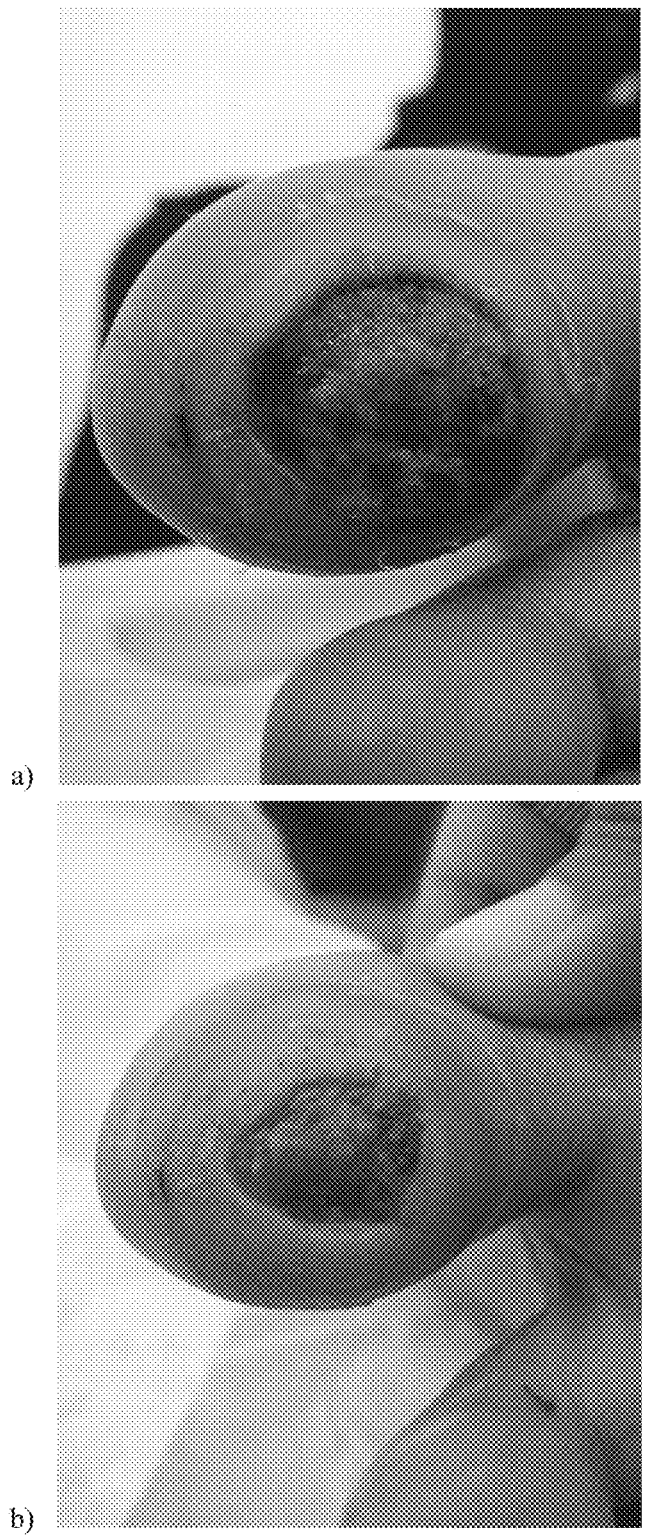
FIG. 16 shows the effect of treatment of a foot ulcer using a sterilised honey-based composition of the invention.

This example describes the results of treatment of a diabetic foot ulcer using Surgihoney. The results are shown in FIG. 16.

The patient was a male with a diabetic foot ulcer caused by poor quality shoe irritation. The patient had the ulcer less than 1 month prior to treatment.
 a) Day 0—Wound Profile: Red surrounding skim with mild pain; 1% slough, 99% granulated; Infection and diabetes; Low volume exudate, serous and yellow; Wound size: 2 cm×2 cm×0.2 cm;
 b) Day 7—Wound Profile: Assessment done in hospital but the dressing had been changed daily from day 1 until now. The dressings were changed according to the protocol by daughter in law, who is a trained nurse. Wound improved; 100% healthy granulation; Healthy surrounding skin, mild pain; Antibiotics used, Flucoxacillin, 500 mg, every 6 hours for 7 days; Wound size: 1.5 cm×1.3 cm×0.1.

EXAMPLE 19

Figure 17:
FIG. 17 shows the effect of treatment of a foot ulcer using a sterilised honey-based composition of the invention.

This example describes the results of treatment of a foot ulcer using Surgihoney. The results are shown in FIG. 17.

The patient was a 55 year old male with severe & poorly controlled diabetes. The patient had a deep ulcer at site of the third toe after amputation.
 a) Day 0—Wound Profile: Wound: 3×3×3 cm; 1% yellow brown slough; 1% green colonisation; rest granulitic tissue; Medium volume of yellow puss exudates;
 b) Day 1—Wound Profile: Wound improved; All slough removed before honey applied (1 sachet); metronidazole;
 c) Day 3—Wound Profile: Wound improved; Further sachet applied; Patient to be discharged; Swab: +++ skin flora; nil antibiotics.

EXAMPLE 20

Figure 18:
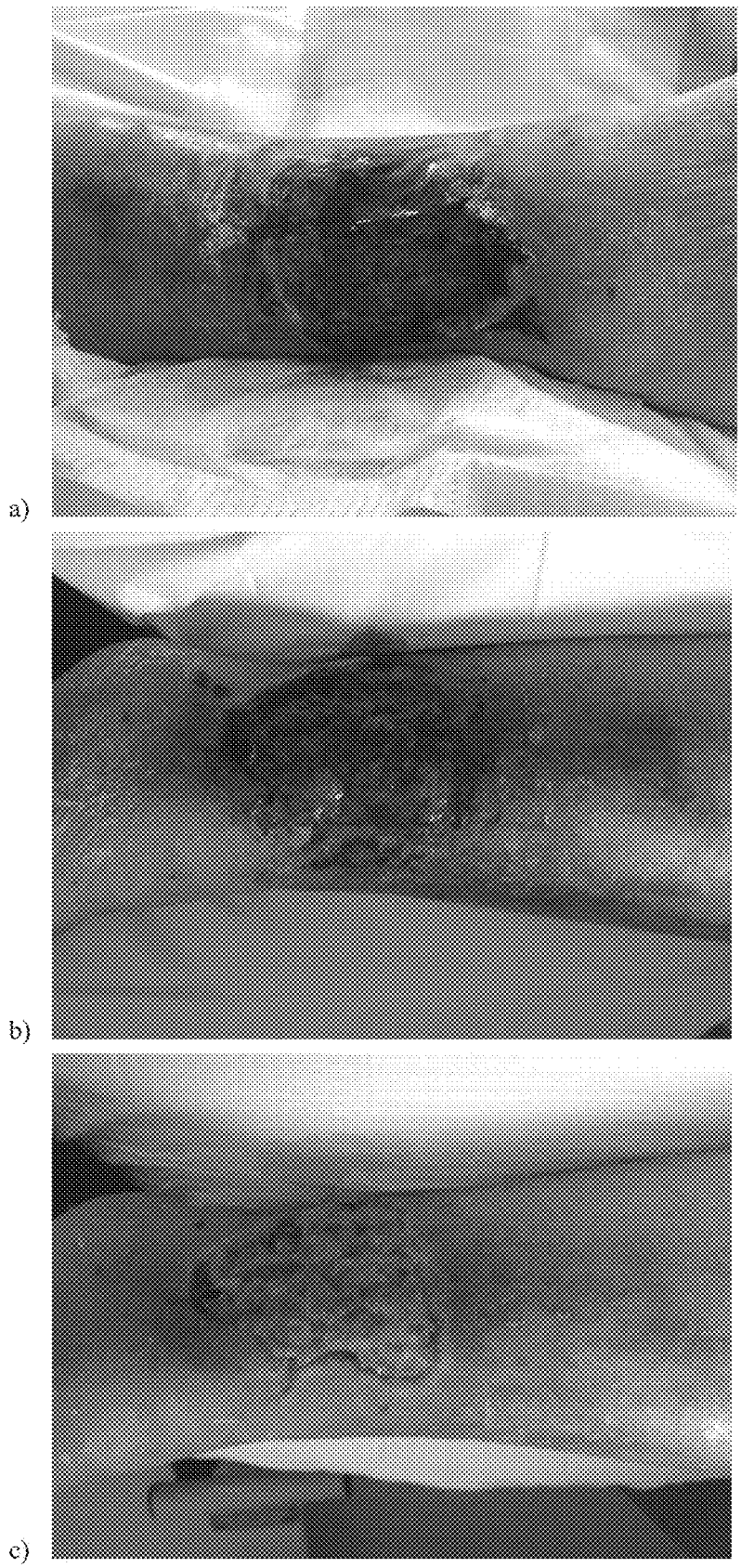
FIG. 18 shows the effect of treatment of a traumatic leg wound using a sterilised honey-based composition of the invention.

This example describes the results of treatment of a traumatic leg wound using Surgihoney. The results are shown in FIG. 18.

The patient was a 95 year old female with a traumatic wound to the lower leg that caused moderate pain.
  a) Day 0—Wound Profile: Wound: 15×12×1 cm; Mostly granulitic tissue but with 1% of wound bed necrotic and black; Medium amount of haemoserous exudate;
  b) Day 3—Wound Profile: Wound static; No further necrosis but wound much the same; 1 sachet of honey applied; Swab: *Entrecoccus* sp.; nil antibiotics;
  c) Day 8—Wound Profile: Wound improved; Lower volume of exudate and reduced necrotic tissue.

EXAMPLE 21

Figure 19:
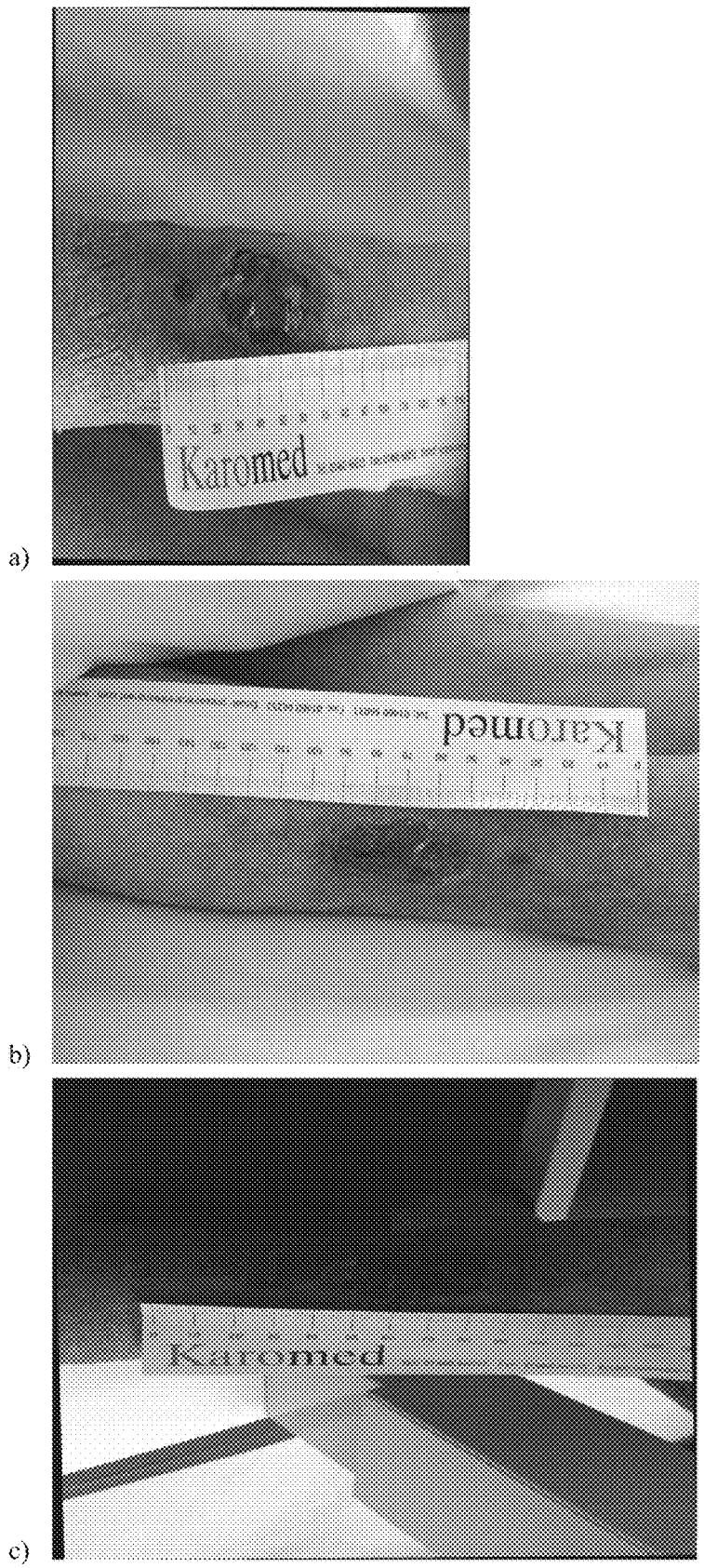
FIG. 19 shows the effect of treatment of an infected leg wound using a sterilised honey-based composition of the invention.

This example describes the results of treatment of an infected leg wound using Surgihoney. The results are shown in FIG. 19.

The patient was a 91 year old female with an infected wound to the lower leg. Surrounding skin was fragile and mild pain existed.
  a) Day 0—Wound Profile: Wound Size: 4.5×2.5 cm; Mostly red granulitic tissue with 1% yellow/brown slough; Medium volume yellow serous exudate.
  b) Day 15—Wound Profile: Wound improved; Size: 4×2 cm; Less slough and serous exudate present;
  c) Day 19—Wound Profile: Wound improved; Surgihoney applied with each dressing.

EXAMPLE 22

Figure 20:
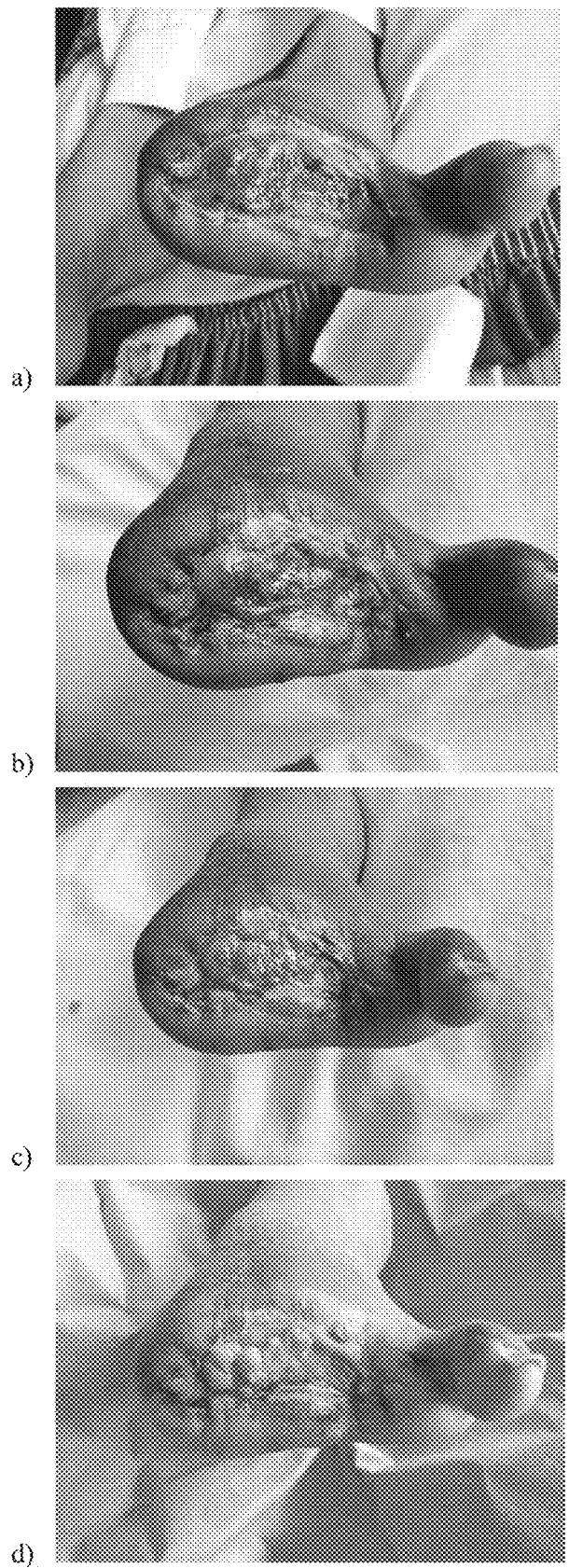
FIG. 20 shows the effect of treatment of a foot ulcer using a sterilised honey-based composition of the invention.

This example describes the results of treatment of a foot ulcer using Surgihoney. The results are shown in FIG. 20.

The patient was a 53 year old female diabetic with a chronic diabetic foot ulcer sustained after amputation of 1st, 2nd, 3rd & 4th toes.
  a) Day 0—Wound Profile: Wound: 6.5×3×0.2 cm; Granulitic tissue with low amount of yellow serous exudates;
  b) Day 5—Wound Profile: Wound size improved slightly but bed condition fairly static; Loose granulation tissue removed; Sachet of honey applied with absorbable dressing; Nil antibiotics;
  c) Day 7—Wound Profile: Wound clean with healthy granulation tissue; Dressing changed every 2 days with sachet of honey applied each time;
  d) Day 9—Wound Profile: Wound improved; Size reduced and less exudate; Patient to be discharged.

EXAMPLE 23

Figure 21:
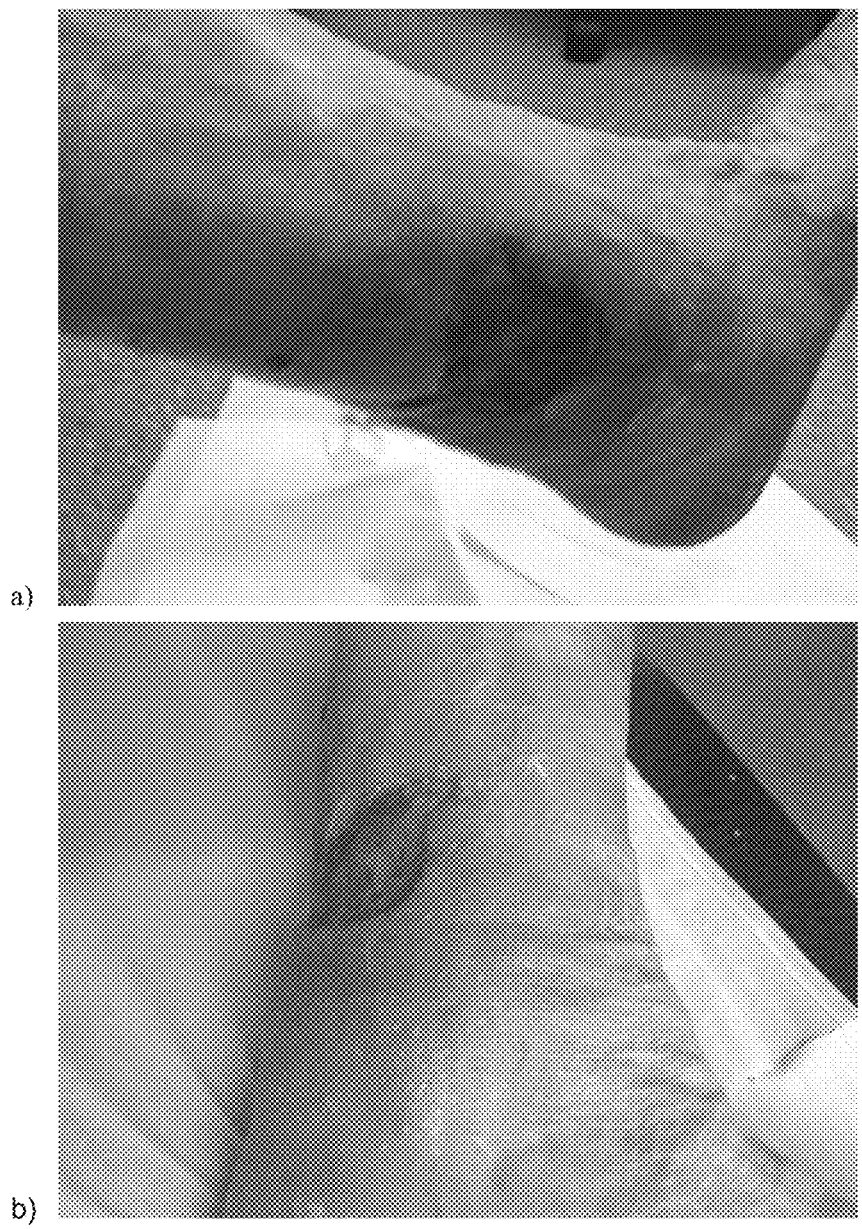
FIG. 21 shows the effect of treatment of a leg ulcer using a sterilised honey-based composition of the invention.

This example describes the results of treatment of a leg ulcer using Surgihoney. The results are shown in FIG. 21.

The patient was a female with a Leg Ulcer that had developed over the year before treatment began, and caused mild pain.
  a) Day 0—Wound Profile: Healthy surrounding skin; 1% slough, 99% granulated; Medium volume exudate, serous and yellow; Wound size: 7 cm×3 cm;
  b) Day 7—Wound Profile: Wound improved and patient in community care; 1 sachet of Surgihoney applied; Size reduced and less exudate present; Pain more bearable.

EXAMPLE 24

Figure 22:
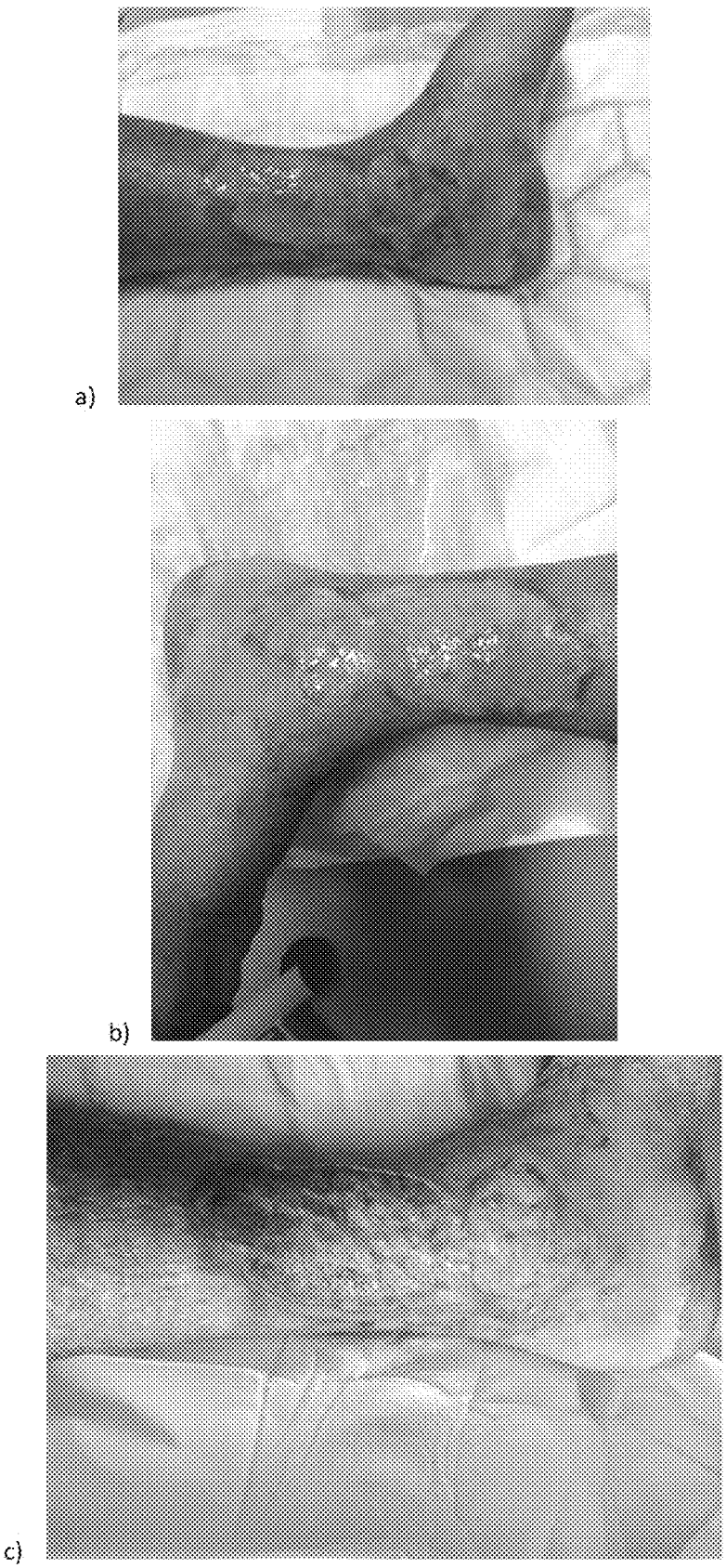
FIG. 22 shows the effect of treatment of a leg ulcer using a sterilised honey-based composition of the invention.

This example describes the results of treatment of a leg ulcer using Surgihoney. The results are shown in FIG. 22.

The patient was a 77 year old male with poor nutritional status and dehydration. Anaemia.ca prostrate. The patient had a leg ulcer that had developed over a 6-12 month period prior to treatment. Mild pain.
  a) Day 0—Wound Profile: Wound: 20×10×0.5 cm; 1% yellow brown slough, rest granulated tissue but with medium exudate, pus green; Swab: +++ mixed Coliform & *Pseudomonas*; Antibiotic: Ben Pen, Clinda;
  b) Day 4—Wound Profile: Wound static; Solely honey dressing; Ben Pen & Clinda;
  c) Day 8—Wound Profile: Wound improved; All green slough gone; Nil antibiotics; Paracetamol.

EXAMPLE 25

Figure 23:
FIG. 23 shows the effect of treatment of a leg ulcer using a sterilised honey-based composition of the invention.

This example describes the results of treatment of a leg ulcer using Surgihoney. The results are shown in FIG. 23.

The patient was a 91 year old lady with a leg ulcer that has developed over a period of 6 to 12 months. She was hospitalised and in a lot of pain.
  a) Day 0—Wound Profile: Pain severe with wound odour; Infection; 10% slough, 50% colonized green, 20% cellulitic, 20% healthy granulation; Wound: 15 cm×5 cm×0.3 cm; Exudate: Low volume, serous and yellow;
  b) Day 11—Wound Profile: Pain Mild and wound much improved; 100% healthy granulation; No infection; Wound: 10 cm×5 cm×0.2 cm; Exudate: low, haemoserous, red cm; 50% wound size reduction.

EXAMPLE 26

Figure 24:
FIG. 24 shows the effect of treatment of a leg ulcer using a sterilised honey-based composition of the invention.
Figure 24:

This example describes the results of treatment of a leg ulcer using Surgihoney. The results are shown in FIG. 24.

The patient was a 78 year old Male, UTI patient. The patient had an infected leg ulcer. Surrounding skin was macerated. The wound was causing mild pain.
  a) Day 0—Wound Profile: Wound size: 5 cm×6 cm×0.5 cm; 98% red granulitic, 1% yellow/brown slough, 1% necrotic tissue; Low volume of haemoserous red exudate;
  b) Day 8—Wound Profile: Wound improved; 1 sachet of honey applied each dressing change; Swab reveals scanty skin flora; nil antibiotics.

EXAMPLE 27

Figure 25:
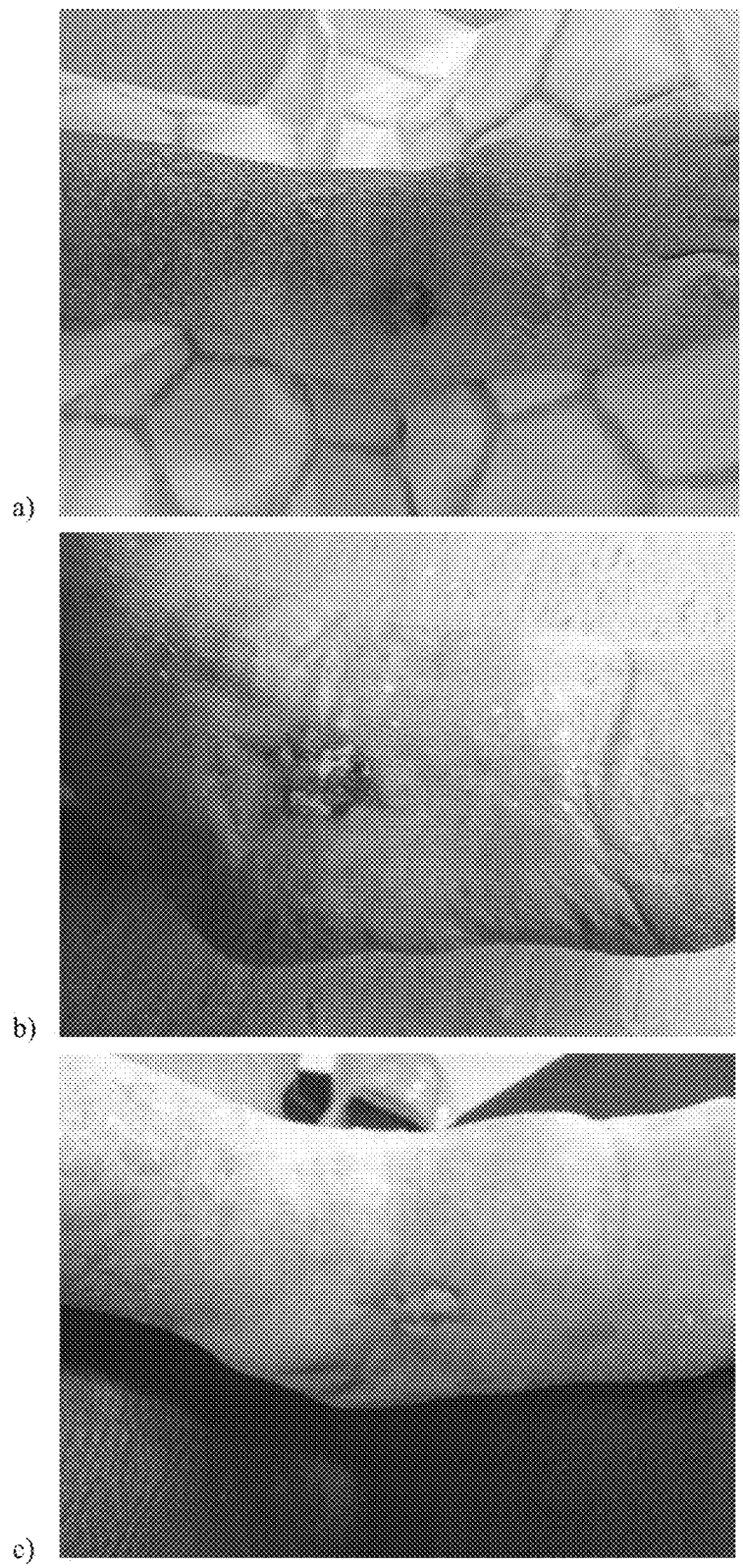
FIG. 25 shows the effect of treatment of a leg ulcer using a sterilised honey-based composition of the invention.

This example describes the results of treatment of a leg ulcer using Surgihoney. The results are shown in FIG. 25.

The patient was an 82 year old female with poor nutritional status and dehydration. The patient had a leg ulcer that had developed over the 3 months prior to treatment.
  a) Day 0—Wound Profile: Wound: 3×3×0.5 cm; Wound bed consists of healthy granulitic tissue; Small amount of yellow haemoserous exudate;
  b) Day 3—Wound Profile: Wound improved; Swab reveals +++ skin flora; 1 sachet of honey applied with dressing; nil antibiotics;
  c) Day 8—Wound Profile: Wound improved; Size of wound reduced and reduced volume of exudate.

EXAMPLE 28

Figure 26:
FIG. 26 shows the effect of treatment of a leg ulcer using a sterilised honey-based composition of the invention.

This example describes the results of treatment of a leg ulcer using Surgihoney. The results are shown in FIG. 26.

The patient was an 83 year old immobile male with low serum albumin. The patient had a leg ulcer that had developed over a 3 month period prior to treatment causing a moderate level of pain.
- a) Day 0—Wound Profile: Wound: 20×18×0.5 cm; 1% yellow/brown slough, 1% green colonisation, rest granulated tissue; Medium volume of green serous exudate; Slight wound odour;
- b) Day 4—Wound Profile: Wound improved; 2 Surgihoney sachets had been applied; ++ *Pseudomonas* on swab; No antibiotics given;
- c) Day 8—Wound Profile: Wound improved after 2 solely honey dressing changes; +++ *Pseudomonas*; Significant enough improvement to stop honey.

EXAMPLE 29

Figure 27:
FIG. 27 shows the effect of treatment of a leg ulcer using a sterilised honey-based composition of the invention.

This example describes the results of treatment of a leg ulcer using Surgihoney. The results are shown in FIG. 27.

The patient was a 74 year old male smoker with type 2 respiratory failure and poor mobility. The patient had a septic skin tear that had developed over the week prior to treatment causing moderate pain.
- a) Day 0—Wound Profile: Wound: 15×20×0.3 cm; 99% healthy granulation but with 1% critically infected; Medium volume exudate of yellow colouring; Swab reveals scanty Coliforms; Antibiotics: Clindamycin;
- b) Day 6—Wound Profile: Wound improved after 2 dressing changes; Solely honey dressing; Ulcer now dry; No growth from swabs; Clindamycin;
- c) Day 9—Wound Profile: Wound improved; Still residual cellulitis but ulcers healed; No growth on swabs once again; Clinda.

EXAMPLE 30

Figure 28:
FIG. 28 shows the effect of treatment of a leg ulcer using a sterilised honey-based composition of the invention.
Figure 28:
Figure 28:

This example describes the results of treatment of a leg ulcer using Surgihoney. The results are shown in FIG. 28.

The patient was an 81 year old male with major extensive ulcers on legs and arms. The patient had peripheral vascular disease and poor nutritional status. The wound had developed over the month prior to treatment. The surrounding skin was excoriated and causing severe pain.
- a) Day 0—Wound Profile: Wound: 30×28×1 cm; 1% yellow/brown slough, rest granulated tissue; High volume of red haemoserous exudate; Swab reveals +++mixed Coliforms & *Pseudomonas*;
- b) Day 6—Wound Profile: Wound improved; scanty *Pseudomona*; nil antibiotics but oromorph for pain;
- c) Day 10—Wound Profile: Wound improved; + *Psuedomonas* still present; Pain less severe.

EXAMPLE 31

Figure 29:
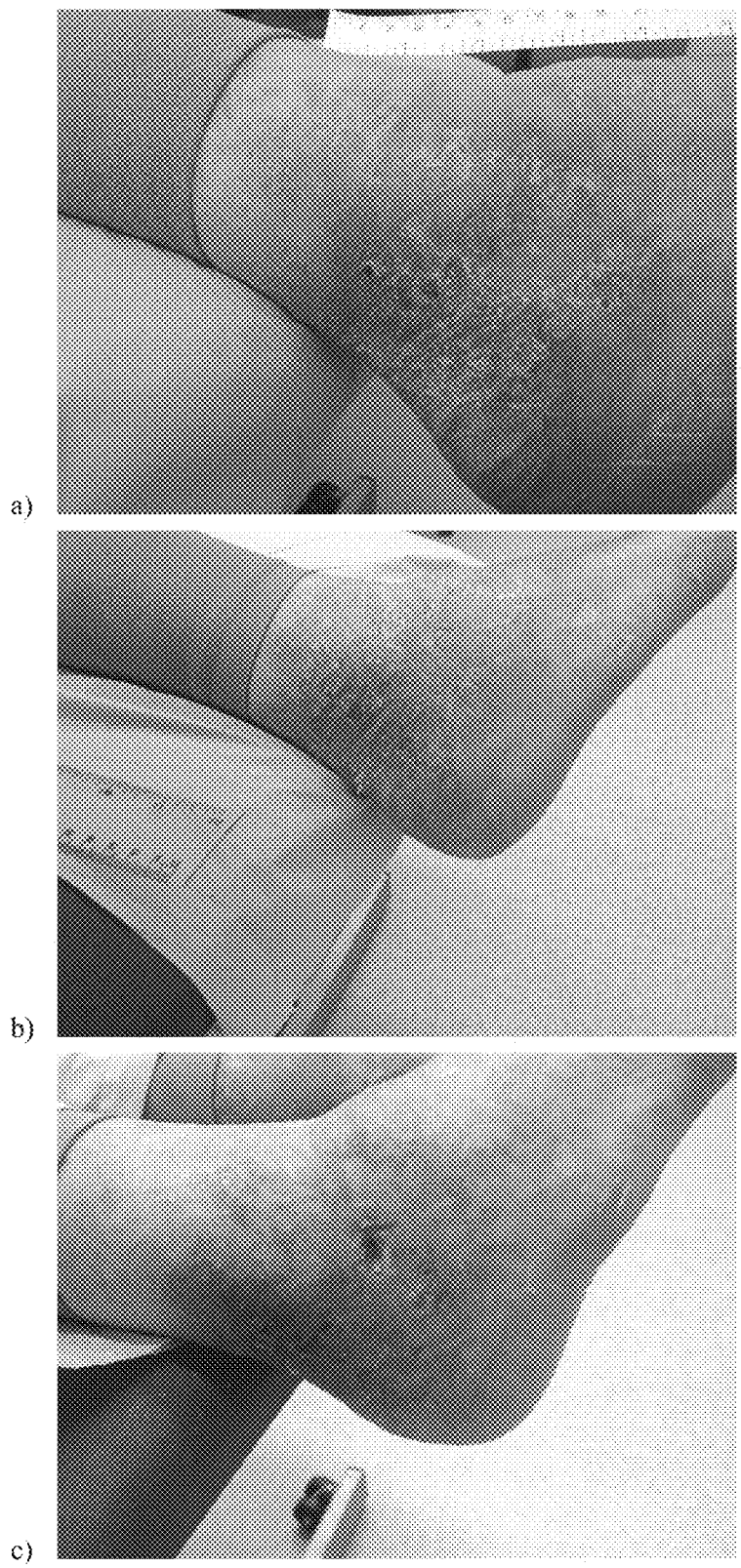
FIG. 29 shows the effect of treatment of a leg ulcer using a sterilised honey-based composition of the invention.

This example describes the results of treatment of a leg ulcer using Surgihoney. The results are shown in FIG. 29.

The patient was a 67 year old male with peripheral vascular disease. A leg ulcer had developed over the week before treatment. The surrounding skin was fragile and pain moderate.
- a) Day 0—Wound Profile: Wound: 1×1×0.2 cm; 1% yellow/brown slough, rest granulated tissue; Small amount of yellow serous exudate in wound;
- b) Day 11—Wound Profile: After series of dressing changes where wound was static, now showing signs of improvement; Lower volume of exudate, wound smaller; 1 x honey sachet applied with each change; Swab reveals staph aureus ++;
- c) Day 18—Wound Profile: Wound static; Wound size: 3×3×0.2 cm; staph aureus ++ present.

EXAMPLE 32

Figure 30:
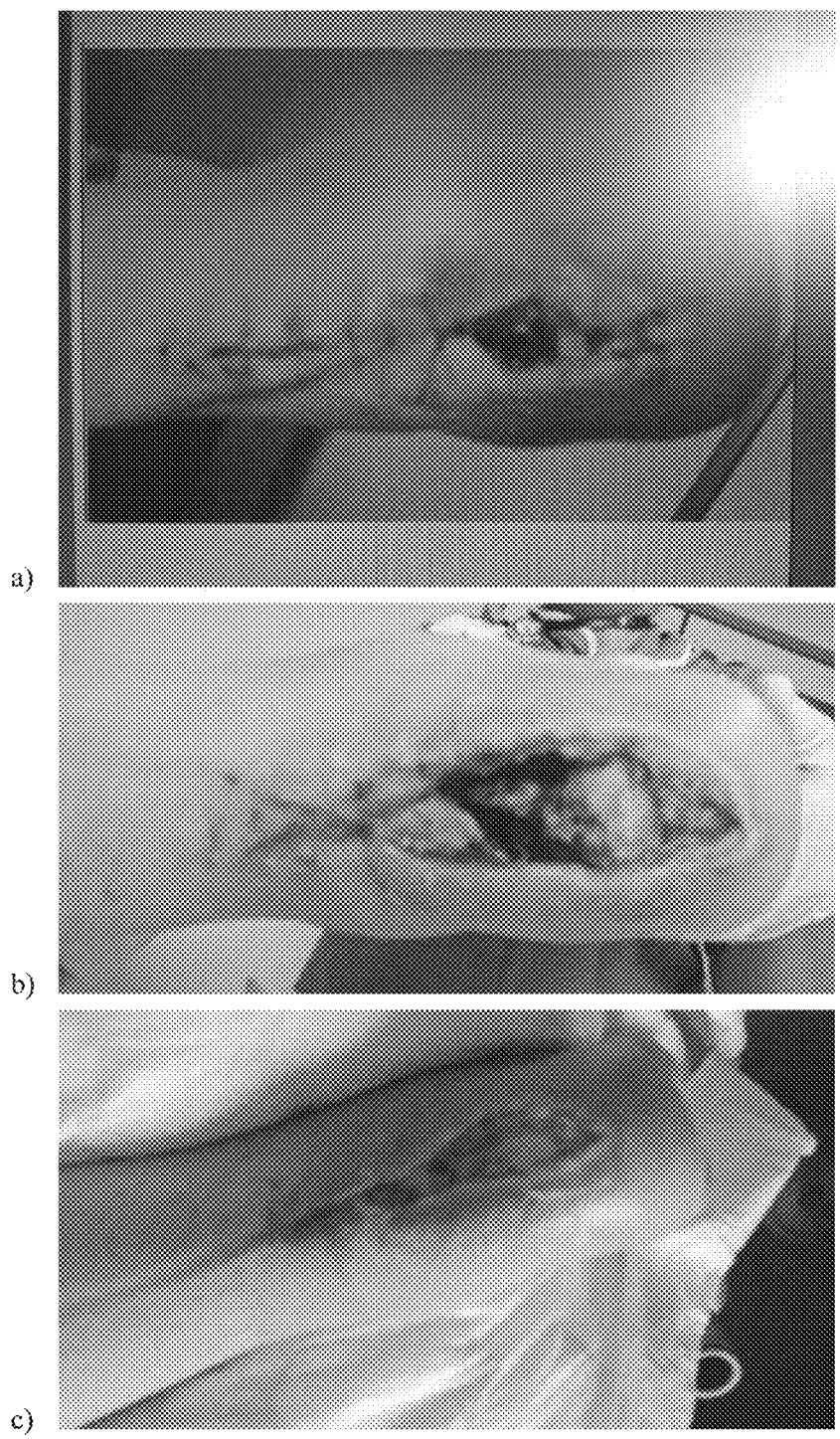
FIG. 30 shows the effect of treatment of a diabetic leg ulcer, complicated with un underlying osteomyelitis, using a sterilised honey-based composition of the invention.

This example describes the results of treatment of a leg ulcer using Surgihoney. The results are shown in FIG. 30.

The patient was a 43 old female with large diabetic ulcer that was a month old. The ulcer was complicated with an underlying osteomylelitis, bone debriefed and metal work from calcaneum. The patient had broken her foot and the subsequent treatment had lead to bone infection. The lead clinician's opinion was that the patient was very likely to have her foot amputated.
- a) Day 0—Wound Profile: Wound with 40% slough, 10% colonised green, 50% healthy granulated; Surrounding skin healthy; Moderate pain; Exudate medium, puss, yellow; Wound 9 cm×8 cm×2 com; No antibiotics;
- b) Day 1—Wound Profile: Wound static; Swab: Coliform and *Pseudomonas*; No antibiotics; No analgesic;
- c) Day 14—Wound Profile: Wound improved; 1 sachet of Surgihoney used; Wound slowly granulating, much improved; Swab: Scanty skin flora.

EXAMPLE 33

Figure 31:
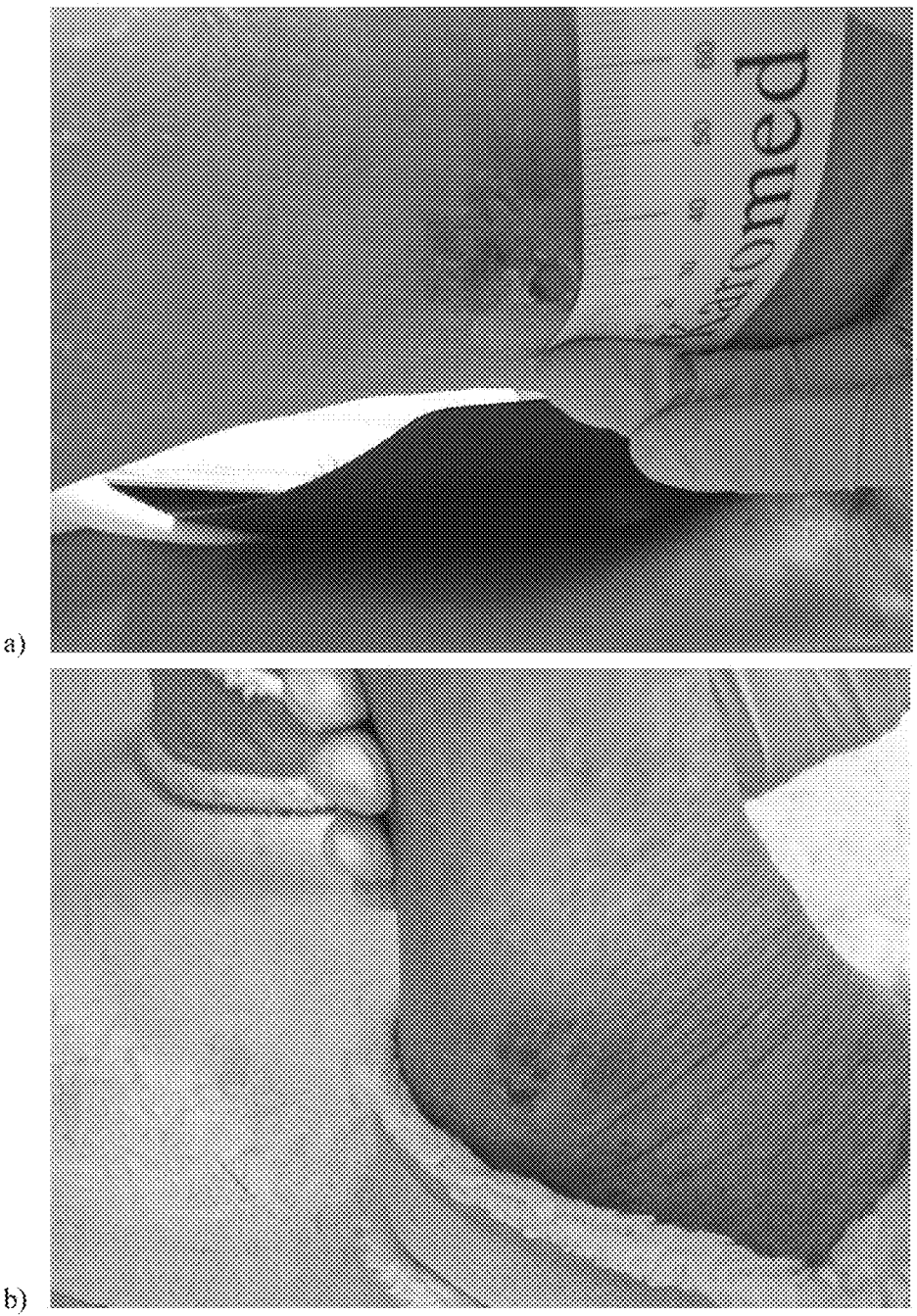
FIG. 31 shows the effect of treatment of a pressure ulcer using a sterilised honey-based composition of the invention.

This example describes the results of treatment of a pressure ulcer using Surgihoney. The results are shown in FIG. 31.

The patient was an 88 year old female diabetic with poor nutritional status. The patient had a pressure ulcer (grade 3) that had developed over the 6 month period prior to treatment, causing a moderate level of pain with fragile surrounding skin.
- a) Day 0—Wound Profile: Wound size: 0.7×0.7×0.2 cm; 1% yellow/brown slough, 1%; cellulitic tissue with rest granulitic; Low volume of yellow pus present;
- b) Day 3—Wound Profile: Wound healed (closed up); 1 Sachet of Surgihoney applied.

EXAMPLE 34

Figure 32:
FIG. 32 shows the effect of treatment of an infected armpit cut using a sterilised honey-based composition of the invention.

This example describes the results of treatment of an infected armpit cut using Surgihoney. The results are shown in FIG. 32.

The patient was a 21 year old female with an infected wound under arm. The surrounding skin was red and mild pain caused.
- a) Day 0—Wound Profile: 1% cellulitic, 99% granulated; Low volume exudate with yellow pus; Wound size: 5 cm×5 cm;
- b) Day 24—Wound Profile: Wound improved; Honey used over 2 weeks while on holiday; nil antibiotics.

EXAMPLE 35

Figure 33:
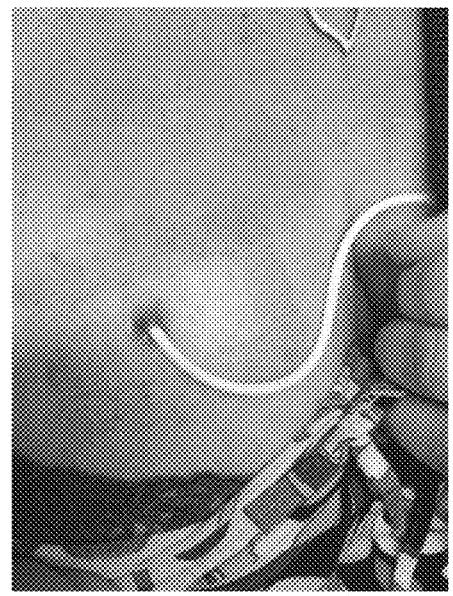
FIG. 33 shows the effect of treatment of a infection surrounding the entry point of a catheter using a sterilised honey-based composition of the invention.
Figure 33:
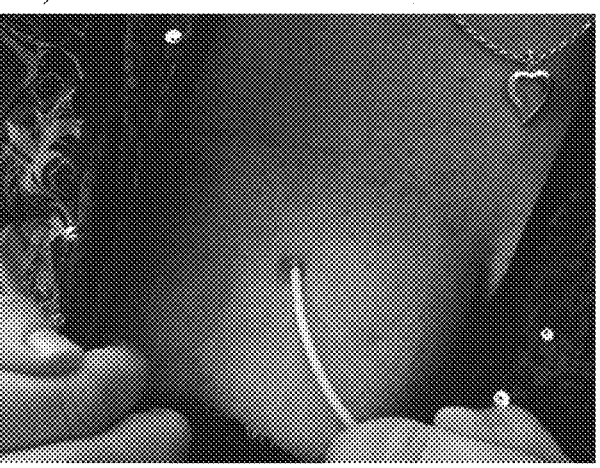
Figure 33:
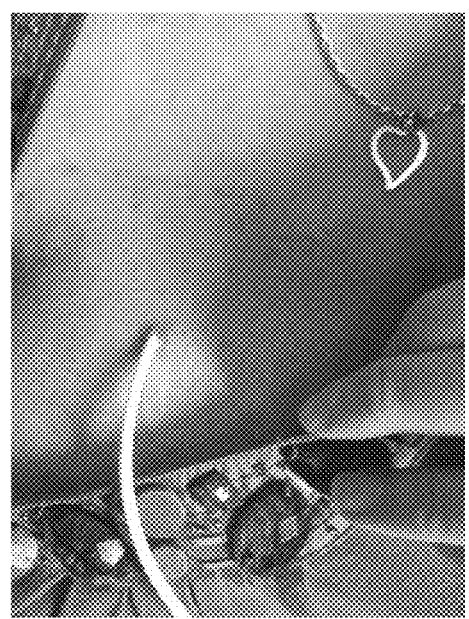
Figures 34A, 34B, 34C:
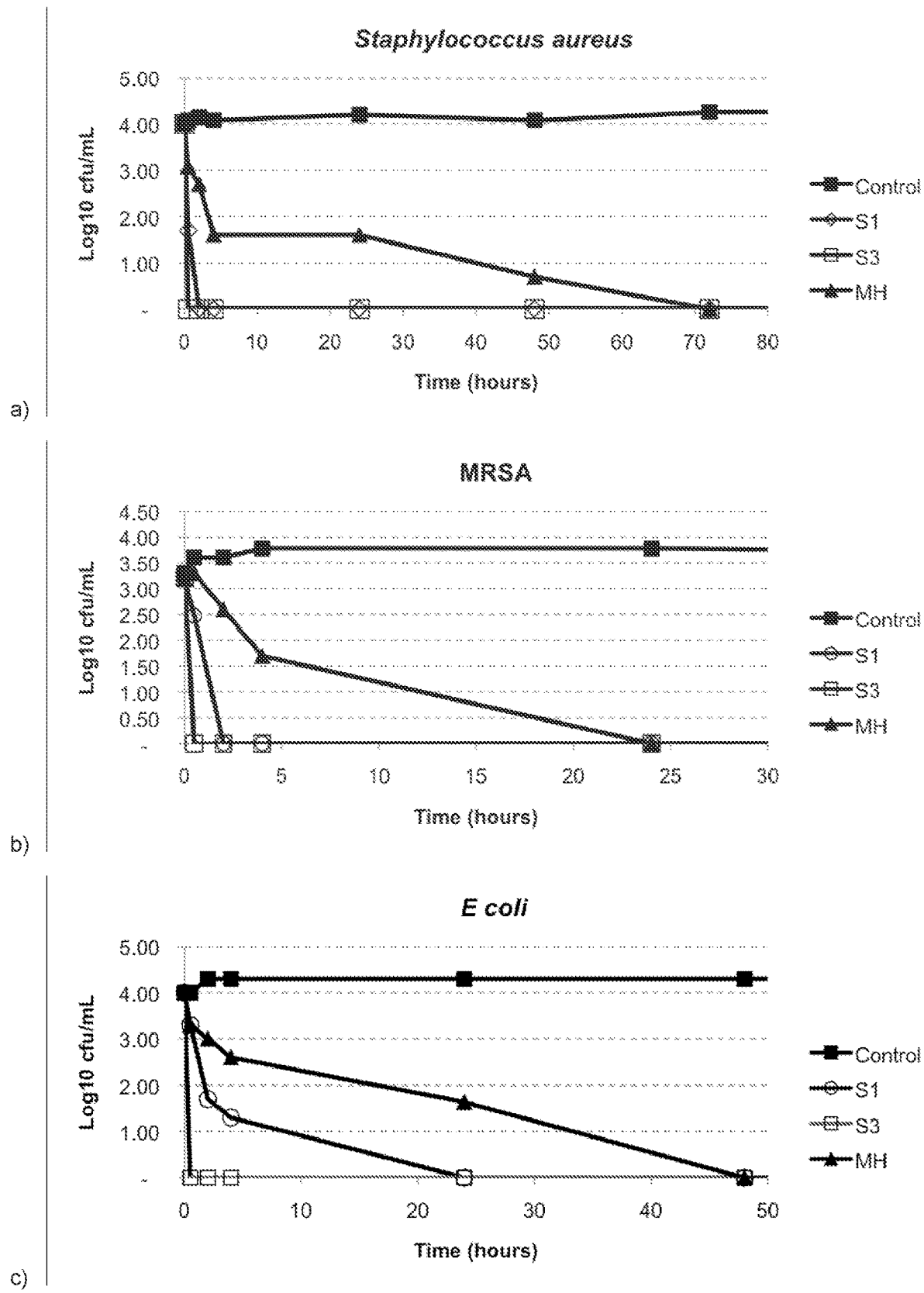
FIG. 34 shows time kill curves for Surgihoney 1 (S1), Surgihoney 3 (S3), and Medihoney (MH) for different test organisms: (a) *Staphylococcus aureus*; (b) Methicillin-resistant *Staphylococcus aureus* (MRSA); (c) *E.coli*; (d) vancomycin resistant enterococcus (VRE); (e) *Pseudomonas aeruginosa*; (f) *Klebsiella*; (g) *E.coli* ESBL; (h) *Enterococcus faecalis*.
Figure 34D:
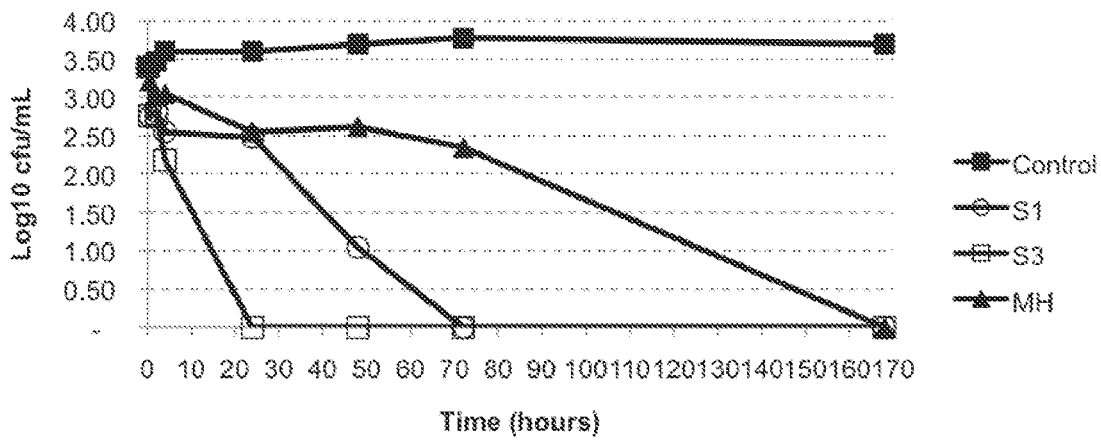
Figure 34E:
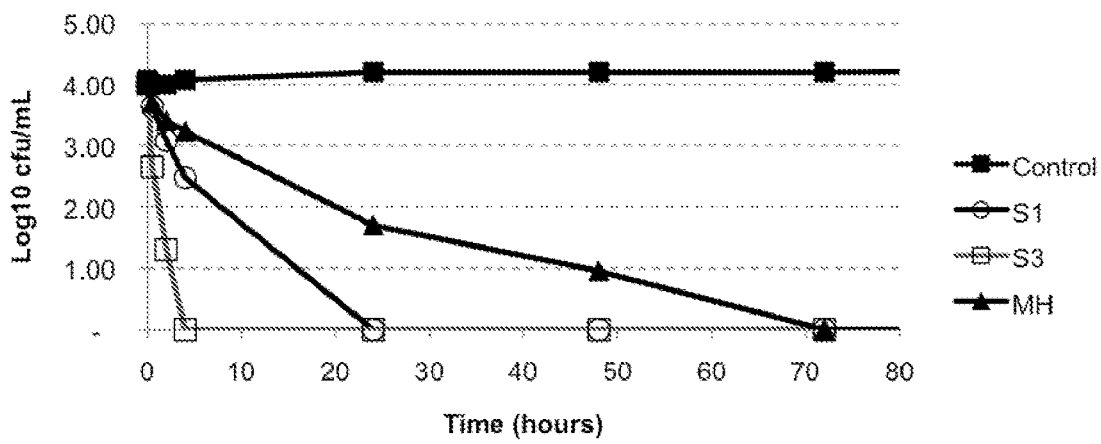
Figure 34F:
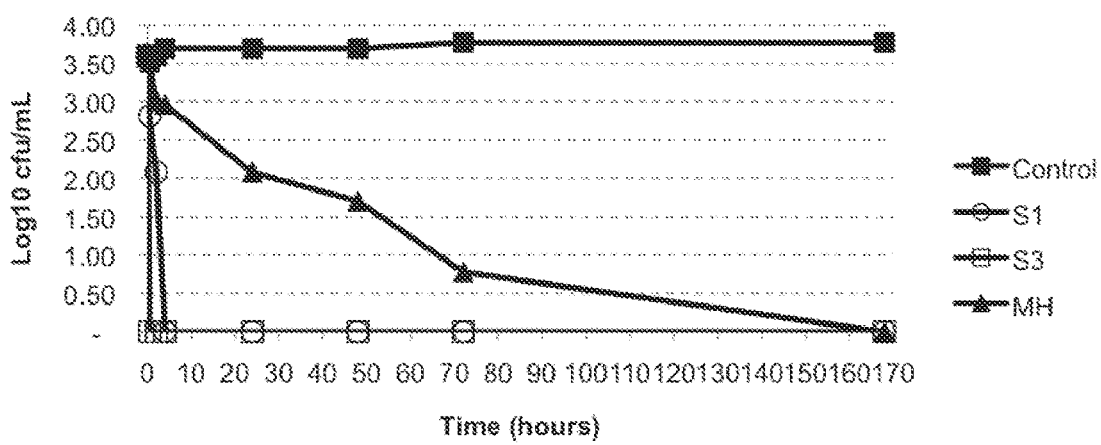
Figure 34G:
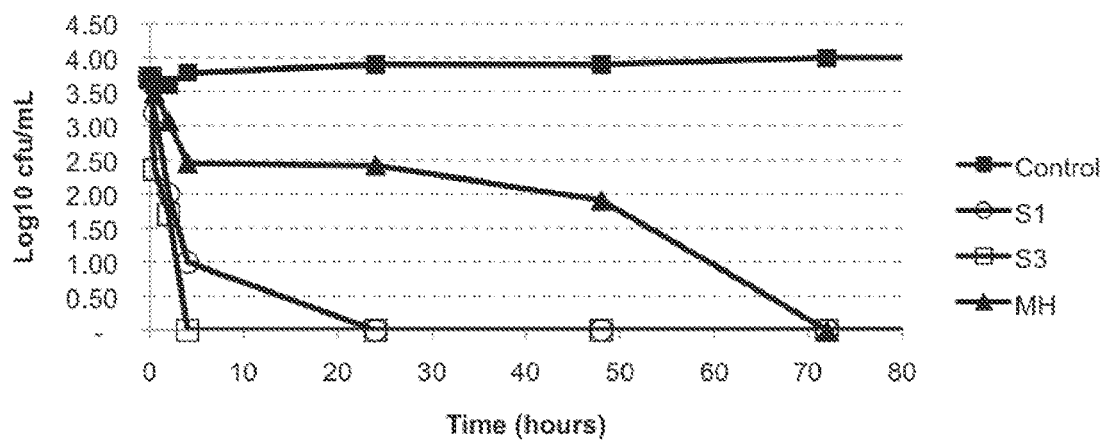
Figure 34H:
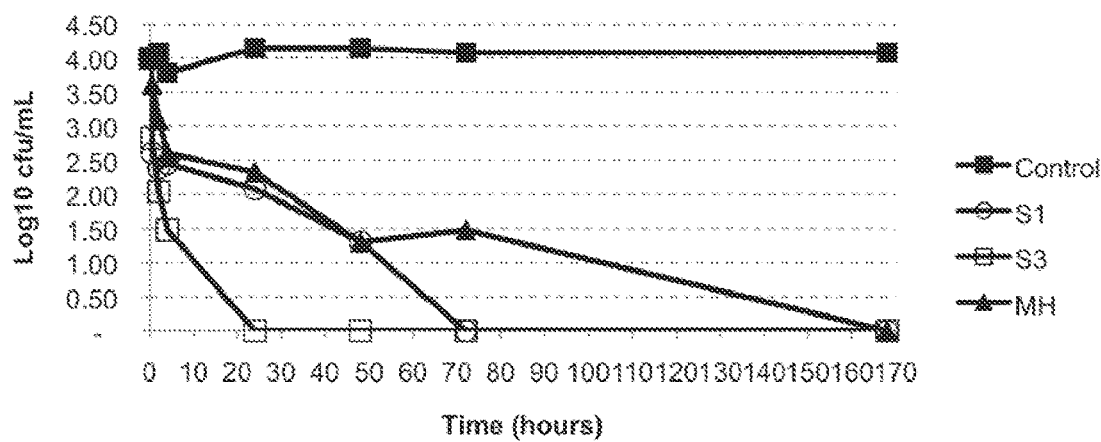

This example describes the results of treatment of infection surrounding the entry point of a catheter using Surgihoney. The results are shown in FIG. 33.

The patient was a 41 year old female cancer patient. The patient had infection of breast area surrounding entry point of catheter. The wound was less than 1 week old prior to treatment, mild pain caused.

a) Day 0—Wound Profile: Wound: 2 cm×2 cm; 1% cellulitic, rest granulated tissue; Low volume of exudate, red and serous;
b) Day 6—Wound Profile: Wound much improved; No exudates; One sachet of surgihoney applied; Swab taken but no growth; nil antibiotics;
c) Day 14—Wound Profile: Wound improved to the extent that it is no longer an issue.

EXAMPLE 36

Surgihoney

Surgihoney is unpasteurised honey with added purified glucose oxidase. Three different preparations of Surgihoney were made with different antimicrobial potencies:

S1 Surgihoney: unpasteurised honey with 0.1% (w/w) added glucose oxidase. The enzyme used was food grade glucose oxidase, from *Aspergillus niger*, from BIO-CAT, INC, activity 15,000 Units/g. Sealed sachets containing 50 g of the S1 Surgihoney were gamma irradiated at a target dose of 11/6-14.2 kGy.

S2 Surgihoney: unpasteurised honey with 0.1% (w/w) added glucose oxidase. The enzyme used was glucose oxidase (GO3B2), from *Aspergillus niger*, from BBI Enzymes Limited, activity 274 Units/mg. Unit Definition: the amount of enzyme causing the oxidation of 1 micromole of glucose per minute at 25 degrees centigrade at pH 7.0. Contaminants: alpha amylase no greater than 0.05%, Saccharase no greater than 0.05%, maltase no greater than 0.05% and GO/Cat no less than 2000.

S3 Surgihoney: unpasteurised honey with 0.25% (w/w) added glucose oxidase. The enzyme used was glucose oxidase (GO3B2) from BBI Enzymes Limited, activity 274 Units/mg.

Thus, S1 Surgihoney contains 15 units of glucose oxidase per gram of the composition, S2 Surgihoney contains 274 units of glucose oxidase per gram of the composition, and S3 Surgihoney contains 685 units of glucose oxidase per gram of the composition.

EXAMPLE 37

In Vitro Antimicrobial Activity of Surgihoney

This example describes susceptibility testing of a range of wound and ulcer bacterial isolates to Surgihoney by disc diffusion method, minimum inhibitory concentration (MIC) and minimum cidal concentration (MBC) determination, and time bactericidal measurements.

Summary

Results:

Surgihoney demonstrates highly potent inhibitory and cidal activity against a wide range of Gram positive and Gram negative bacteria and fungi. MIC/MBC's Are significantly lower than concentrations likely to be achieved in topical clinical use. Topical concentration of Surgihoney in wounds is estimated at approximated 500 gms/L. Surgihoney 1 MIC/MBC's for Staph. Aureus are 31 and 125 gms/L and Surgihoney 3 MIC/MBC's 0.12 and 0.24 gms/L. Cidal speed depends on the potency. In Surgihoney 1, the least potent, complete cidal activity occurs for all organisms tested within 48 hours. For Surgihoney 3, the most potent, cidal activity occurs within 30 minutes. Maintenance of the Surgihoney inoculums preparation for up to a week demonstrated complete cidal activity and no bacterial persistence.

Conclusions:

Surgihoney has wide potential as a highly active topical treatment combining the effects of the healing properties of honey with the potent antimicrobial activity of the bioengineered product for skin lesions, wounds, ulcers and cavities. It is highly active against multidrug resistant bacteria. It is more active than other honeys tested and comparable to chemical antiseptics in antimicrobial activity.

Superficial wounds and skin ulcers are becoming increasingly common with the rising age of the population in many countries and the global epidemic of obesity and type 2 diabetes. In the UK, community nurses spend much of their time dressing leg ulcers and supervision by leg ulcer nurses is essential if standards are to be maintained in community lea ulcer services. Most chronic breaks in the skin become colonised with bacteria. It is difficult to know when and if these are pathogenic but it is likely that even if overt infection is not present, bacterial colonisation plays a role in slowing tissue healing, establishing biofilm and resulting in wound slough and an offensive odour.

Tissue viability is challenging particularly when complicated by comorbidities. Chronic wounds always become colonised with bacteria which may destabilise the healing process. There is a temptation to send a microbiological sample and to offer systemic antibiotics when the sample is reported as growing bacteria. All this serves is to select ever more resistant microbes which is why chronic lower extremity ulcers are so often colonised with multidrug resistant organisms such as methicillin-resistant *Staphylococcus aureus* and *Pseudomonas aeruginosa*.

Surgihoney has been developed as a prophylactic dressing for wounds. This study examines the in-vitro properties of Surgihoney. Surgihoney retains all the established healing properties of natural honey but its antimicrobial activity can be set at whichever potency is required. This study determined minimum inhibitory concentrations (MIC) and minimum bactericidal concentrations (MBC) of Surgihoney 1, 2 and 3 and time kill curves.

Methods

Surgihoney was provided as potency grades 1, 2 and 3. It was presented as a sterile pharmaceutical grade product in a sachet in semisolid form.

Clinical isolates were collected from soft tissue microbiology samples. Eighteen isolates of *Staphylococcus aureus*, 12 meticillin-sensitive (MSSA) and 6 meticillin-resistant (MRSA), 6 isolates of β haemolytic streptococci, Lancefield groups A (2), B (2), C (1), G (1), 5 isolates of *Enterococcus* spp. Including vancomycin-resistant *E. faecium*, 6 of *Esch. coli*, including extended spectrum β lactamase producers, 2 of *Klebsiella* spp., 1 *Serratia Marcescens* Amp C producer, 4 of *Pseudomonas aeruginosa*, 1 of *Acinetobacter Iwoffii*, 1 of *Propionibacterium acnes*, 1 *Bacteroides fragilis*, and 2 of *Candida albicans*, 1 of *Candida glabrata*, 1 of *Aspergillus fumigates* were tested against Surgihoney.

Agar Diffusion

Six mm wells were cut in isosenitest agar which had already been inoculated with the test organism at a concentration to give a semiconfluent growth. Test Surgihoney and other honeys in the pilot study were added to the wells.

A pilot study was carried out initially to compare Surgihoney potencies S1, S2, S3 with a variety of honeys from around the world, European, South American, New Zealand, Yemani, Sudanese and with medical honey, Medihoney and with antimicrobial dressings containing silver (Silver Aquacell) and iodine (Iodoflex). Wells were cut in the plates inoculated with *Staphylococcus aureus* and filled with test honey or in the case of the dressings, these were cut to 2×2cm and placed on the surface of the inoculated plates.

Following the pilot studies the Surgihoney potencies S1, S2, S3 were tested alone against the range of bacterial isolates from skin lesions. The wells were filled to the surface with a preparation of approximately 2 gms neat Surgihoney of the three potencies, diluted and emulsified in an equal volume of sterile water. Zone sizes were measured after 18-24 hours aerobic incubation (longer for *Candida* and *Aspergillus* spp., and anaerobically for *Propionibacterium* sp. And *Bacteroides* sp.)

Minimum Inhibitory Concentrations and Minimum Bactericidal Concentrations

Surgihoney product was warmed to 37° C. to liquefy it and 5 gms was mixed with 10 mLsterile deionised water. This dilution was regarded as the 'neat' substance for serial dilution. The British Society of Antimicrobial Chemotherapy (BSAC) method for performing minimum inhibitory concentrations (MIC's) and minimum bactericidal concentrations (MBC's) was used (Andrews J M. Determination of minimum inhibitory concentrations. *J Antimicrob Chemother* 2001; 48(Supp 1): 5-16). The Surgihoney products were serially diluted in microtitre tray wells from neat to 1 in 1024. 75 μL of each honey dilution was added to each well in the strip of the microtitre tray. The neat concentration represented a concentration of 250 gm/L and the 1 in 2048 dilution, approximately 0.12 gm/L.

The test organisms were prepared by taking four morphologically identical colonies for each organism from pure culture to create a 0.5 McFarland density. This was further diluted 1:10.

All wells including controls were inoculated with 75 μL of the test isolate preparation. The well trays were incubated at 37° C. for 18 hours. The MIC was regarded as the most dilute well that showed no detectable turbidity.

The MIC well and those around the MIC well were sub-cultured on blood agar and incubated at 37° C. for 18 hours to determine the MBC. The MBC was the most dilute concentration which showed no growth after incubation.

Time Kill Curves

The test organism inoculums was prepared by taking 0.1mL of a 0.5 MacFarlane density of the test organism and inoculating this in 3mL of nutrient broth. The test inoculums was divided into 3 separate bijous, a control and three test preparations to which were added 0.5 g of Surgihoney 1 (S1), Surgihoney 3 (S3) or Medihoney (MH). Colony counts of the inocula were determined by serial dilution 1:10 and plating 0.1mL on a blood agar plate, repeated 3 times.

The test and control inocula were kept at 30° C. to simulate the temperature of a superficial skin lesion. Colony counts were performed as above in triplicate at time 0.5, 2, 4, 24, 48, 72 and 168 hours.

A terminal culture was performed by inoculating 0.1 ml of the original inoculums into nutrient broth to neutralise any residual effect of the Surgihoney and incubating for 72 hours at 37° C., before plating on blood agar to determine test organism survival.

Results

Inhibitory Zone Sizes.

The pilot comparative studies demonstrated that all the Surgihoney potencies had greater antimicrobial activity than any other honey tested including the medical grade honey, Medihoney. The inhibitory zones for S1 were larger than those produced by any other honey. Silver dressings produced some inhibitory effect beneath the dressing but there was no zone of inhibition as there was for Surgihoney. Iodine dressings produced a large zone of inhibition (approximately 70 mm) to *Staphylococcus aureus*, larger than S1 (36 mm) and equivalent to S3 (67 mm).

In the quantitative zone size testing, Surgihoney at all potencies produced an inhibitory zone in agar diffusion against all bacteria tested, both Gram positive and Gram negative bacteria including multiply antibiotic resistant bacteria, and fungal species. The zone size for each species increased with increasing Surgihoney potency preparations. Table 12. The inhibitory effect of Surgihoney was not dependant only on direct contact with the active agent as with the silver dressings, but diffused well beyond the well producing the extensive zones listed in Table 12.

MIC's & MBC's

Surgihoney demonstrated significant antimicrobial activity against all the isolates tested. MIC's and MBC's were very consistent amongst isolates of the same species whether the isolates were multidrug resistant or highly sensitive. Table 13 lists the MIC and MBC values for isolate species tested by dilution ratio and Table 14 shows the MIC and MBC's in grams per litre. The degree of potency rose with the grade of Surgihoney. The MBC for each isolate was close to the MIC within a single dilution in most cases.

Topical concentration of Surgihoney in wounds is estimated at approximately 500 gms/L. Surgihoney 1 MIC/MBC's for Staph. Aureus are 31 and 125 gms/L and Surgihoney 3 MIC/MBC's 0.12 and 0.24gms/L respectively.

Time Kill Curves.

Surgihoney kills bacteria rapidly. Starting with a colony forming units per millilitre (cfu/mL) of approximately 105, cfu/mL numbers in the control rose steadily, whereas in the Surgihoney inocula the cfu/mL fell rapidly after contact with both potencies of Surgihoney. By 30 minutes cfu numbers had fallen 1000 fold in most cases for both S1 and S3 (FIG. 34). For 51 bacterial growth was undetectable by 2 hours in most cases and for S3 by 30 minutes. Enterococci appeared more resilient and persisted for 48 hours. Cidal activity was complete for all organisms as terminal culture in nutrient broth with subsequent plating on blood agar failed to detect any organism in the S1 or S3 inocula.

Discussion

Surgihoney is natural honey which is also organic in the current sense of the word in that it has no agricultural additives or antimicrobial residues unlike much commercial honey for human consumption. It is not dependant on particular nectar sources, unlike honeys such as manuka which depends on a specific plant nectar source for its enhanced activity. The antimicrobial activity can be controlled in Surgihoney by the preparation process allowing the production of different grades with measured potency which is consistent.

This study has clearly demonstrated the efficacy of Surgihoney as a highly potent antimicrobial, active against all species of bacteria and fungi tested. In the preliminary pilot studies comparing Surgihoney with a variety of honeys sourced from around the world and with medical grade honey, Medihoney, Surgihoney demonstrated significantly greater antimicrobial efficacy. By comparison with the commonly used topical antiseptics silver and iodine, Surgihoney 3 produced an antimicrobial effect as great as iodine dressings and greater than silver dressings (Aquacel Ag) which was only effective at inhibiting bacteria in direct contact with the dressing.

MIC and MBC testing show that Surgihoney not only inhibits but also kills microbes at concentrations 10 to a 1000 fold below those that are likely to be achieved in topical treatment, estimated at 500 gms/L. The cidal activity of Surgihoney occurs at concentrations close to its inhibitory activity. There is therefore the potential for Surgihoney to be highly active in polymicrobial inhibition and eradication when applied topically in any colonised or superficially infected wounds or soft tissue cavities. As many chronic wounds are colonised with resistant bacteria, and bacterial persistence in biofilm production delays wounds healing, Surgihoney use may help reduce in appropriate use of antibiotics as well as promote wound healing. In clinical use, the topical Surgihoney concentrations at the site of the wound will be considerably higher than those for systemic antibiotics in serum or deep tissue. This is reflected in the values of the MIC and MBC's for Surgihoney, which are correspondingly higher than those generally expressed for systemic antibiotics.

The speed of cidal activity is shown by the time kill curves to be extremely rapid, within 30 minutes for Surgihoney 3 and within 2 hours for Surgihoney 1. This is the case for both Gram-positive and Gram-negative organisms, although enterococci appear slightly more resilient. Fungi, *Candida* spp. *Aspergillus* sp. also require higher concentrations and more prolonged exposure to inhibit growth and kill the organism.

Surgihoney is formulated as a sterile product to be applied as a topical wound dressing to skin lesions and cavities with the aim of providing a moist wound healing environment whilst also reducing microbial colonisation, helping to remove slough and to promote granulation and epithelialisation.

Other antimicrobial preparations are available as topical preparations intended to treat or prevent wound infections. Silver impregnated dressings appear to possess good antimicrobial activity however they also display cytotoxicity compared to honey preparations. Iodine analogues also possess good antimicrobial activity but they also have been reported to be toxic in certain situations. There is also increasing concern about the use of chlorhexidine preparations in wound dressings due to the development of antimicrobial resistance and toxicity.

The clinical utility of Surgihoney is likely to be in topical application, on skin, in wounds and cavities. Wounds may become colonised with bacteria which can form biofilms and delay healing. With increasing concern about antimicrobial resistance and the lack of novel antimicrobial agents, a topical agent with broad antimicrobial activity, could play a role in reducing the use of systemic antibiotics in soft tissue lesions. These in vitro studies have demonstrated the potential of Surgihoney as a wound dressing with high antimicrobial activity whose potency can be controlled and which also delivers other important functions in wound healing: moist barrier, desloughing, local nutrient supply, local immune modulation and is not cytotoxic.

Conclusion

These in vitro results support the clinical use of Surgihoney as a wound dressing and this may be the first product that can deliver all the required roles in the healing process of wounds as well as being a potent and non-toxic antimicrobial.

TABLE 12

Inhibitory zones sizes with different potencies of Surgihoney (S1, S2, S3)

| Bacteria | No. of strains | S1 Mean zone (range)/mm | S2 Mean zone (range)/mm | S3 Mean zone (range)/mm |
| --- | --- | --- | --- | --- |
| Methicillin-sensitive *Staphylococcus aureus* (MSSA) | 12 | 36.2 (32-38) | 53.4 (44-58) | 66.5 (60-72) |
| Methicillin-resistant *Staphylococcus aureus* (MRSA) | 6 | 35.6 (31-38) | 52.6 (48-59) | 67.3 (59-73) |
| Streptococci Beta haemolytic | 6 | 40.0 (35-42) | 44.5 (38-51) | 59.2 (53-69) |
| *Enterococcus* spp | 5 | 38.0 (34-39) | 49.5 (44-55) | 61.8 (59-64) |
| *Escherichia coli* | 6 | 33.4 (30-37) | 49.5 (36-55) | 62.7 (59-69) |
| *Klebsiella* sp. | 2 | 34.2 (30-38) | 40.0 (38-42) | 57.0 (52-62) |
| *Pseudomonas aeruginosa* | 4 | 25.8 (20-28) | 34.8 (30-38) | 50.2 (46-51) |
| *Acinetobacter lwoffii* | 1 | 32.1 | 43.7 | 55.2 |
| *Bacteroides fragilis* | 1 | 22.3 | 28.7 | 34.2 |
| *Propionibacterium acnes* | 1 | 19.7 | 23.4 | 31.9 |
| *Candida* sp. | 2 | 9 (8-10) | 15 (15) | 26 (24-28) |
| *Aspergillus fumigatus* | 1 | 8 | 12 | 18 |

TABLE 13

Serial double dilutions from neat Surgihoney (S1, S2, S3) showing dilution of minimum inhibitory concentration (MIC) and minimum bactericidal concentration (MBC).

| Organism name | S1 MIC | S1 MBC | S2 MIC | S2 MBC | S3 MIC | S3 MBC |
| --- | --- | --- | --- | --- | --- | --- |
| MSSA | 1:8 | 1:2 | 1:32 | 1:16 | 1:2048 | 1:1024 |
| MRSA | 1:16 | 1:4 | 1:32 | 1:16 | 1:2048 | 1:1024 |
| Group B Streptococci | 1:64 | 1:16 | 1:64 | 1:64 | 1:1024 | 1:256 |
| Group A Streptococci | 1:32 | 1:16 | 1:128 | 1:64 | 1:1024 | 1:512 |
| Enterococcus | 1:8 | 1:2 | 1:32 | 1:4 | 1:256 | 1:64 |
| E. coli | 1:8 | 1:4 | 1:64 | 1:64 | 1:256 | 1:128 |
| E. coli ESBL | 1:8 | 1:2 | 1:64 | 1:64 | 1:256 | 1:128 |
| Serr. liquefaciens Amp C | 1:8 | 1:4 | 1:16 | 1:4 | 1:256 | 1:128 |
| Kleb. pneumoniae | 1:4 | 1:2 | 1:32 | 1:32 | 1:256 | 1:128 |

TABLE 13-continued

Serial double dilutions from neat Surgihoney (S1, S2, S3) showing dilution of minimum inhibitory concentration (MIC) and minimum bactericidal concentration (MBC).

| Organism name | S1 MIC | S1 MBC | S2 MIC | S2 MBC | S3 MIC | S3 MBC |
|---|---|---|---|---|---|---|
| Pseud. aeruginosa | 1:16 | 1:16 | 1:64 | 1:16 | 1:256 | 1:64 |
| Candida albicans | Turbid at neat | Growth at neat | 1:16 | 1:16 | 1:64 | 1:64 |

TABLE 14

Surgihoney MIC and MBC values expressed in Grams/Litre

| Organism name | S1 MIC | S1 MBC | S2 MIC | S2 MBC | S3 MIC | S3 MBC |
|---|---|---|---|---|---|---|
| MSSA | 31 | 125 | 7.8 | 15.6 | 0.12 | 0.24 |
| MRSA | 15.6 | 62.5 | 7.8 | 15.6 | 0.12 | 0.24 |
| Group B Streptococci | 3.9 | 15.6 | 3.9 | 3.9 | 0.24 | 0.9 |
| Group A Streptococci | 7.8 | 15.6 | 1.9 | 3.9 | 0.24 | 0.48 |
| Enterococcus | 31 | 125 | 7.8 | 62.5 | 0.9 | 3.9 |
| E. coli | 31 | 62.5 | 3.9 | 3.9 | 0.9 | 1.9 |
| E. coli ESBL | 31 | 125 | 3.9 | 3.9 | 0.9 | 1.9 |
| Serr. liquefaciens Amp C | 31 | 62.5 | 15.6 | 62.5 | 0.9 | 1.9 |
| Kleb. pneumoniae | 1:4 | 125 | 7.8 | 7.8 | 0.9 | 1.9 |
| Pseud. aeruginosa | 15.6 | 15.6 | 3.9 | 15.6 | 0.9 | 3.9 |
| Candida albicans | Turbid at neat | Growth at neat | 15.6 | 15.6 | 3.9 | 3.9 |

EXAMPLE 38

Anti-Viral Activity of Surgihoney

S1 or S2 Surgihoney was mixed with Herpes Simplex Virus in cell culture medium (a 50% mixture of honey and virus in cell culture medium) and then incubated for 1 hour at 37° C. The mixtures were then plated onto cells, and the number of viral plaques formed for each mixture was recorded. Controls with no honey, or with control honey were also performed.

Figure 35:
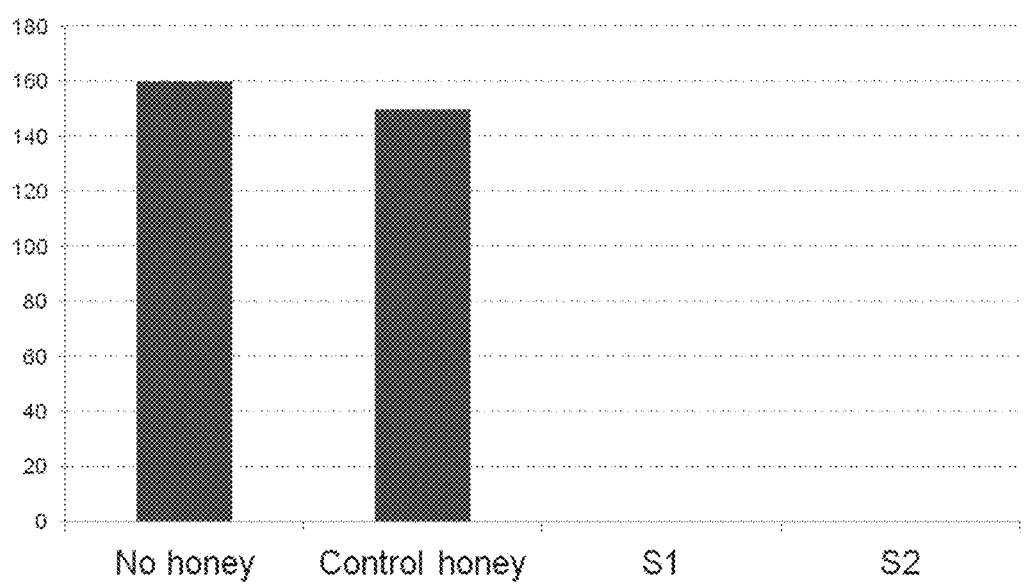
FIG. 35 shows the results of a plaque assay to test anti-viral activity of S1 and S2 Surgihoney.

The number of viral (Herpes Simplex Virus) plaques recorded after 1 hour incubation is shown in FIG. 35. No plaques were formed for the S1 or S2 Surgihoney mixtures, compared to 160 plaques for the mixture with no honey, and 150 plaques for the mixture with control honey.

The results show that both the S1 and S2 Surgihoney preparations have potent anti-viral activity.

EXAMPLE 39

Use of Surgihoney with Line Site Dressings

To assess the effectiveness of Surgihoney in preventing infection of peripherally inserted central catheters (PICC lines), S1 Surgihoney was applied topically to the line entry site in the arm of 30 patients. Approximately 3 g-8 g S1 Surgihoney was applied to a dressing, which was then contacted with the wound, and held in place by a secondary dressing. Line site colonisation and line-associated bacteraemias were assessed and compared with 30 patients who did not receive the Surgihoney dressing. The results are shown in Table 15 below.

TABLE 15

Effect of S1 Surgihoney in preventing and clearing line site colonisation

| | Surgihoney (30) | Non-Surgihoney (30) |
|---|---|---|
| Colonised at initiation | 2 | 4 |
| Colonisation during evaluation | 0 | 6 |
| Colonisation cleared during evaluation | 2 | 0 |

It was concluded that Surgihoney is an effective antimicrobial agent for use with line site dressings.

EXAMPLE 40

Use of Surgihoney to Prevent Infection of Caesarean Wounds

Infection of surgical wounds is a particular problem with Caesarean sections, which have quite a high infection rate of around 10%. There has been a national increase in Caesarean wound infection (8-24.6%) and a wide variation across NHS hospitals (13.6-31.9%) associated with the 147,726 cases of CS each year in the UK (Bragg et al., 2010. Variation in rates of caesarean section among English NHS trusts after accounting for maternal and clinical risk: cross sectional study. BMJ 2010; 341). Caesarean wound infection is a major cause of prolonged hospital stay, resource consumption, as well as other morbidities and mortality. Recovery from Caesarean section is more difficult for women who develop postoperative wound infection.

To assess the effectiveness of Surgihoney in preventing infection of Caesarean wounds, S1 Surgihoney was applied once topically to the wound post surgery. Approximately 25 g-35 g S1 Surgihoney was applied to a dressing, which was then contacted with the wound, and held in place by a secondary dressing. Nearly 200 patients were assessed over a three month period.

Clinical Evaluation

Women presenting for Caesarean section (CS) between October 2012 and January 2013 were offered Surgihoney as a dressing to the wound as a single application when the wound was dressed at the end of the procedure. Each 10 g sachet of Surgihoney was for single patient use. Using an aseptic technique a 'non-sterile' operative assistant opened the Surgihoney sachet and carefully applied the sterile contents on to the sterile dressing. The dressing was then applied to the surgical wound by the obstetrician or theatre midwife. After the procedure, the attending midwife completed an evaluation record. Data collected were MRSA status, history of diabetes, medications, and body mass index. For 14 days after the procedure the attending midwife also recorded any wound healing problems, specifically the presence of oozing, pain, inflammation. If there was any inflammation, a wound culture swab was requested and microbiological results were recorded. The surgical site infection (SSI) rate during the three months of the evaluation using Surgihoney dressing was compared with the infection rate in the 9 months prior to the evaluation based on data collected by the infection control team. Wound infection was defined clinically as an inflamed wound (erythema, swelling, discharge) which required antibiotic treatment. The rate of SSI was calculated as a percentage of all CS procedures carried out.

Results

The results are shown in Table 16 below. In the 3 month period, October 2012-January 2013, there were 186 CS's, of which 102 (55%) were emergencies. No women were colonised with MRSA. Four (2.23%) had diabetes mellitus. 42 (27.3%) had a body mass index >25. There were 4 out of 186 confirmed CS SSI during the evaluation. This represented an infection rate of 2.15%. A single patient reported an adverse event related to Surgihoney treatment in the form of wound irritation which resolved without further intervention in 3 days. In the preceding 9 months there were 590 CS procedures (234 elective and 356 emergency) and the infection control surveillance recorded 32 CS SSI, representing an infection rate of 5.42%. The reduction in infection rates is significant: p=0.042 ($\square^2$ test).

TABLE 16

Effect of S1 Surgihoney in preventing infection of Caesarean wounds

| Period | Total no of procedures | Elective (%) | Emergency (%) | No. of infected wounds | Infection rate % |
|---|---|---|---|---|---|
| January 2012 to Sept 2012 - no S1 Surgihoney | 590 | 234 (39.7%) | 356 (60.3%) | 32 | 5.42%* |
| 22 Oct 2012 January 2013 - with S1 Surgihoney | 186 | 84 (45.2%) | 102 (54.8%) | 4 | 2.15% (60% reduction) |

*From Microbiology sample data which probably under reports historic infection rates in the Trust. UK national average closer to 10%

The results show that there was a lower rate of surgical site infection (a 60% reduction) in the group treated with S1 Surgihoney compared to historic data. The Surgihoney dressing was well tolerated with few reported adverse effects.

The wound infection rates fell by 60.33% when Surgihoney was used. Using the SSI data from the two arms of the study CS SSI rates (expected) were 5.42% before Surgihoney and (observed) 2.15% after. At these levels (which are lower than the rates of infection previously reported at 9.6%) the extrapolated CS SSI infections rates for UK would be (expected) 8007 cases per year and (observed) 3176 case per year. The difference is 4831 cases that could potentially be reduced by using Surgihoney.

It was concluded that S1 Surgihoney effectively reduces the rate of infection of Caesarean wounds post surgery. Prevention of colonisation of wounds with Surgihoney, an agent which is not toxic to healing tissue and which also promotes the healing process, is a novel and potentially important finding which may change the way that surgical wounds are managed. Surgihoney offers a clinically and cost-effective intervention to significantly reduce SSI in women undergoing Caesarean section.

Discussion

This evaluation demonstrated that Surgihoney, a highly effective antimicrobial wound dressing, can be employed as a wound dressing of primary CS wounds to prevent infection. As a 'natural' product with established wound healing properties Surgihoney is likely to promote wound healing in addition to providing potent antimicrobial activity to prevent wound colonisation and infection. Some halogen-based chemical antiseptics may provide the same degree of antimicrobial activity but may delay wound healing (Jan W A. Comparison of conventional pyodine dressing with honey dressing for the treatment of diabetic foot ulcers. *JPMI-Journal of Postgraduate Medical Institute* 2012; 26(4): 402-7). Iodine wound dressings are contraindicated in CS (Joint Formulary Committee. The British National Formulary. London: The Pharmaceutical Press; 2013) and a range of toxicities are associated with their use (Pietsch & Meakins: Complications of povidone-iodine absorption in topically treated burn patients. *The Lancet* 1976; 307(7954): 280-2; Scoggin et al.: Hypernatrmia and acidosis in association with topical treatment of burns. *The Lancet* 1977; 309(8018): 959; Donovan et al.: Seizures in a Patient Treated with Continuous Povidone-Iodine Mediastinal Irrigation. *New England Journal of Medicine* 1992; 326(26): 1784; Colpaert: Iodine toxicity as a cause of total atrioventricular block in burn patients. *Burns* 2009; 35: S45-S6; Ramaswamykanive: Cardiovascular collapse following povidone-iodine wash. *Anaesthesia and Intensive Care* 2011; 39(1): 127-30; Lakhal: Povidone iodine: Features of critical systemic absorption. *Annales Francaises d'Anesthesie et de Reanimation* 2011; 30(7-8): e1-8):e1-e3.).

Similarly, Cochrane systematic reviews showed there was insufficient evidence to establish whether silver-containing dressings or topical agents promote wound healing, prevent wound infection (Storm-Versloot et aL: Topical silver for preventing wound infection. *Cochrane Database of Systematic Reviews* 2010) or are effective treatments of infected or contaminated chronic wounds (Vermeulen et al.: Topical silver for treating infected wounds (Review). *Cochrane review* 2010; (10): 42).

Although previous systematic reviews on the clinical effectiveness of honey as a wound dressing have shown equivocal evidence of benefit, this new preparation appears to offer significant clinical benefits in CS patients (Jull et al.: Honey as a topical treatment for wounds: *The Cochrane Collaboration,* 2009; Jull et al.: Honey as a topical treatment for wounds. *Cochrane database of systematic reviews* (Online) 2013; 2). In a temporal comparison of wound infection rates the evaluation has shown a 60.33% reduction in infection rates from 5.42% prior to the intervention to 2.15% using Surgihoney.

Healthcare associated infections are a significant and costly healthcare complication with approximately 8% of patients in hospital and SSIs accounted for 14% of these infections and nearly 5% of patients who had undergone a surgical procedure were found to have developed an SSI. SSIs are associated with considerable morbidity and over a third of postoperative deaths are related, at least in part, to SSI. Antimicrobial prophylaxis is routinely employed in many surgical procedures to reduce surgical wound infection. While skin disinfection is also routinely used by surgeons to reduce the skin bacterial load prior to skin incision, it has not been routine practice to use antimicrobial dressings. A reason for this may be that most topical antiseptics have a deleterious effect on tissue healing.

Surgihoney is a product with potent antimicrobial activity, which is non-toxic and promotes tissue healing. Application of this product topically to 'clean' surgical wounds could actually replace systemic antibiotic prophylaxis in certain types of surgery. Such an advance would assist the reduction of antibiotic volume use and the selection pressure on colonising bacteria.

Caesarean wounds were chosen in this evaluation because the patients are by and large healthy with no, or very few co-morbidities, and CS infection rates are reported to be increasing. Possible reasons for this increase have been an increase in older mothers, mothers with co-morbidities, particularly diabetes and a general increase in mothers with higher body mass index. While it has not previously been routine to use an antimicrobial agent in the primary wound dressing, this evaluation has shown an interesting and effective role for Surgihoney in the prevention of CS wound infections.

EXAMPLE 41

Use of S1 Surgihoney to Treat an Infected Leg Ulcer

The patent was a 52 year old male with diabetes and chronic kidney disease. The ulcer was extensive, painful, smelly and generating a high volume of serious exudates.

S1 Surgihoney was used as a topical dressing alongside antibiotics. By day 7, wound odour had reduced, pain was removed, and a high volume of serious exudate and *pseudomonas* infection had been eliminated. The patient was discharged at day 7.

Photographs of the results are shown in FIG. 36, in which: (a) shows day 1 of treatment; (b) shows day 4 of treatment; and (c) shows day 7 of treatment.

EXAMPLE 42

Use of S1 Surgihoney to Treat a Pressure Sore

The patient was a 50 year old female patient with spina bifida who was disabled and immobile. The patient had a pressure sore in the lower back down to the sacral bone which had persisted for over 1 year. The cavity was infected with *Streptococcus pyogenes*.

S1 Surgihoney was used as a topical dressing. Wound improvement was reported from day 2. By day 30, the soft tissue cavity had almost completely healed. No *Streptococcus* was detected at this point.

Photographs of the results are shown in FIG. 37, in which: (a) shows day 1 of treatment; and (b) shows day 30 of treatment.

EXAMPLE 43

Antimicrobial Activity of Surgihoney

The antimicrobial activity of Surgihoney (SH) and two prototype modified honeys made by *Apis mellifera* (honey-bee) against *Staphylococcus aureus* (NCIMB 9518) was tested. We also examined a number of modified types of Surgihoney for the ability to change the level of production of hydrogen peroxide from the samples.

Methods:

Surgihoney (SH) was compared with two modified honeys, Prototype 1 (PT1) and Prototype 2 (PT2) using a bioassay method against a standard strain of *Staphylococcus aureus*. Further work studied the rate of generation of hydrogen peroxide from these preparations.

Results:

Surgihoney antimicrobial activity was shown to be largely due to hydrogen peroxide production. By modification of Surgihoney, two more potent honey prototypes were shown to generate between a two- and three-fold greater antibacterial activity and up to ten times greater peroxide activity.

Conclusions:

Surgihoney is a clinically available wound antiseptic dressing that shows good antimicrobial activity. Two further honey prototypes have been shown to have antimicrobial activity that is possible to be enhanced due to demonstrated increases in peroxide activity.

Methods

1. Determination of Honey Activity by Bioassay Method

The antibacterial activity of Surgihoney (SH) and two modified honeys, Prototype 1 (PT1) and Prototype 2 (PT2) was measured using *Staphylococcus aureus* (NCIMB 9518) and expressed as the equivalent % phenol. Values were calculated of the mean from three sample replicates tested, repeated on three days.

Assay Method. The agar well diffusion method used was adapted from the punch plate assay for inhibitory substances described in the Microbiology Standard Methods Manual for the New Zealand Dairy Industry (1982)[ Bee Products Standards Council: Proposed standard for measuring the non peroxide activity of honey. In. New Zealand: Bee Products Standards Council; 1982.].

Inoculum Preparation. Overnight culture was adjusted to an absorbance of 0.5 measured at 540 nm using sterile nutrient broth as a blank and a diluents and a cuvette with a 1 cm pathway.

Assay Plate preparation. A volume of 100 pl of the culture adjusted to 0.5 absorbance was used to seed 150 ml nutrient agar to make the assay plates. The agar was swirled to mix thoroughly and poured into large petri dishes which had been placed on a level surface. As soon as the agar was set the plates were placed upside down overnight before using the next day. For assay these seeded plates were removed from 4° C. and allowed to stand at room temperature for 15 min before cutting 7.0 mm diameter wells into the surface of the agar. 250 pl of test material (sample or standard) was placed into each well.

Catalase solution. A 200 mg/ml solution of catalase from bovine liver (Sigma C9322, 2900 units/mg) in distilled water was prepared fresh each day.

Sample preparation. Primary sample solutions were prepared by adding 4 g of sample to 4 ml of distilled water in universals and placed at 37° C. for 30 minutes to aid mixing. To prepare secondary solutions, 2 ml of the primary sample solution was added to 2 ml of distilled water in universals and mixed for total activity testing and 2 ml of the primary sample solution was added to 2 ml of catalase solution and mixed for non-peroxide activity.

Preparation of phenol standards. Standards (w/v) 10%, 30%, 50% phenol were prepared by dissolving phenol in water. Phenol standards were brought to room temperature in the dark before use and were mixed thoroughly before addition to test wells. Each standard was placed in three wells to test in triplicate. Standards were kept at 4° C. with an expiry date of one month.

Sample and standard application. All samples and standards were tested in triplicate by adding 250 µl to each of 3 wells.

Plate incubation. After application of samples the plates were incubated for approximately 18 hours at 37° C. The diameter of inhibition zones, including the diameter of the well (7.0 mm), was recorded.

Calculation of antibacterial activity of samples. The mean diameter of the clear zone around each phenol standard was calculated and squared. A standard graph was plotted of % phenol against the square of the mean diameter of the clear zone. A best-fit straight line was obtained using linear regression and the equation of this line was used to calculate the activity of each diluted honey sample from the square of the mean measurement of the diameter of the clear zone. To allow for the dilution (assuming the density of the Surgihoney to be 1.35 g/ml) this figure was multiplied by a factor of 4.69 and the activity of the samples was then expressed as the equivalent phenol concentration (% w/v).

Total Activity: all the activity, including activity due to hydrogen peroxide ($H_2O_2$).

Non-Peroxide Activity: $H_2O_2$ is removed by treating samples with catalase enzyme.

2. Determination of Honey Activity by $H_2O_2$ Method

The activity was measured using the Merckoquant®1.10011. & 1.10081.

Peroxide Test Kits. Concentrations expressed as the equivalent mg/L $H_2O_2$

Samples were diluted 1:10 with purified water. Following 5 min incubation, all samples were measured for $H_2O_2$ production each hour over a 12 hour period followed by 24 and 48 hour time points.

Method of Determination. Peroxidase transfers oxygen from the peroxide to an organic redox indicator, which is then converted to a blue coloured oxidation product. The peroxide concentration is measured semi-quantitatively by visual comparison of the reaction zone of the test strip with the fields of a colour scale. The reaction zone of the test strip is immersed into the Surgihoney sample for 1 sec, allowing excess liquid to run off the strip onto an absorbent paper towel and after 15 seconds (Cat. No. 110011), 5 seconds (Cat. No. 110081), after which a determination of the colour formed in the reaction zone more precisely coincided with the colour fields scale.

Results

1. Activity Rating

The antimicrobial activity produced by the modification of the honey samples resulted in a two-fold and almost three-fold respectively increase in phenol activity with PT1 and PT2 compared with Surgihoney alone. The results for the three samples of Surgihoney (SH) and two modified prototypes, PT1 and PT2 are shown in Table 17.

2. Determination of Honey Activity by $H_2O_2$ Method

The prototype modifications are observed to generate up to seven and ten times the hydrogen peroxide activity of Surgihoney. The results for the three samples are shown in FIG. 38. By taking the maximum level of hydrogen peroxide output for each of the three honey prototypes and plotting this against the total phenol activity a linear relationship is observed (FIG. 39).

Discussion

The results from this work show that the main antimicrobial activity of Surgihoney (SH) and two modified prototypes, PT1 and PT2 are due to hydrogen peroxide. This is a similar finding to certain other honeys from a variety of floral sources. However, unlike previous work the availability of hydrogen peroxide from the samples is able to be enhanced and at 12 hours is seven and ten times respectively the value for Surgihoney (SH) alone. There is a striking linear relationship between the antimicrobial activity and the maximum output of hydrogen peroxide from the three honey prototypes.

This peroxide activity offers potent antimicrobial activity that is ideally suited for a wound dressing that is applied to acute or chronic wounds to treat or prevent wound infections. Whilst a small amount of catalase is present in wounds and serum level of catalase in males has been reported as 50 kU/l it has been shown that catalase activity in healing wounds actually decrease during the first week post-wounding and activity levels of catalase recover to its original level at two weeks post-wounding. Such concentrations of catalase are thus extremely unlikely to influence the antimicrobial activity observed with exogenously applied Surgihoney or the two modified prototypes, PT1 and PT2.

The ideal characteristics for an antimicrobial wound dressing are: effectiveness, lack of toxicity, ease of use, patient and clinician acceptability and value for money. Hydrogen peroxide is an effective antimicrobial and is already used as a biocide for its potent activity against vegetative bacteria, yeasts and spores. It produces its antimicrobial effect through chemical oxidation of cellular components.

The human toxicity of hydrogen peroxide is concentration dependent and one study has claimed that the differential concentrations for antimicrobial and human toxicity might overlap. By contrast, certain preparations of honey have been shown to be an effective antimicrobial agent by supplying low concentrations of hydrogen peroxide to wounds continuously over time rather than as a large amount at the time of dressing and without such toxicity. Indeed there is compelling evidence that where physiological levels of hydrogen peroxide are applied to mammalian cells there is a stimulation of biological responses and activation of specific biochemical pathways in these cells.

Clearly Surgihoney and the two modified prototypes, PT1 and PT2 are antimicrobial dressings that offer effective hydrogen peroxide release over at least 24 hours.

Conclusions

Surgihoney and the two modified prototypes, PT1 and PT2 have been shown to have potent antimicrobial activity against a standard strain of *Staphylococcus aureus*. These antimicrobial activities have been shown to be due to hydrogen peroxide. The activity is scalable and can be described in terms of hydrogen peroxide activity. These modified honeys offer a dressing that is effective, non-toxic and easy to administer.

Table 17 showing the peroxide and non-peroxide antibacterial activities of Surgihoney (SH) and two modified prototypes, PT1 and PT2 against *Staphylococcus aureus* (NCIMB 9518).

| Sample Name | Batch No. | Total Activity (% phenol) | Non-Peroxide Activity (% phenol) |
|---|---|---|---|
| Surgihoney | 2015-06-018B | 32 | 0 |
| Surgihoney PT1 | HHI4110311 | 65 | 7 |
| Surgihoney PT2 | HHI14110312 | 83 | 10 |

EXAMPLE 44

This example sets out a preferred honey-based composition of the invention that comprises honey and added glucose oxidase (referred to as "Active honey").
Alcoholic Gel

| | |
|---|---|
| Carbopol 940 | 0.3% |
| Triethanolamine | 0.4% (needed for pH and stability control) |
| Active honey (5+) | 65% |
| Ethanol | 25.0% |
| water | qs |

Usage: for the treatment of acne. Not to be used on broken skin.

"Active Honey (5+)" is used to indicate that more glucose oxidase should be used than in other formulations without the (5+) designation.

EXAMPLE 45

This example sets out a preferred honey-based composition of the invention that comprises honey and added glucose oxidase (referred to as "Active honey").
Aqueous Spray
25 ml plastic bottle containing:

| | |
|---|---|
| Active honey | 10 g |
| Triton CF | 0.1 g |
| Maltodextrin, or corn Starch | 1 g |

Usage: wounds in general, and for application to burns

Triton CF acts as a surfactant in this composition. Maltodextrin, or corn starch acts as a film former.

EXAMPLE 46

This example sets out a preferred honey-based composition of the invention that comprises honey and added glucose oxidase (referred to as "Active honey").
Non-Aqueous Spray

| | |
|---|---|
| Active honey | 70% |
| Proplyene Glycol | 30% |

Usage: wounds in general

EXAMPLE 47

This example sets out a preferred honey-based composition of the invention that comprises honey and added glucose oxidase (referred to as "Active honey").
Dressing—Plastic Pouch

| | |
|---|---|
| Range of Calcium Alginate dressings | 10 cm × 10 cm, 20 cm × 20 cm |
| Active honey | 10% w/w |

Usage: wound debridement, for relatively heavily exudating wounds. This composition provides a relatively moist environment.

EXAMPLE 48

This example sets out a preferred honey-based composition of the invention that comprises honey and added glucose oxidase (referred to as "Active honey").
Honey and Analgesic

| | |
|---|---|
| Active honey | 99% |
| Ibuprofen | 1% |

Usage: for all stages of wound management to provide pain management in wound healing

EXAMPLE 49

This example sets out a preferred honey-based composition of the invention that comprises honey and added glucose oxidase (referred to as "Active honey").
Powder
  Active honey
  Maltodextrin
  Ibuprofen
  Microcrystalline Cellulose (CMC)
  Polyvinyl Pyrrolidone (PVP)

Preferably ibuprofen is included in the composition at 1-2% w/w. The other components can be varied, for example to achieve different levels of moisture absorption.

Usage: packaging in foil to prevent water uptake. PVP—provides granulation. CMC—provides a moisture desiccant.

EXAMPLE 50

This example sets out a preferred honey-based composition of the invention that comprises honey and added glucose oxidase (referred to as "Active honey").
Wound Debridement Reconstituted Aqueous solution, comprising Active honey (for example, 5-50% Active honey), optionally also including analgesic, preferably ibuprofen, suitably at 1-2% w/w.

Usage: for example in a dispenser (such as a pump dispenser), as a wound rinse following debridement to provide an early start to wound healing and pain relief.

EXAMPLE 51

This example sets out a preferred honey-based composition of the invention that comprises honey and added glucose oxidase (referred to as "Active honey").
Foam Dressing
  Polyurethane backing to absorb exudates
  island of calcium alginate soaked in Active honey
  silicone to stop adhering to wound Usage: foam-based dressing to assist in mopping up wound exudates.

EXAMPLE 52

This example sets out a preferred honey-based composition of the invention that comprises honey and added glucose oxidase (referred to as "Active honey").
Fungal Nail Treatment
  Plaster with Active Honey (5+) in a foam well
  Hydroxypropylcellulose
  Glycerol
  Isopropyl Alcohol
  Citric Acid
  Monohydrate Usage: for the treatment of fungal nail infections

EXAMPLE 53

This example sets out a preferred honey-based composition of the invention that comprises honey and added glucose oxidase (referred to as "Active honey").
Throat Spray
Honey and glycerol, preferably comprising 5-20% honey
Usage: sore throats. The formulation could be in a dual dispenser for spraying, or reconstituted with water prior to use, and then sprayed.

EXAMPLE 54

This example sets out a preferred honey-based composition of the invention that comprises honey and added glucose oxidase (referred to as "Active honey").
Pommade
Active honey 25%
White petrolatum
Light liquid paraffin
Talc
Kaolin
Zinc oxide
Usage: for the treatment of infected eczema

EXAMPLE 55

This example sets out a preferred honey-based composition of the invention that comprises honey and added glucose oxidase (referred to as "Active honey").
Lip Balm

| Petrolatum 5594 | 50% |
| --- | --- |
| Microcrystalline Wax | 9% |
| Cyclomethicone D5 | 31% |
| Active Honey | 10% |

Usage: for chaffed lips

EXAMPLE 56

This example sets out a preferred honey-based composition of the invention that comprises honey and added glucose oxidase (referred to as "Active honey").
Cream

| Honey | 15% |
| --- | --- |
| Carbomer | 2.63% |
| Dimethicone | 0.13% |
| Disodium Lauryl Sulphosuccinate | 0.05% |
| Disodium Edetate | 0.13% |
| Glycerol | 5.26% |
| Silica Colloidal Hydrated | 0.33% |
| Poloxamer | 0.26% |
| Sodium Hydroxide | 0.41% |
| Purified Water | 85.03% |

Usage: for treating acne. Honey is known to be active against *Propionibacterium acnes*.

The invention claimed is:

1. A sterile storage-stable composition for generating antimicrobial activity for treating microbial infections, which comprises:
    an enzyme that is able to convert a substrate to release hydrogen peroxide; and
    a honey that lacks catalase activity and lacks glucose oxidase activity, and that includes a substrate for the enzyme;
    wherein the enzyme is additional to any enzyme activity able to convert the substrate to release hydrogen peroxide that may be present in the honey,
    wherein the composition does not include sufficient free water to allow the enzyme to convert the substrate or has a water activity of 0.47 to 0.7;
    wherein the composition comprises substantially no hydrogen peroxide; and
    wherein the composition does not comprise ozonized honey or ozonated oil.

2. A composition according to claim 1, wherein the enzyme is glucose oxidase and the substrate for the enzyme is D-glucose.

3. A composition according to claim 1, further comprising an antioxidant.

4. A composition according to claim 1, which has been sterilised by exposure to gamma irradiation.

5. A composition according to claim 1 that does not comprise any added peroxidase.

6. A composition according to claim 1, wherein the enzyme is a purified enzyme.

7. A composition according to claim 1, wherein the honey that lacks catalase activity and lacks glucose oxidase activity is a pasteurized honey.

8. A composition according to claim 1, wherein the composition has a water activity of 0.47 to 0.7.

* * * * *